US012692319B2

(12) United States Patent
Satpayev et al.

(10) Patent No.: US 12,692,319 B2
(45) Date of Patent: *Jul. 28, 2026

(54) COMPOSITIONS AND METHODS REGARDING ENGINEERED AND NON-ENGINEERED γ δ T-CELLS FOR TREATMENT OF HEMATOLOGICAL TUMORS

(71) Applicant: ADICET THERAPEUTICS, INC., Redwood City, CA (US)

(72) Inventors: Daulet Kadyl Satpayev, Menlo Park, CA (US); Marissa Ann Herrman, Menlo Park, CA (US); Jason Michael Romero, Menlo Park, CA (US); Yifeng Frank Jing, Menlo Park, CA (US); Zili An, Menlo Park, CA (US); Aya Jakobovits, Menlo Park, CA (US)

(73) Assignee: ADICET THERAPEUTICS, INC., Redwood City, CA (US)

( * ) Notice: Subject to any disclaimer, the term of this patent is extended or adjusted under 35 U.S.C. 154(b) by 1285 days.

This patent is subject to a terminal disclaimer.

(21) Appl. No.: 17/281,574

(22) PCT Filed: Oct. 1, 2019

(86) PCT No.: PCT/US2019/054132

§ 371 (c)(1),
(2) Date: Mar. 30, 2021

(87) PCT Pub. No.: WO2020/072536

PCT Pub. Date: Apr. 9, 2020

(65) Prior Publication Data

US 2021/0388100 A1 Dec. 16, 2021

Related U.S. Application Data

(60) Provisional application No. 62/739,822, filed on Oct. 1, 2018.

(51) Int. Cl.
| | |
|---|---|
| *A61K 40/31* | (2025.01) |
| *A61K 38/17* | (2006.01) |
| *A61K 38/20* | (2006.01) |
| *A61K 39/395* | (2006.01) |
| *A61K 40/11* | (2025.01) |
| *A61K 40/42* | (2025.01) |
| *A61P 35/00* | (2006.01) |
| *C07K 14/54* | (2006.01) |
| *C07K 14/705* | (2006.01) |
| *C07K 16/28* | (2006.01) |
| *C12N 5/0783* | (2010.01) |
| *A61K 39/00* | (2006.01) |

(52) U.S. Cl.
CPC ........ *C07K 16/2887* (2013.01); *A61K 38/177* (2013.01); *A61K 38/1774* (2013.01); *A61K 38/2086* (2013.01); *A61K 39/3955* (2013.01);
*A61K 40/11* (2025.01); *A61K 40/31* (2025.01); *A61K 40/4215* (2025.01); *A61K 40/4221* (2025.01); *A61P 35/00* (2018.01); *C07K 14/5443* (2013.01); *C07K 14/7051* (2013.01); *C07K 14/70517* (2013.01); *C07K 14/70578* (2013.01); *C07K 16/2803* (2013.01); *C07K 16/2878* (2013.01); *C12N 5/0636* (2013.01); *A61K 2039/505* (2013.01); *A61K 2239/38* (2023.05); *A61K 2239/46* (2023.05); *A61K 2239/48* (2023.05); *C07K 2317/565* (2013.01); *C07K 2317/73* (2013.01); *C07K 2317/74* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 7,728,114 B2 * | 6/2010 | Mach | ......................... | A61P 1/04 |
| | | | | 530/388.22 |
| 9,539,251 B2 * | 1/2017 | Sampath | ................ | A61K 31/18 |

(Continued)

FOREIGN PATENT DOCUMENTS

| | | |
|---|---|---|
| CN | 104087607 A | 10/2014 |
| JP | 2018-512161 A | 5/2018 |

(Continued)

OTHER PUBLICATIONS

Dwyer et al., Fueling Cancer Immunotherapy With Common Gamma Chain Cytokines, Front. Immunol. 10:263, 18 pages, Feb. 2019.*

(Continued)

*Primary Examiner* — Zachary S Skelding
(74) *Attorney, Agent, or Firm* — Todd Lorenz

(57) ABSTRACT

Aspects of the invention include compositions and methods for treatment of hematological tumors with engineered or non-engineered γδ-T cells. In some embodiments, the γδ-T cells comprise a chimeric antigen receptor (CAR) construct. The CAR construct can contain an anti-CD20 binding domain or anti-B cell maturation antigen (BCMA) binding domain, a CD8 hinge and transmembrane domain, a costimulatory domain, a CD3 ζ signalling domain, a combination thereof, or all thereof. The CAR construct can contain a domain encoding for a secreted common gamma chain cytokine such as a sIL 15 domain.

37 Claims, 19 Drawing Sheets

Specification includes a Sequence Listing.

(56) References Cited

U.S. PATENT DOCUMENTS

| | | | | |
|---|---|---|---|---|
| 2004/0167319 A1* | 8/2004 | Teeling | .................... | A61P 19/02 |
| | | | | 530/388.22 |
| 2009/0035322 A1* | 2/2009 | Martin | .................... | A61P 19/02 |
| | | | | 435/69.6 |
| 2016/0046724 A1* | 2/2016 | Brogdon | ............ | C07K 14/7051 |
| | | | | 435/328 |
| 2016/0175358 A1* | 6/2016 | Jakobovits | ............. | C12N 15/00 |
| | | | | 435/372.3 |
| 2018/0125889 A1 | 5/2018 | Leek et al. | | |
| 2020/0289561 A1 | 9/2020 | Qian et al. | | |
| 2021/0094994 A1* | 4/2021 | Heczey | .............. | C07K 14/7051 |
| 2021/0154231 A1 | 5/2021 | Li et al. | | |
| 2021/0252056 A1* | 8/2021 | Metelitsa | ............. | C12N 5/0646 |
| 2021/0363245 A1* | 11/2021 | Kochenderfer | .... | A61K 39/4631 |
| 2023/0071098 A1 | 3/2023 | Tamada et al. | | |

FOREIGN PATENT DOCUMENTS

| | | | | |
|---|---|---|---|---|
| WO | WO-2006130458 A2 * | 12/2006 | .............. | A61P 37/02 |
| WO | WO 2009/018411 A1 | 2/2009 | | |
| WO | WO 2016034666 A1 | 3/2016 | | |
| WO | WO 2016138491 A1 | 9/2016 | | |
| WO | WO 2016139487 A1 | 9/2016 | | |
| WO | WO 2016166544 A1 | 10/2016 | | |
| WO | WO 2016/199140 A1 | 12/2016 | | |
| WO | WO 2016/199141 A2 | 12/2016 | | |
| WO | WO 2016/201394 A1 | 12/2016 | | |
| WO | WO 2017/147383 A1 | 8/2017 | | |
| WO | WO 2017/197347 A1 | 11/2017 | | |
| WO | WO 2018/019772 A1 | 2/2018 | | |
| WO | WO 2018/085690 A1 | 5/2018 | | |
| WO | WO 2018/087557 A1 | 5/2018 | | |
| WO | WO 2018/098365 A1 | 5/2018 | | |
| WO | WO 2018/131586 A1 | 7/2018 | | |
| WO | WO 2018/138522 A1 | 8/2018 | | |
| WO | WO 2018/147805 A1 | 8/2018 | | |
| WO | WO 2018/229530 A1 | 12/2018 | | |

OTHER PUBLICATIONS

Fan, M., Plasmids 101_ Multicistronic Vectors, Retreived onine from <URL:https://blog.addgene.org/plasmids-101-multicistronic-vectors> [retreived on Mar. 27, 2024), 9, Sep. 2014.*

Deniger et al., Bispecific T-cells Expressing Polyclonal Repertoire of Endogenous γδT-cell Receptors and Introduced CD19-specific Chimeric Antigen Receptor, Mol. Ther. 21(3):638-647, 2013.*

Capsomidis et al. (Molecular therapy: the journal of the American Society of Gene Therapy, 26(2), 354-365, 2017). (Year: 2017).*

Almeida et al. (Clin Cancer Res; 22(23); 5795-804 and supplemental pp. 1-15. 2016). (Year: 2016).*

Siegers et al. (Cytotherapy, 2011; 13: 753-764). (Year: 2011).*

Harlow et al. (Antibodies, A Laboratory Manual, Cold Spring Harbor laboratory, 1988, pp. 37-47). (Year: 1988).*

Edwards et al. (J. Mol. Biol. (2003) 334, 103-118). (Year: 2003).*

Lloyd et al. (Protein Engineering, Design & Selection vol. 22 No. 3 pp. 159-168, 2009). (Year: 2009).*

Lamb et al. (Bone Marrow Transplantation (2018) 53:766-769). (Year: 2018).*

Fisher et al. (Clin Cancer Res; 20(22); 5720-32. 2014). (Year: 2014).*

Meyer et al. (British Journal of Haematology, 2018, 180, 808-820 and, and Supplemental pp. 1-9). (Year: 2018).*

Klein et al. (mAbs, 5:1, 22-33 (2013)). (Year: 2013).*

Somasundaram et al. (Nat Commun. Sep. 19, 2017;8(1):607). (Year: 2017).*

Klein C 2013 mAbs, 5:1, 22-33. (Year: 2013).*

Till et al., Blood. 2008; 112: 2261-2271. (Year: 2008).*

Wang et al., Clinical Immunology (2014) 155, 160-175. (Year: 2014).*

Alabanza et al., "Function of Novel Anti-CD19 Chimeric Antigen Receptors with Human Variable Regions Is Affected by Hinge and Transmembrane Domains", Molecular Therapy: The Journal of the American Society of Gene Therapy, vol. 25, No. 11, pp. 2452-2465 (2017).

Chmielewski et al., "TRUCKs: the fourth generation of CARs", Expert Opinion on Biological Therapy, vol. 15, No. 8, pp. 1145-1154 (2015).

Cordova et al. "Characterization of Human γδ T Lymphocytes Infiltrating Primary Malignant Melanomas", PLoS One, vol. 7(11), e49878 (2012).

Fisher et al., "Engineering Approaches in Human Gamma Delta T Cells for Cancer Immunotherapy", Frontiers in Immunology, vol. 9, (2018).

Kenna et al., "Distinct subpopulations of γδT cells are present in normal and tumor-bearing human liver", Clinical Immunology, vol. 113, pp. 56-63 (2004).

Liu et al., "Targeting Alpha-Fetoprotein (AFP)-MHC Complex with CAR T-Cell Therapy for Liver Cancer", Clinical Cancer Research, vol. 23, No. 2, pp. 478-488 (2017).

Markley et al., "IL-7 and IL-21 are superior to IL-2 and IL-15 in promoting human T cell-mediated rejection of systemic lymphoma in immunodeficient mice", Blood, vol. 115, No. 17, p. 3508-3519 (2010).

Nishida et al., "Glypican 3-Targeted Therapy in Hepatocellular Carcinoma", Cancers, vol. 11(9), (2019).

Rafiq et al., "Optimized T-cell receptor-mimic chimeric antigen receptor T cells directed toward the intracellular Wilms Tumor 1 antigen", Leukemia, vol. 31, No. 8, pp. 1788-1797 (2017).

Ribot et al., "Searching for "signal 2": costimulation requirements of γδT cells", Cell. Mol. Life Sci. (2011) 68:2345-2355.

Tassev, D.V., "Generation and Use of HLA-A2-Restricted, Peptide-Specific Monoclonal Antibodies and Chimeric Antigen Receptors", May 1, 2011; Retrieved from the Internet: URL:https://www. sloankettering.edu/sites/default/files/node/165658/document/final-dimiter-tassev.pdf.

* cited by examiner

Sequences of VL and VH domains of CD20 binders received from REGN

VH CDS

GAAGTACAGCTGGTGGAGTCTGGGGGAGGCTTGGTACAGCCTGGCAGGTCCCTGAGACTCTCCTGTGCAGGTCCCTGAGACTCTCCTGTGTAGCCTCTGGATTCACCTTTAATGATTATGCCATGCACTGGGTCCGGCAAGCTCCAGGGAAGGGC
CTGGAATGGGTCTCAGTTATTAGTTGGAATAGTGGAATAGTGATAGCATAGGCTATGCGGACTCTGTGAAGGGCCGATTCACCATCTCCAGAGACAACGCCAAGAACTCCCTGTATCTGCAAATGCACAGTCTGAGAGCTGA
GGACACGGCCGTCTTGTATTACTGTGCAAAAGATAATCACTATGGTTCGGGAGTTATTACTACCAATACGGTATGGACGTCTGGGGCCAAGGGACCACGGTCACCGTCTCCTCAG

VH PEP

EVQLVESGGGLVQPGRSLRLSCVASGFTFNDYAMHWVRQAPGKGLEWVSVISWNSDSIGYADSVKGRFTISRDNAKNSLYLQMHSLRAEDTALYYCAKDNHYGSGSYYYYQYGMDVWGQGTTVTVSS

VK CDS

GAAATAGTGATGACGCAGTCTCCAGCCACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCC
CGACTCCTCATCTATGGTACATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTATTACTGTCAA
CAATATAATAACTGGCCGCCTCACTTTCGGCGGAGGGACCAAGGTGGAGATCAAAC

VK PEP

EIVMTQSPATLSVSPGERATLSCRASQSVSSNLAWYQQKPGQAPRLLIYGTSTRATGIPARFSGSGSGTEFTLTISSLQSEDFAVYYCQQYNNWPLTFGGGTKVEIK

9C11

VH CDS

CAGGTGCAGCTGGTGGAGTCTGGGGGAGGACTCGGTCAAGCCTGGAGGGTCCCTGAGACTCTCCTGTGCAGCCTCTGGATTCACCTTCAGTGACTCCTACATGACTTGGATCCGCCAGGCTCCAGGGAAGGG
GCTGGAGTGGGTTTCATTCATTAGTAGTAGTGGAAGTACCATATATTATGCAGACTCTGTGAAGGGCCGATTCACCATTTCCAGGGACAAGTCATTGTATCTGCAGATGAACAGACTGAGAGCCG
AGGACACGGCCGCCGTGTATTACTGTGCGAGAGAAGAACCAGGAAACTACGTCTATTACGGTATGGACGTCTGGGGCCAAGGGACCACGGTCACCGTCTCCTCAG

VH PEP

QVQLVESGGGDSVKPGGSLRLSCAASGFTFSDSYMTWIRQAPGKGLEWVSFISSSGSTIYYADSVKGRFTISRDNVKKSLYLQMNRLRAEDTAVYYCAREEPGNYVYYGMDVWGQGTTVTVSS

VK CDS

GAAATTGTGGTGACACAGTCTCCAGCCACCCTGTCTTTGTCTCCAGGGGAAAGAGCCACCCTCTCCTGCAGGACCAGTCAGACTACCAGCTACTTAGCCTGGTACCAGCAGAAACCTGGCCAGGCTCCCA
GGCTCCTCATCTATGATGCATCCAACAGGGCCGCTGGCATCCCAGCCAGGTTCAGTGGCAGTGGGTCTGGGACAGACTTCACTCTCACCATCAACAGCCTAGAGCCTGAAGATTTTGCAGTTTATTACTGTCAG
CTGCGTACCAACTGGATCACCTTCGGCCAAGGGACACGACTGGAGATTAAAC

VK PEP

EIVVTQSPATILSLSPGERATLSCRTSQTTTSYLAWVRQKPGQAPRLLIYDASNRAAGIPARFSGSGSGTDFTLTINSLEPEDFAVYYCQLRTNWITFGQGTRLEIK

Sequences of VL and VH domains of CD20 binders received from REGN

VH CDS

GAAGTGCAACTGGTGGAGTCTGGGGGAGGCTTGGTACAGCCTGGCAGGTCCCTGAGACTCTCCTGTGCAGCCTCTGGATTCACCTTTATGATTATGCCATGCACTGGGTCCGGCAAGCTCCAGGGAAGG
GCCTGGAGTGGGTCTCAGGTATTAGTTGGAATAGTGGTTACAATAGGCTATGCGGACTCTGTGAAGGGCCGATTCACCATCTCCAGAGACAACGCCAAGAACTCCCTGTATCTGCAAATGAACAGTCTGAGA
GCTGAGGACACGGCCTTGTATTACTGTGCAAAAGATAAACAGCTATGGAAAGTTCTACTACGGTTTGACGTCTGGGGCCAAGGGACCACGGTCACCGTCTCCTCAG

VH PEP

EVQLVESGGGLVQPGRSLRLSCAASGFTFMYAMHWVRQAPGKGLEWVSGISWNSGYNRYADSVKGRFTISRDNAKNSLYLQMNSLRAEDTALYYCAKDNSYGKFYYGLDVWGQGTTVTVSS

VK CDS

GAAATAGTGATGACGCAGTCTCCAGCACCCTGTCTGTGTCTCCAGGGGAAAGAACCACCCTCTCCTGCAGGGCCAGTCAGAGTGTTAGCAGCAACTTAGCCTGGTACCTTCAGAAACCTGGCCAGGCTC
CCAGGCTCCTCATCTATGGTGCATCCACCAGGGCCACTGGTATCCCAGCCAGGTTCAGTGCAGTGGGTCTGGGACAGAGTTCATTCTCACCATCAGCAGCCTGCAGTCTGAAGATTTTGCAGTTTATTACT
GTCAGCAGTATAATAAACTGGCCAGCACTTCGCCAAGGGACACGGCTGGAGATTAAAC

VK PEP

EIVMTQSPATLSVSPGERTTLSCRASQSVSSNLAWYLQKPGQAPRLLIYGASTRATGIPARFSGSGSGTEFILTISSLQSEDFAVVYCQQYNNWPITFGQGTRLEIK

2B7

VH CDS

GAAGTGCAGCTGGTGGAGTCTGGGGGAGGCGTTGGTACAGCCTGGCAGGTCCCTGCGACTCTCCTGTGCAGCCTCTGGATTCACCTTTGGTACGGCCTCCTGCAGCCTCTGGATTCACCTTTGAGATTATACCATGCACTGGGTCCGGCAAGGTCCAGGGAAG
GGCCTGGAAATGGGTCTCAGGTATTAGTTGGAATAGTGGTGGAATAGTGATTACATAGGCTATGCGGACTCTGTGAAGGGCCGATTCACCATCTCCAGAGACAACGCCAAGAACTCCCTGTATCTGCAAATGAACAGTCTGAG
AGTTGAGGACACGGCCTTGTATTACTGTGCAAAGCTCAGTGCAGCTACTTCTACGGAGTGGACGTCTGGGGCCAAGGGACCACGGTCACCGTCTCCTCAG

VH PEP

EVQLVESGGGLVQPGRSLRLSCAASGFTFRDYTMHWVRQGPGKGLEWVSGISWNSDYIGYADSVKGRFTISRDNAKNSLYLQMNSLRVEDTALYYCAKLSGTYRDYFYGVDVWGQGTTVTVSS

VK CDS

GAAATTGTGTTGACACAGTCTCCAGCCACCCTGTCTTTGTCTCCAGGGGAAAGAGCCGCCCTCTCCTGCAGGGCCAGTCAGAGTGTTAGCAACTACTTAGCCTGGTACCAACAGAAACCTGGCCAGGCTCC
CAGGCTCCTCATCTATGATGCATCCAACAGGGCCACTGGCATCCCAGCCAGGTTCAGTGGCAGTGGGTCTGGGACAGACTTCACTCTCACCATCAGCAGCCTAGAGCCTGAAGATTTTGCAGTTTATTACTG
TCAGCAGCGTAGCAACTGGCCGCTCACTTTCGGCGGAGGGACCAAGGTGGAGATCAGAC

VK PEP

EIVLTQSPATLSLSPGERAALSCRASQSVSNYLAWYQQKPGQAPRLLIYDASNRATGIPARFSGSGSGTDFTLTISSLEPEDFAVVYCQQRSNWPLTFGGGTKVEIR

Induction of apoptosis in normal B cells by Vδ1 cells transduced with various CD20 CAR constructs

CD20 CAR γδ T Cells Potently Kill Lymphoma Cell Lines

- Effective killing of HLA-Class 1 null (Daudi) cell line
- 3H7 CD20 CAR with 41BB co-stim domain potentiates innate killing of Raji cells Daudi Cell Line Raji Cell Line % Cytotoxicity Effector : Target Ratio Innate killing (unengineered cells)

CAR-mediated killing

FIG. 6
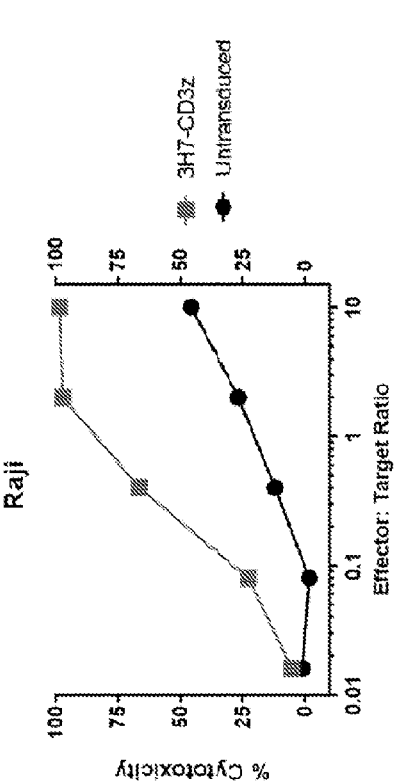
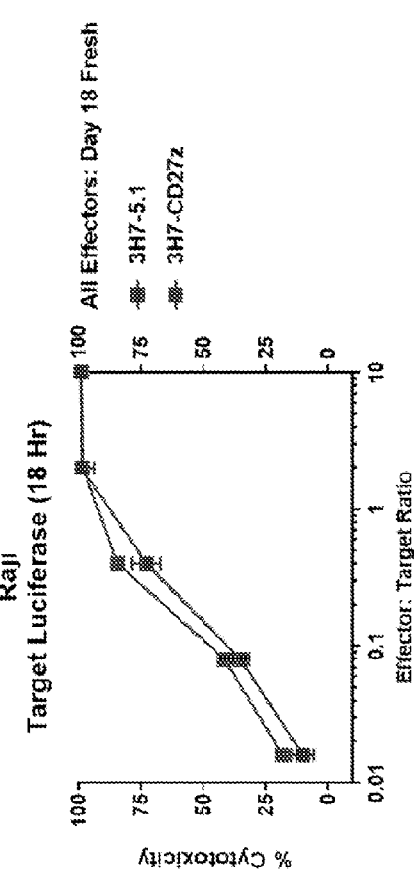

γδ T-cell proliferate in response to tumor

- Deaths in the αβ CAR T-cell group due to GvHD

- No GvHD observed in mice treated with γδ cells

- 3H7-5.1 CAR construct

Fig. 13

γδ T cell and CAR γδ T Cell Manufacturing Process Flow

Fig. 17
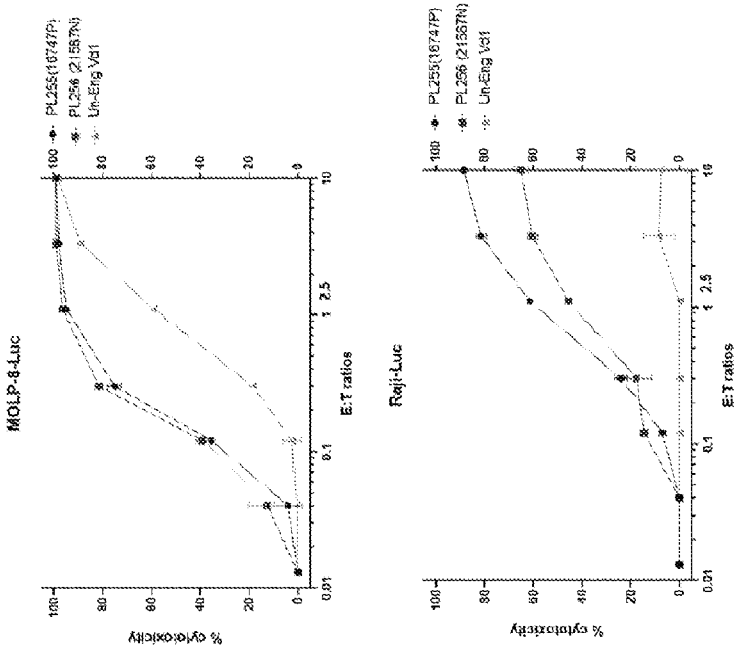
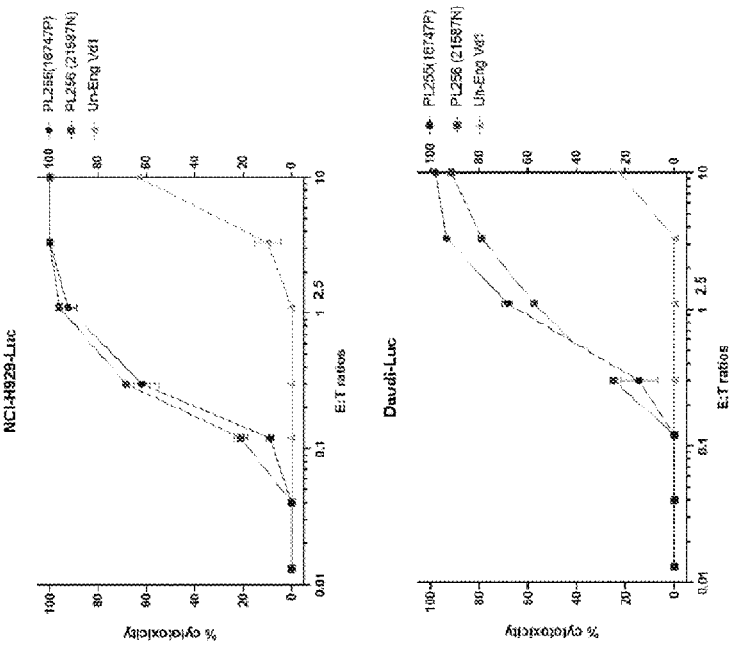

COMPOSITIONS AND METHODS REGARDING ENGINEERED AND NON-ENGINEERED γ δ T-CELLS FOR TREATMENT OF HEMATOLOGICAL TUMORS

CROSS-REFERENCES TO RELATED APPLICATIONS

This application claims the benefit of priority to U.S. Provisional Appl. No. 62/739,822, filed Oct. 1, 2018, the contents of which are incorporated in the entirety for all purposes.

SEQUENCE LISTING

The instant application contains a Sequence Listing which has been submitted electronically in ASCII format and is hereby incorporated by reference in its entirety. Said ASCII copy, created on Dec. 17, 2019, is named ADC-0005-PCT_SL.txt and is 147,616 bytes in size.

BACKGROUND OF THE INVENTION

Adoptive cellular therapy has undergone near constant iteration for more than thirty (30) years, from early days focusing on basic lymphokine activation and/or tumor infiltration to more recent strategies engineering these immune cells to express genetically engineered antigen receptors, such as chimeric antigen receptors (CARs)s. While there have been some hints and indications of the curative potential of these approaches along the way, much still remains to be done. In particular, successful tumor eradication by CAR-T lymphocytes depends on CAR-T cell persistence and effector function, but an excess of either can trigger graft-versus-host effects in the patient. As such the art is testing myriad co-stimulation strategies in both T and NK cells, and in αβ T cells in particular, with a view to balancing efficacy with safety. Notably, the practical translation of any of these various approaches to alloeneic γδ T cells is at best uncertain, given the current lack of understanding around the co-stimulation requirements of γδ T cells as compared to αβ T cells. See, e.g., Ribot et al., "Searching for "signal 2": costimulation requirements of γδ T cells", *Cell. Mol. Life Sci.* (2011) 68:2345-2355.

Accordingly, improved strategies are still needed to improve the specificity or selectivity of the cells, to improve safety of the cells, for example by reducing or avoiding graft versus host (GVH) effects, to improve efficacy of the cells, for example, by avoiding suppression of effector functions, and to improve the activity and/or survival of the cells upon administration to subjects. Provided are methods, cells, compositions, kits, and systems that meet such needs.

SUMMARY OF INVENTION

Aspects of the invention include an isolated nucleic acid sequence encoding a chimeric antigen receptor (CAR), wherein the CAR comprises a binding domain that specifically binds to a tumor associated antigen (TAA) expressed on a surface of a hematological tumor cell; an, e.g., CD8α, hinge domain; an, e.g., CD8α, transmembrane domain; a costimulatory signaling region, optionally wherein the costimulatory signaling region is selected from a 4-1BB (CD137) costimulatory signaling region and a CD27 costimulatory signaling region; and a CD3ζ signaling domain.

Aspects of the invention further include a non-engineered γδ T cell as described herein as well as a γδ T cell comprising a nucleic acid encoding a CAR construct as described herein, wherein the γδ T cell functionally expresses the nucleic acid encoded CAR on the surface of the γδ T cell. Aspects of the invention further include a plurality of engineered or non-engineered γδ T cells as described herein. Aspects of the invention further include a method of making a γδ T cell or plurality of γδ T cell s described herein wherein the method comprises transfecting γδ T cell(s) with a construct described herein. Aspects of the invention further include a pharmaceutical composition comprising a pharmaceutically acceptable excipient and a γδ T cell or plurality of γδ T cells as described herein. Aspects of the invention further include contacting the hematological tumor cell with a tumor cell killing effective amount of a γδ T cell as described herein.

In one aspect, the present invention provides an isolated nucleic acid sequence encoding a chimeric antigen receptor (CAR), wherein the CAR comprises (a) a binding domain that specifically binds to a tumor associated antigen (TAA) expressed on a surface of a hematological tumor cell; (b) a hinge domain, such as a CD8a hinge domain; (c) a transmembrane domain, such as a CD8α transmembrane domain; (d) a costimulatory signaling region or a combination of costimulatory signaling regions, optionally wherein the costimulatory signaling region is selected from a 4-1BB (CD137) costimulatory signaling region and a CD27 costimulatory signaling region; and (e) a signaling domain, such as a CD3ζ signaling domain. In some embodiments, the foregoing elements (a)-(e) are encoded on the sense strand of the isolated nucleic acid in 5' to 3' order.

In some embodiments, the binding domain specifically binds to CD20. In some embodiments, the binding domain selectively binds to an epitope within CD20 bound by, or competes for binding with, an anti-CD20 antibody selected from the group consisting of 3B9, 3H7, 2B7, and 9C11, preferably 3H7. In some embodiments, the binding domain comprises the complementary determining regions of an anti-CD20 antibody selected from the group consisting of 3B9, 3H7, 2B7, and 9C11, preferably 3H7.

In some embodiments, the isolated nucleic acid encodes a heavy chain variable region (HCVR) sequence and a light chain variable region (LCVR) sequence, e.g.: wherein the HCVR and LCVR sequences are SEQ ID NO:99 and 107 respectively; a heavy chain complementarity determining region 1, 2, and 3 sequence of SEQ ID NOs: 101, 103, and 105 respectively, and a light chain complementarity determining region 1, 2, and 3 sequence of SEQ ID NOs: 109, 111, and 113 respectively; a heavy chain complementary determining region 3 (HCDR3) and a light chain CDR3 (LCDR3), wherein the HCDR3 and LCDR3 are selected from the group consisting of SEQ ID NO:345 and 353; 201 and 209; and 249 and 257; a heavy chain variable region (HCVR) sequence and a light chain variable region (LCVR) sequence, wherein the HCVR and LCVR sequences are selected from the group consisting of SEQ ID NO: 339 and 347; 195 and 203; and 243 and 251; and/or a heavy chain complementary determining region 3 (HCDR3) domain and a light chain CDR3 (LCDR3) domain, wherein the HCDR3 domain comprises an amino acid sequence of the formula X1-X2-X3-X4-X5-X6-X7-X8-X9-X10-X11-X12-X13-X14-X15-X16-X17-X18-X19, wherein X1=A, V or T; X2=K; X3=D; X4=P, F or G; X5=S or H; X6=Y; X7=G; X8=S or H; X9=G or F; X10=S or Y; X11=Y, N or S; X12=Y, G or H; X13=G, L or S; X14=Y, M or D; X15=Y, D or V; X16=G, V or absent; X17=M or absent; X18=D or absent; X19=V or absent (SEQ ID NO: 369); and the LCDR3 domain comprises an amino acid sequence of the formula X1-X2-X3-X4-X5-X6-X7-X8-X9, wherein X1=Q; X2=Q; X3=R or S; X4=N, Y or F; X5=N, D, or Y; X6=W; X7=P; X8=L; X9=T (SEQ ID NO: 370).

In some embodiments, the isolated nucleic acid encodes a binding domain that specifically binds to CD19 or BCMA. In some embodiments, the binding domain specifically binds to BCMA. In some embodiments, the binding domain selectively binds to an epitope within BCMA bound by, or competes for binding with, an anti-BCMA binding region having a sequence selected from the group consisting of SEQ ID NO: 27 and 28; SEQ ID NO: 29 and 30; and SEQ ID NO: and 31 and 32. In some embodiments, b. the binding domain comprises the complementarity determining regions of an anti-BCMA binding region having a sequence selected from the group consisting of SEQ ID NO: 27 and 28; SEQ ID NO: 29 and 30; and SEQ ID NO: and 31 and 32.

In some embodiments of any one of the foregoing, or as described herein, the CAR comprises: a CD8α hinge domain comprising SEQ ID NO:1 (PTPAPTIASQPLSLRPE ACR-PAAGGAVHTRGLDFACDIY); or SEQ ID NO:2 (TTTPA-PRPPTPAPTIASQPLSLR PEACRPAAGGAVHTRGLD-FACDIY). In some embodiments of any one of the foregoing, or as described herein, the CAR comprises a CD8α transmembrane domain comprising SEQ ID NO:3 (IWAPLAGTCGVLLLSLVITLYC).

In some embodiments of any one of the foregoing, or as described herein, the CAR comprises a CD3ζ signaling domain comprising: SEQ ID NO:4 (RVKFSRSADAPA-YQQGQNQLYNELNLGRRREEYDVLDKRR-GRDPEMGGKPQRRKNPQ EGLYNELQKDKMAEAY-SEIGMKGERRRGKGHDGLYQGLSTATKDT YDALHMQALPPR) or SEQ ID NO:5 (RVKFSRSADA-PAYQQGQNQLYNELNLGRRREEYDVLDKRRGRDPEM GGKPRRKNPQEGLYNELQKDKMAEAYSEI-GMKGERRRGKGHDGLYQGLSTATKDTYD ALHMQALPPR).

In some embodiments of any one of the foregoing, or as described herein, the CAR comprises a 4-1BB costimulatory signaling region comprising SEQ ID NO:6 (KRGRKKLLY-IFKQPFMRPVQTTQEEDGCSCRFPEEEEGGCEL); or a CD27 costimulatory signaling region comprising SEQ ID NO:7. (QRRKYRSNKGESPVEPAEPCH YSCPREEEG-STIPIQEDYRKPEPACSP). In some embodiments of any one of the foregoing, or as described herein, the isolated nucleic acid encodes the 4-1BB costimulatory signaling region comprising SEQ ID NO:6 and the CD27 costimula-tory signaling region comprising SEQ ID NO:7.

In some embodiments of any one of the foregoing, or as described herein, the isolated nucleic acid further encodes a secreted cytokine; or a secreted common gamma chain interleukin; or a secreted common gamma chain interleukin such as IL-15, preferably wherein the secreted common gamma chain interleukin such as IL-15 comprises an inter-leukin polypeptide sequence operably linked to a secretion signal sequence (e.g., a secretion signal of SEQ ID NO: 33 or 49). In some embodiments, the isolated nucleic acid encodes a secreted IL-15, preferably wherein the IL-15 comprises the sequence of SEQ ID NO:34, more preferably wherein the IL-15 comprises the sequence of 34 operably linked to a secretion signal sequence of SEQ ID NO:33, or wherein the IL-15 comprises the sequence of SEQ ID NO: 34 operably linked to a secretion signal sequence of SEQ ID NO: 49. In some cases, the secreted cytokine, common gamma chain interleukin, and/or IL-15 are encoded carboxy terminal to the binding region, hinge and transmembrane domains, signaling domain, and/or costimulation endodo-main. In some cases, the secreted cytokine, common gamma chain interleukin, and/or IL-15 are encoded on the sense strand 3' of the region encoding the binding region, hinge and transmembrane domains, signaling domain, and/or costimulation endodomain.

In some embodiments, the nucleic acid encodes a multi-cistronic linker region configured to facilitate translation of the CAR and the secreted cytokine, common gamma chain cytokine, or IL-15 as separate polypeptides. In some embodiments, the multi-cistronic linker region encodes a self cleavage and/or a cleavage polypeptide sequence. In some cases, the self-cleavage sequence is a P2A, F2A, T2A, or E2A self cleavage sequence. In some cases, the cleavage sequence is a furin cleavage sequence. In some cases, the cleavage sequence (e.g., furin cleavage sequence) is amino terminal to a self cleavage sequence. In some embodiments, the multi-cistronic linker region encodes an internal ribo-some entry site. In some embodiments, the nucleic acid encodes a multi-cistronic linker region amino terminal to the interleukin or cytokine or interleukin or cytokine secretion signal, preferably wherein the multicistronic linker region comprises a sequence of any one of SEQ ID NOs: 43-45, 47, or 52-55 or a combination thereof, or encodes an internal ribosome entry site, e.g., SEQ ID NO: 56 or 60.

In some embodiments, the binding domain specifically binds to CD20 and the nucleic acid encodes SEQ ID NO:8, 9, 10, 11, 12, 46, 48, or 57 and 58. In some embodiments, the nucleic acid comprises the sequence of SEQ ID NO: 13, 14, 15, 16, 17, 50, 51, or 59. In some embodiments, the binding domain specifically binds to BCMA and the nucleic acid encodes SEQ ID NO: 35, 36, 37, or 38. In some embodiments, the nucleic acid comprises the sequence of SEQ ID NO: 39, 40, 41, or 42.

In some aspects, the present invention provides a poly-peptide or plurality of polypeptides encoded by any one of the foregoing isolated nucleic acids, or as described herein. In some embodiments, the present invention provides a T cell, such as a γδ T cell that comprises any one of the foregoing polypeptides or plurality of polypeptides. In some embodiments, the T cell expresses a functional binding domain as described herein on the surface of the T cell. In some embodiments, the T cell secretes a cytokine such as a common gamma chain interleukin, e.g., IL-15.

In some embodiments, the T cell exhibits in vitro and/or in vivo cell killing activity against a hematological tumor cell that exhibits cell surface expression of a tumor associ-ated antigen (TAA). In some embodiments, the hematologi-cal tumor cell killing activity of said, e.g., γδ, T cell is greater than an innate level of in vitro and/or in vivo hematological tumor cell killing activity in a control, e.g., γδ, T cell that does not comprise a CAR construct. In some embodiments, the, e.g., γδ, T cell exhibits the increased hematological tumor cell killing activity against HLA class I⁺hematological tumor cells. In some embodiments, the hematological tumor cell killing activity or increased hema-tological tumor cell killing activity persists for, for about, for at least, or for at least about, 6 days to 180 days after first contact with the hematological tumor cell.

In some embodiments, the, e.g., γδ, T cell proliferates in response to contact with a hematological tumor cell that exhibits cell surface expression of the tumor associated antigen (TAA). In some embodiments, the, e.g., γδ, T cell exhibits increased proliferation in response to contact with a hematological tumor cell that exhibits cell surface expres-sion of the tumor associated antigen (TAA) as compared to a control, e.g., γδ, T cell that does not functionally express the nucleic acid encoded CAR on the surface of the, e.g., γδ, T cell. In some embodiments, the, e.g., γδ, T cell proliferates in a host organism that comprises the hematological tumor cell that exhibits cell surface expression of the tumor associated antigen (TAA).

In some embodiments, the, e.g., γδ, T cell proliferation or increased, e.g., γδ, T cell proliferation persists for, for about, for at least, or for at least about, 6 days to 180 days after first contact with the hematological tumor cell. In some embodiments, the, e.g., γδ, T cell expresses pro-inflammatory cytokine(s), such as tumor necrosis factor alpha and/or interferon gamma after contact with the hematological tumor cell. In some embodiments, the, e.g., γδ, T cell expresses pro-inflammatory cytokine(s), such as tumor necrosis factor alpha and/or interferon gamma after contact with the hematological tumor cell, in an amount greater than a control T cell that does not functionally express the nucleic acid encoded CAR on the surface of the cell.

In some embodiments, the, e.g., γδ, T cell exhibits reduced, substantially reduced, essentially no, or no graft versus host response when introduced into an allogeneic host in comparison to a graft versus host response exhibited by an αβ T cell administered to an allogeneic host. In some embodiments, the T cell is a γ T cell. In some embodiments, the T cell is a δ T cell. In some embodiments, the T cell is a γδ T cell. In some embodiments, the T cell is a δ1, a δ2, a δ3, or a δ4 T cell, preferably a δ2⁻δ T cell, more preferably a δ1 δ T cell. In some embodiments, the T cell is a δ1, a δ2, a δ3, or a δ4 γδ T cell, preferably a δ2⁻ γδ T cell, more preferably a δ1 γδ T cell.

In another aspect, the present invention provides a plurality of any one of the foregoing, e.g., γδ, T cells, or a plurality of, e.g., γδ, T cells as described herein. In some embodiments, the plurality comprises at least about $10^8$, e.g., γδ, T cells, preferably from about $10^8$, e.g., γδ, T cells to about $10^{11}$, e.g., γδ, T cells. In some embodiments, the the plurality comprises a composition that is at least 60%, 80%, or from about 60% or 80% to about 90% or 95% δ1, δ2, δ3, or δ4 γδ T cells, preferably δ1 or δ2 γδ T cells, more preferably δ2⁻ γδ T cells, most preferably δ1 γδ T cells.

In some embodiments, the present invention provides a method of making an, e.g., γδ, T cell as described herein, or a plurality of, e.g., γδ, T cells as described herein, wherein the method comprises transfecting the T cell(s) with a construct comprising an isolated nucleic acid sequence as described herein. In some cases, the method comprises, e.g., gamma, retroviral transduction. In some cases, the method comprises ex vivo expansion of the T cell(s), wherein the ex vivo expansion is performed before transfection and/or after transfection of the isolated nucleic acid sequence. In some cases, the method comprises ex vivo expansion of the T cell(s), wherein the ex vivo expansion is performed before transfection and after transfection of the isolated nucleic acid sequence. In some cases, the method comprises ex vivo expansion of the T cell(s), wherein the ex vivo expansion is performed after transfection of the isolated nucleic acid sequence. In some embodiments, the method comprises producing the from about $10^8$, e.g., γδ, T cells to about $10^{11}$, e.g., γδ, T cells that functionally express a CAR described herein within about 30 days of transfection.

In another aspect, the present invention provides a pharmaceutical composition comprising a pharmaceutically acceptable excipient and an, e.g., γδ, T cell described herein.

In another aspect, the present invention provides a method of killing a hematological tumor cell, the method comprising contacting the hematological tumor cell with a tumor cell killing effective amount of an, e.g., γδ, T cell, plurality of such cells, and/or pharmaceutical composition comprising such cells as described herein. In some embodiments, the method comprises introducing a therapeutically effective amount of the, e.g., γδ, T cell(s) or the pharmaceutical composition into a host organism comprising the hematological tumor cell. In some embodiments, the method comprises introducing into a host organism comprising the hematological tumor cell a therapeutically effective amount of the, e.g., γδ, T cell(s) or the pharmaceutical composition and simultaneously or sequentially administering one or more methods to elevate common gamma chain cytokine(s).

In some embodiments, the administering one or more methods to elevate common gamma chain cytokine(s) comprises administering simultaneously with introducing the, e.g., γδ, T cell(s) or sequentially an amount of common gamma chain cytokine(s) effective to increase proliferation, cytotoxic activity, persistence, or the combination thereof of the introduced, e.g., γδ, T cell(s), preferably wherein the method comprises administering IL-2, more preferably wherein the method comprises administering IL-15. In some embodiments, the one or more methods to elevate common gamma chain cytokine(s) comprise administering an amount of common gamma chain cytokine(s) effective to increase proliferation, cytotoxic activity, persistence, or the combination thereof of the introduced T cell(s) before and/or after introducing the T cell(s). In some embodiments, the one or more methods to elevate common gamma chain cytokine(s) comprises lymphodepletion before introducing the T cell(s).

In some embodiments, the one or more methods to elevate common gamma chain cytokine(s) comprises secretion of one or more common gamma chain cytokine(s) from the introduced T cell(s). In some embodiments, the method reduces the in vivo tumor burden in the host organism, and/or increases the mean survival time of the host organism as compared to a control organism, wherein the control organism is not treated with the T cell(s) or the pharmaceutical composition. In some embodiments, the method is a method of treating cancer in a subject in need thereof. In some embodiments, the present invention provides an, e.g., γδ, T cell, plurality of, e.g., γδ, T cell(s), or a pharmaceutical composition described herein for use in treating a hematological tumor cell in a subject in need thereof.

In one aspect, the present invention provides a method of treating cancer by administering a therapeutically effective amount of γδ T cells, wherein the cancer comprises hematological tumor cells that exhibit cell surface expression of CD20; or administering a therapeutically effective amount of γδ T cells, wherein the cancer comprises hematological tumor cells that exhibit cell surface expression of BCMA. In some embodiments, the method comprises simultaneously with the administering of γδ T cells or sequentially, administering one or more methods to elevate common gamma chain cytokine(s). In some embodiments, the method comprises performing a plurality of administrations of the γδ T cells, wherein the interval between the plurality of administrations is at least about a week, preferably at least about 2, 3, 4, 5, 6, 7, 8, or 12 weeks, and/or no more than once every 6 or 12 months. In some embodiments, the present invention provides a pharmaceutical composition for use in any one of the foregoing methods of treatment.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 2 illustrate sequences of binding domains that specifically bind to an epitope within CD20. FIG. 2 discloses SEQ ID NOS 335-363, 99, 364, 107, and 365-368, respectively, in order of appearance.

FIG. 6 illustrates cytotoxicity of engineered CAR γδ T cells described herein against Raji cells. Top: Binding domains containing CDRs of 3H7 are tested. Bottom. cytotoxicity against Raji cells of γδ T cell s expressing a CAR containing a 3H7 binding domain, a CD3ζ signaling domain, and various costimulation endodomains as indicated a is demonstrated. The 3H7-CD27z CAR has a 3H7 binding domain, CD8α hinge and transmembrane domain, CD27 costimulation endodomain, and CD3ζ signaling domain. 3H7-5.1 has a 3H7 binding domain, a CD8α hinge and transmembrane domain, a 4-1BB costimulation endodomain, and a CD3ζ signaling domain.

Figure 13:
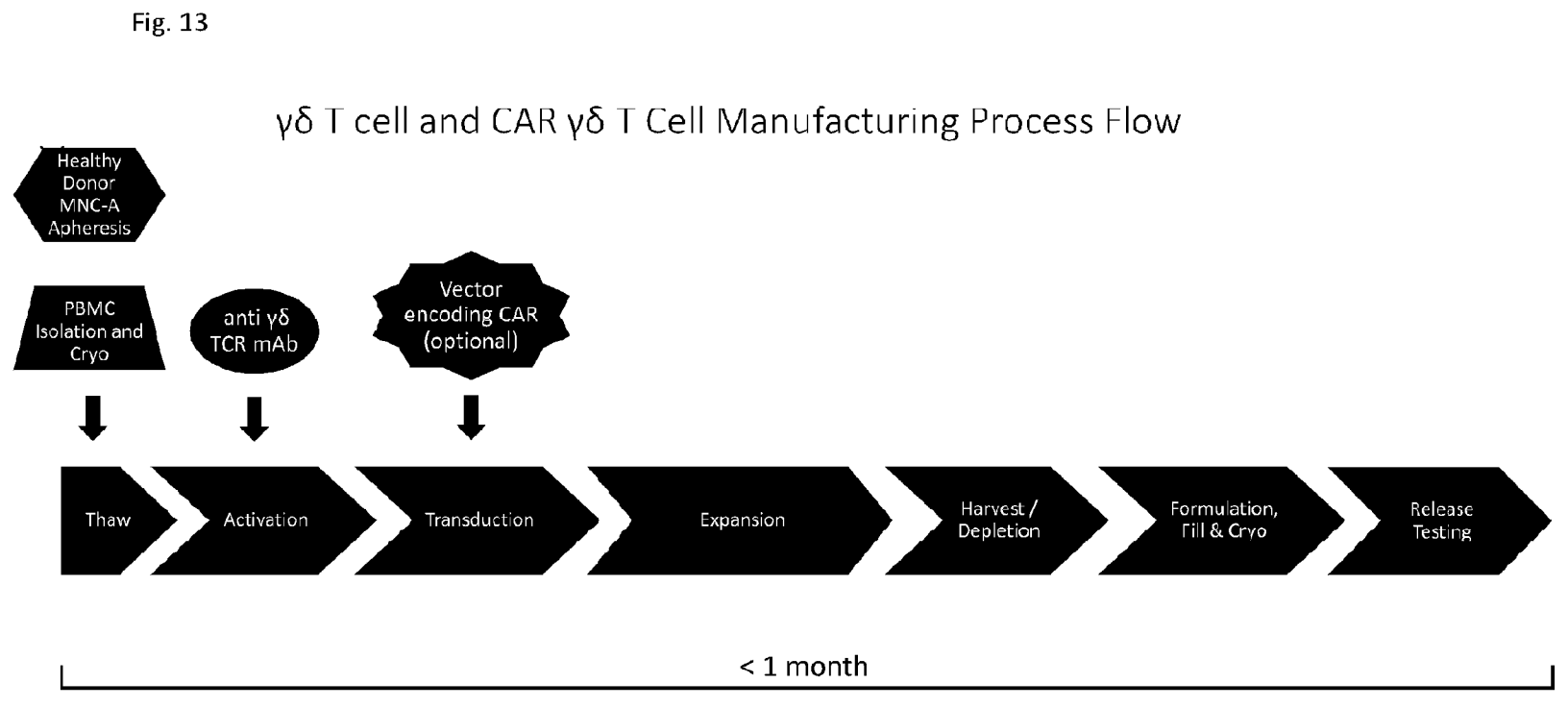

FIG. 13 illustrates a manufacturing process for production of engineered γδ CAR-T cells and non-engineered γδ CAR-T cells.

FIG. 17 illustrates cytotoxic activity of Vδ1 T cells transduced with various anti-BCMA CAR constructs against a panel of multiple myeloma and Burkitt lymphoma BCMA+ cell lines.

DETAILED DESCRIPTION

Definitions

Figure 1:
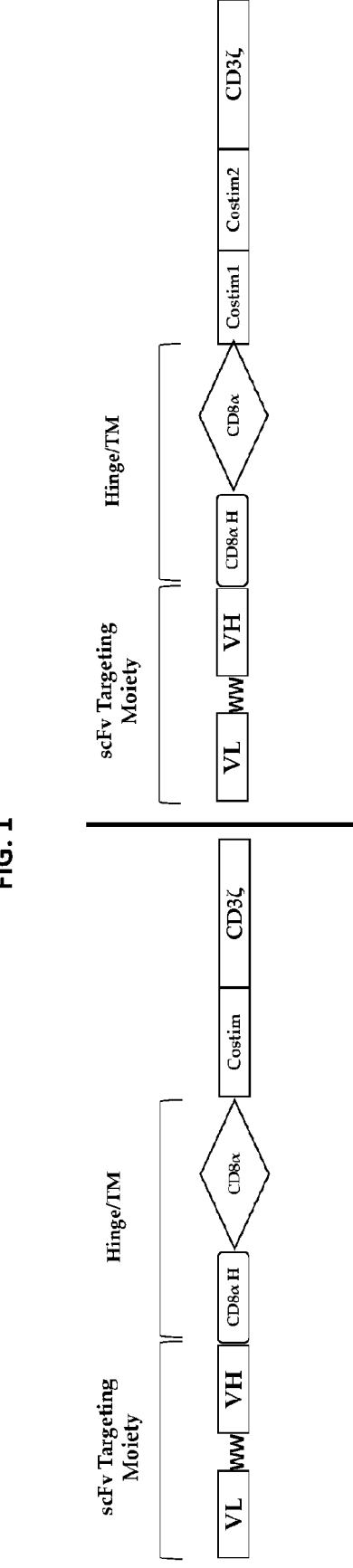
FIG. 1 is a schematic illustration of an embodiment of a chimeric antigen receptor (CAR) containing one costimulatory signaling endodomain (left) or two costimulatory signaling endodomains (right). As used herein costimulatory signaling endodomains are also referred to as costimulation endodomains or costimulatory endodomains. Exemplary costimulatory signaling endodomains useful in exemplary CARs include, without limitation, CD28; CD137 (41BB); CD278 (ICOS); CD27; CD134 (OX40); TLR2, and combinations thereof.

For purposes of interpreting this specification, the following definitions will apply, and whenever appropriate, terms used in the singular will also include the plural and vice versa. In the event that any definition set forth conflicts with any document incorporated herein by reference, the definition set forth below shall control. Unless defined otherwise, all technical and scientific terms used herein have the same meaning as commonly understood by one of ordinary skill in the art to which the invention pertains.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "γδ T-cells (gamma delta T-cells)" as used herein refers to a subset of T-cells that express a distinct T-cell receptor (TCR), namely γδTCR, on their surface, composed of one γ-chain and one δ-chain. The term "γδ T-cells" specifically includes all subsets of γδ T-cells, including, without limitation, Vδ1 and Vδ2, Vδ3 γδ T cells, as well as naïve, effector memory, central memory, and terminally differentiated γδ T-cells. As a further example, the term "γδ T-cells" includes Vδ4, Vδ5, Vδ7, and Vδ8 γδ T cells, as well as Vγ2, Vγ3, Vγ5, Vγ8, Vγ9, Vγ10, and Vγ11 γδ T cells. In some embodiments, the γδ T-cells are Vδ1⁻, Vδ2⁻, or Vδ1⁻ and Vδ2⁻. Compositions and methods for making and using engineered and non-engineered γδ T cells and/or sub-types thereof include, without limitation, those described in US 2016/0175358; WO 2017/197347; U.S. Pat. No. 9,499,788; US 2018/0169147; U.S. Pat. No. 9,907,820; US 2018/0125889 and US 2017/0196910, the contents of each of which are incorporated by reference for all purposes, including the said compositions and methods for making and using engineered and non-engineered γδ T cells and/or sub-types thereof. The present application further contemplates T cells, or other engineered leukocytes or lymphocytes, that express one γ-chain or one δ-chain, optionally in combination with a second polypeptide to form a functional TCR. Such engineered leukocytes or lymphocytes, that express one γ-chain or one δ-chain may be used in the methods or present in the compositions described herein.

As used herein, the term "T lymphocyte" or "T cell" refers to an immune cell that expresses or has expressed CD3 (CD3+) and a T Cell Receptor (TCR+). T cells play a central role in cell-mediated immunity. A T cell that "has expressed" CD3 and a TCR has been engineered to eliminate CD3 and/or TCR cell surface expression.

As used herein, the term "TCR" or "T cell receptor" refers to a dimeric heterologous cell surface signaling protein forming an alpha-beta or gamma-delta receptor or combinations thereof αβTCRs recognize an antigen presented by an MHC molecule, whereas γδTCR can recognize an antigen independently of MHC presentation.

The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in antibody molecules in their naturally occurring conformations.

An "antibody light chain," as used herein, refers to the smaller of the two types of polypeptide chains present in antibody molecules in their naturally occurring conformations. K and k light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including proteins or peptides, can serve as an antigen. Furthermore, antigens can be derived from recombinant or genomic DNA. A skilled artisan will understand that any DNA that comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated, synthesized, or can be derived from a biological sample. Such a biological sample can include, but is not limited to a tissue sample, a tumor sample, a cell or a biological fluid.

The term "epitope" includes any protein determinant, lipid or carbohydrate determinant capable of specific binding to an immunoglobulin or T-cell receptor. Epitopic determinants usually consist of active surface groupings of molecules such as amino acids, lipids or sugar side chains and usually have specific three-dimensional structural characteristics, as well as specific charge characteristics. An antibody is said to specifically bind an antigen when the equilibrium dissociation constant ($K_D$) is in the range of $10^{-6}$-$10^{-12}$ M.

Antibodies 3B9, 9C11, 3H7, 2B7, and 10F2 represent exemplary embodiments of antibodies that specifically recognize CD20. These antibodies, fragments thereof, and their complementary determining regions, are also described in U.S. 2009/0035322, where they are referred to as 3B9-10, 9C11-14, 3H7-6, 2B7-7, and 10F2-13 respectively. As described herein, these antibodies, fragments thereof, and their complementary determining regions, are useful in generating anti-CD20 chimeric antigen receptor (CAR) constructs and engineering and using CAR-T cells for treating hematological tumors that express CD20.

Binding domains 21587N, 16747P, 16711P, and 16716P represent exemplary embodiments of binding domains that specifically recognize BCMA. These antibodies, fragments thereof, and their complementary determining regions, are also described in U.S. Ser. No. 16/516,028, filed Jul. 18, 2019, the contents of which are incorporated by reference in the entirety and for all purposes and in particular for the binding domains, antibodies, antibody fragments, complementarity determining regions, polypeptides containing said complementarity determining regions, nucleic acids encoding for said complementarity determining regions, and epitope specificities and assays for determining epitope specificity described therein. In some cases, 21587N, 16747P, 16711P, and 16716P are referred to as H2aM21587N, H1H16747P, H1H16711P, H1H16716P respectively. As described herein, these antibodies, fragments thereof, and their complementary determining regions, are useful in generating anti-BCMA chimeric antigen receptor (CAR) constructs and engineering and using CAR-T cells for treating hematological tumors that express BCMA.

The term "chimeric antigen receptors (CARs)," as used herein, may refer to artificial T-cell receptors, T-bodies, single-chain immunoreceptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain (allowing the T cell to activate upon engagement of targeting moiety with target cell, such as a target tumor cell), a transmembrane domain, and an extracellular domain that may vary in length and comprises a disease- or disorder-associated, e.g., a tumor-antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP 10/12, and/or OX40, ICOS, TLRs (e.g., TLR2), etc. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors. Furthermore, one skilled in the art will understand that a costimulatory domain need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, the term "autologous" is meant to refer to any material derived from an individual which is later to be re-introduced into the same individual.

As used herein, the term "allogeneic" refers to material derived from an animal which is later introduced into a different animal of the same species.

The term "therapeutically effective amount" refers to the amount of a composition that will elicit a biological or medical response of a tissue, system, or subject that is being sought by the researcher, veterinarian, medical doctor or other clinician. The term "therapeutically effective amount" includes that amount of a composition that, when administered, is sufficient to prevent development of, or alleviate to some extent, one or more of the signs or symptoms of the disorder or disease (e.g., hematological cancer) being treated. The therapeutically effective amount will vary depending on the composition, the disease and its severity and the age, weight, etc., of the subject to be treated.

To "treat" a disease as the term is used herein, means to reduce the frequency or severity of at least one sign or symptom of a disease or disorder experienced by a subject.

Administration "in combination with" one or more further therapeutic agents includes simultaneous (concurrent) and sequential administration in any order.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The terms "patient," "subject," "individual," and the like are used interchangeably herein, and refer to any animal, amenable to the methods described herein. In certain non-limiting embodiments, the patient, subject or individual is a human.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

In some embodiments, specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. Moreover, multi-specific antibodies that bind to a first antigen and one or more additional antigens or a bispecific antibody that binds to two different regions of an antigen are nonetheless considered antibodies that "specifically bind," as used herein.

Hematologic cancers are cancers originating in the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In a preferred embodiment, the hematological cancer expresses, or over-expresses, CD20. In a preferred embodiment, the hematological cancer expresses, or over-expresses, B cell maturation antigen (BCMA), also known as tumor necrosis factor receptor superfamily member 17 (TNFRSF17).

"Expression cassette" refers to a nucleic acid comprising expression control sequences operatively linked to a nucleic acid encoding a transcript or polypeptide to be expressed. An expression cassette comprises sufficient cis-acting elements for expression; other elements for expression can be supplied by the host cell or in an in vitro expression system. Expression cassettes can be a component of a vector such as a cosmid, a plasmid (e.g., naked or contained in a liposome), or a virus (e.g., lentivirus, retrovirus, adenovirus, and adeno-associated virus). An expression cassette can be in a host cell, such as a γδ T cell.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Chimeric Antigen Receptor Constructs:

Aspects of the invention include nucleic acids encoding CARs, and constructs and vectors containing such nucleic acids. In some cases, the nucleic acid is a, e.g., heterologous, component of an expression cassette. In some embodiments, the nucleic acid is a, e.g., heterologous, component of a retroviral vector. In some embodiments, the nucleic acid is a, e.g., heterologous, component of an αβ or γδ T cell, and preferably a γδ T cell. In some embodiments, the nucleic acid is a, e.g., heterologous, component of an γ+ T cell and/or a δ+ T cell. In some embodiments, the nucleic acid is a, e.g., heterologous, component of an α− T cell and/or a β− T cell.

Described herein are nucleic acids encoding a CAR binding domain that specifically binds to a tumor associated antigen (TAA) expressed on a surface of a hematological tumor cell. Exemplary TAAs include CD19, CD20, and BCMA. In some embodiments, the binding domain is a CD19 binding domain, such as a CD19 binding domain described in U.S. Pat. No. 9,540,445, the contents of which are incorporated by reference in the entirety and for all purposes and in particular for the binding domains, antibodies, antibody fragments, complementarity determining regions, polypeptides containing said complementarity determining regions, nucleic acids encoding for said complementarity determining regions, and epitope specificities and assays for determining epitope specificity described therein. In some embodiments, the binding domain is a CD20 binding domain, such as a CD20 binding domain described in U.S. Patent Appl. No. 2009/0035322, the contents of which are incorporated by reference in the entirety and for all purposes and in particular for the binding domains, antibodies, antibody fragments, complementarity determining regions, polypeptides containing said complementarity determining regions, nucleic acids encoding for said complementarity determining regions, and epitope specificities and assays for determining epitope specificity described therein. In some embodiments, the binding domain is a BCMA binding domain, such as a BCMA binding domain described in WO 2018/133877, or a BCMA binding domain described in U.S. Ser. No. 16/516,028, filed Jul. 18, 2019, the contents of each of which are incorporated by reference in the entirety and for all purposes and in particular for the binding domains, antibodies, antibody fragments, complementarity determining regions, polypeptides containing said complementarity determining regions, nucleic acids encoding for said complementarity determining regions, and epitope specificities and assays for determining epitope specificity described therein. Typically, the region encoding the binding domain is 5' of a linker region (e.g., a region encoding a CD8α hinge domain).

In some embodiments, the binding domain binds the antigen as expressed in a full-length functional polypeptide on the surface of a cell. In some embodiments, the binding domain binds the antigen as presented in an MHC:antigen complex. In some embodiments, the binding domain binds the antigen in an HLA-restricted manner. Binding domains exhibiting specificity for MHC:antigen complexes are described, e.g., in WO/2016/199140 and WO/2016/199141, the contents of each of which are incorporated by reference in the entirety and for all purposes and in particular for the binding domains, antibodies, antibody fragments, complementarity determining regions, polypeptides containing said complementarity determining regions, nucleic acids encoding for said complementarity determining regions, and epitope specificities and assays for determining epitope specificity described therein.

Exemplary CD20 binding domains include but are not limited to binding domains that selectively bind to an epitope within CD20 bound by, or that competes for binding with, 3B9, 3H7, 2B7, 9C11, or 10F2; or 3B9, 3H7, 2B7, or 9C11; or 3H7. Additionally or alternatively, the CD20 binding domain can comprise the complementary determining regions of an anti-CD20 antibody selected from the group consisting of 3B9, 3H7, 2B7, 9C11, and 10F2; selected from the group consisting of 3B9, 3H7, 2B7, and 9C11; or comprise the complementary determining regions of an anti-CD20 antibody selected from the group consisting of 3H7. The present disclosure also contemplates CD20, CD19, and BCMA binding domains that compete for binding with a sequence provided herein.

One can determine whether a CD20 binding domain binds to the same epitope as, or competes for binding with, a reference antibody or binding domain by using known methods. For example, to determine if a test antibody binds to the same epitope as a reference binding domain, the reference binding domain can be allowed to bind to CD20 under saturating conditions. Next, the ability of a test binding domain to bind to CD20 molecule can be assessed. If the test binding domain is able to bind to CD20 following saturation binding with the reference binding domain, it can be concluded that the test binding domain binds to a different epitope than the reference binding domain. On the other hand, if the test binding domain is not able to bind to CD20 following saturation binding with the reference binding domain, then the test binding domain may bind to the same epitope as the epitope bound by the reference binding domain.

To determine if a binding domain competes for binding with a reference binding domain, the above-described binding methodology is performed in two orientations: In a first orientation, the reference binding domain is allowed to bind to CD20 under saturating conditions followed by assessment of binding of the test binding domain to the CD20 molecule. In a second orientation, the test binding domain is allowed to bind to a CD20 molecule under saturating conditions followed by assessment of binding of the reference binding domain to the CD20 molecule. If, in both orientations, only the first (saturating) binding domain is capable of binding to the CD20 molecule, then it is concluded that the test binding domain and the reference binding domain compete for binding to CD20. As will be appreciated by a person of ordinary skill in the art, a binding domain that competes for binding with a reference binding domain may not necessarily bind to the identical epitope as the reference binding domain, but may sterically block binding of the reference binding domain by binding an overlapping or adjacent epitope. The methods described above to determine competition and epitope binding with an anti-CD20 binding domain can likewise be applied to anti-CD19 binding domains and anti-BCMA binding domains.

Two binding domains bind to the same or overlapping epitope if each competitively inhibits (blocks) binding of the other to the antigen. That is, a 1-, 5-, 10-, 20- or 100-fold excess of one binding domain inhibits binding of the other by at least 50%, for example, 75%, 90% or even 99% as measured in a competitive binding assay (see, e.g., Junghans et al., Cancer Res. 1990 50:1495-1502). Alternatively, two binding domains have the same epitope if essentially all amino acid mutations in the antigen that reduce or eliminate binding of one binding domain reduce or eliminate binding of the other. Two binding domains have overlapping epitopes if some amino acid mutations that reduce or eliminate binding of one binding domain reduce or eliminate binding of the other.

Additional routine experimentation (e.g., peptide mutation and binding analyses) can then be carried out to confirm whether the observed lack of binding of the test binding domain is in fact due to binding to the same epitope as the reference binding domain or if steric blocking (or another phenomenon) is responsible for the lack of observed binding. Experiments of this sort can be performed using ELISA, RIA, surface plasmon resonance, flow cytometry or any other quantitative or qualitative binding assay available in the art.

The present disclosure provides antibodies and CARs with "substantial identity" or "substantial similarity" to the sequences provided herein in the CDR or framework regions. The term "substantial identity" or "substantially identical," when referring to a nucleic acid or fragment thereof, indicates that, when optimally aligned with another nucleic acid (or the complementary strand of the other nucleic acid), there is nucleotide sequence identity in %, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity. In some aspects, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenyl-alanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence identity and/or similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence disclosed herein to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

Provided herein are anti-CD20, anti-BCMA, or anti-CD19 CARs comprising variants of any of the HCVR, LCVR, and/or CDR amino acid sequences disclosed herein having one or more substitutions (e.g., conservative substitutions). For example, the present disclosure includes anti-CD20 CARs having HCVR, LCVR, and/or CDR amino acid sequences with, e.g., 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 amino acid substitutions relative to any of the HCVR, LCVR, and/or CDR (e.g., HCDR1, HCDR2, HCDR3, LCDR1, LCDR2, or LCDR3) amino acid sequences disclosed herein. For example, an anti-CD20 CAR can comprise 20, 19, 18, 17, 16, 15, 14 13, 12, 11, 10, 9, 8, 7, 6, 5, 4, 3, 2, or 1 amino acid substitutions (e.g., conservative amino acid substitutions) relative to any of the HCVR, LCVR, and/or CDR (e.g., HCDR1, HCDR2, HCDR3, LCDR1, LCDR2, or LCDR3) amino acid sequences disclosed herein.

Similarly, the present disclosure includes anti-BCMA CARs having HCVR, LCVR, and/or CDR amino acid sequences with, e.g., 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 amino acid substitutions relative to any of the HCVR, LCVR, and/or CDR (e.g., HCDR1, HCDR2, HCDR3, LCDR1, LCDR2, or LCDR3) amino acid sequences disclosed herein. For example, an anti-BCMA CAR can comprise 20, 19, 18, 17, 16, 15, 14 13, 12, 11, 10, 9, 8, 7, 6, 5, 4, 3, 2, or 1 amino acid substitutions (e.g., conservative amino acid substitutions) relative to any of the HCVR, LCVR, and/or CDR (e.g., HCDR1, HCDR2, HCDR3, LCDR1, LCDR2, or LCDR3) amino acid sequences disclosed herein.

In some embodiments, the isolated nucleic acid encodes an anti-CD20 binding domain having a heavy chain complementary determining region 3 (HCDR3) and a light chain CDR3 (LCDR3), wherein the HCDR3 and LCDR3 are selected from the group consisting of SEQ ID NO:345 (AKDPSYGSGSYHSYYGMDV) and 353 (QQRFNWPLT); 201 (VKDFHYGSGSNYGMDV) and 209 (QQSNDWPLT); and 249 (TKDGSYGHFYSGLDV) and 257 (QQRYYWPLT).

In some embodiments, the isolated nucleic acid encodes an anti-CD20 binding domain having a heavy chain variable region (HCVR) sequence and a light chain variable region (LCVR) sequence, wherein the HCVR and LCVR sequences are selected from the group consisting of SEQ ID NO: 339 (EEQLVESGGDLVQPGRSLRLS-CAASGFTFHDYTMH WVRQAPGKGLEWVS-GISWNSGSLGYADSVKGRFTISRD-NAKKSLYLQMNSLRAEDTAL YYCAKDPSYGSGSYHSYYGMDVWGQGTTVTVSS) and 347 (EIVLTQSPATLSLSPGE RATLSCWASQSIS-RYLVWYQQKCGQAPRLLIYEASKRAT-GIPVRFSGSGSGTDFTLTISSL ESED-FAVYYCQQRFNWPLTFGGGTKVEIK); 195 (EVQLAESGGDLVQSGRSLRLSCAAS GITFHDYAM-HWVRQPPGKGLEWVSGISWNSDYIG-YADSVKGRFTISRDNAKKSLYLQM NSLRPDD-TALYYCVKDFHYGSGSNYGMDVWGQGTTVTVSP) and 203 (EIVMTQSPATL SMSPGER-ATLSCRASQSVSRNLAWYQQKVGQAPRLLISGAS-TRATGIPARFSGSGSGTEF TLTINSLQSED-FAVYYCQQSNDWPLTFGQGTRLEIK); and 243 (EVQLVESGGGLVQPGR SLRLSCAASGFTFYDYAM-HWVRQAPGKGLEWVSGISWNSDTIG-YADSVKGRFTISRDN AKNSLYLQMNSLRAED-TALYYCTKDGSYGHFYSGLDVWGQGTTVTVSS) and 251 (EIVLTQSPATLSLSPGERATLSCRASQSVSSY-LAWYQQKPGQAPRLLIYVASNRATGIPA RFSGSGSGTDFTLTISSLEPDD-FAVYYCQQRYYWPLTFGGGTKVEIK).

In some embodiments, the isolated nucleic acid encodes an anti-CD20 binding domain having a heavy chain complementary determining region 3 (HCDR3) domain and a light chain CDR3 (LCDR3) domain, wherein the HCDR3 domain comprises an amino acid sequence of the formula X1-X2-X3-X4-X5-X6-X7-X8-X9-X10-X11-X12-X13-X14-X15-X16-X17-X18-X19, wherein X1=A, V or T; X2=K; X3=D; X4=P, F or G; X5=S or H; X6=Y; X7=G; X8=S or H; X9=G or F; X10=S or Y; X11=Y, N or S; X12=Y, G or H; X13=G, L or S; X14=Y, M or D; X15=Y, D or V; X16=G, V or absent; X17=M or absent; X18=D or absent; X19=V or absent (SEQ ID NO: 369); and the LCDR3 domain comprises an amino acid sequence of the formula X1-X2-X3-X4-X5-X6-X7-X8-X9, wherein X1=Q; X2=Q; X3=R or S; X4=N, Y or F; X5=N, D, or Y; X6=W; X7=P; X8=L; X9=T (SEQ ID NO: 370).

In some embodiments, the isolated nucleic acid encodes an anti-CD20 binding domain having a heavy chain variable region (HCVR) sequence and a light chain variable region (LCVR) sequence, wherein the HCVR and LCVR sequences are SEQ ID NO: 99 (EVQLVESGG-GLVQPGRSLRLSCAASGFTFYDYAMHWVRQAPGK- GLEWVSGISWNSGY IGYADSVKGRFTISRDNAKNS-
LYLQMNSLRAEDTALYYCAKDNSYGKFYYGLDVWGQ
GTTVTVSS) and 107 (EIVMTQSPATLSVSPGERT-
TLSCRASQSVSSNLAWYLQKPGQAPR LLIYGAS-
TRATGIPARFSGSGSGTEFILTISSLQSED-
FAVYYCQQYNNWPITFGQGTRLEIK).

In some embodiments, the isolated nucleic acid encodes an anti-CD20 binding domain that binds the same epitope as, competes with, or is an anti-CD20 binding domain having heavy chain complementarity determining regions (HCDR) and a light chain complementarity determining regions (LCDR), wherein the HCDR and LCDR sequences are the HCDR sequences of SEQ ID NO:99 and the LCDR sequences of SEQ ID NO: 107 respectively.

In some embodiments, the isolated nucleic acid encodes an anti-CD20 binding domain that binds the same epitope as, competes with, or is an anti-CD20 binding domain having an HCDR1 that is or comprises SEQ ID NO: 101 (GFTFYDYA), an HCDR2 that is or comprises SEQ ID NO: 103 (ISWNSGYI), and/or an HCDR3 that is or comprises SEQ ID NO: 105 (AKDNSYGKFYYGLDV). In some embodiments, the isolated nucleic acid encodes an anti-CD20 binding domain that binds the same epitope as, competes with, or is an anti-CD20 binding domain having an LCDR1 that is or comprises SEQ ID NO: 109 (QSVSSN), an LCDR2 that is or comprises SEQ ID NO: 111 (GAS), and/or an LCDR3 that is or comprises SEQ ID NO: 113 (QQYNNWPIT). In some embodiments, the isolated nucleic acid encodes an anti-CD20 binding domain that binds the same epitope as, competes with, or is an anti-CD20 binding domain having an HCDR1 that is or comprises SEQ ID NO:101, an HCDR2 that is or comprises SEQ ID NO:103, an HCDR3 that is or comprises SEQ ID NO: 105, an LCDR1 that is or comprises SEQ ID NO: 109, an LCDR2 that is or comprises SEQ ID NO: 111, and an LCDR3 that is or comprises SEQ ID NO: 113. In some embodiments, the isolated nucleic acid encodes an anti-CD20 binding domain having an HCDR1 comprising SEQ ID NO:101, an HCDR2 comprising SEQ ID NO:103, an HCDR3 comprising SEQ ID NO: 105, an LCDR1 comprising SEQ ID NO: 109, an LCDR2 comprising SEQ ID NO: 111, and an LCDR3 comprising SEQ ID NO: 113.

Exemplary BCMA binding domains include but are not limited to binding domains that selectively bind to an epitope within BCMA bound by, or that competes for binding with a BCMA binding domain described in WO 2018/133877, or a BCMA binding domain described in U.S. Ser. No. 16/516,028, filed Jul. 18, 2019. Additionally or alternatively, the BCMA binding domain can comprise the complementary determining regions of an anti-BCMA anti-body selected from the group consisting of an anti-BCMA antibody or chimeric antigen receptor described in WO 2018/133877, and an anti-BCMA antibody or chimeric antigen receptor described in U.S. Ser. No. 16/516,028, filed Jul. 18, 2019.

Exemplary BMCA binding domains include but are not limited to binding domains that selectively bind to an epitope within BCMA bound by, or that competes for binding with, anti-BCMA-CAR 16716P, anti-BCMA-CAR 16747P, and/or anti-BCMA-CAR 21587N. Additionally or alternatively, the BCMA binding domain can comprise the complementary determining regions of an anti-BCMA CAR selected from the group consisting of anti-BCMA-CAR 16716P, anti-BCMA-CAR 16747P, and anti-BCMA-CAR 21587N.

In some embodiments, the isolated nucleic acid encodes an anti-BCMA binding domain having a heavy chain complementary determining region 3 (HCDR3) and a light chain CDR3 (LCDR3), wherein the HCDR3 and LCDR3 are selected from the group consisting of SEQ ID NO:21 (RAGDNWNWFDP) and SEQ ID NO:22 (QQAKSVPFT); SEQ ID NO:23 (EGGNYGMDV) and SEQ ID NO:24 (QQANSFPPT); and SEQ ID NO:25 (FAEYCGGNI-CYYYGMDV) and SEQ ID NO:26 (QQCGGSPWT).

In some embodiments, the isolated nucleic acid encodes an anti-BCMA binding domain having a heavy chain variable region (HCVR) sequence and a light chain variable region (LCVR) sequence, wherein the HCVR and LCVR sequences are selected from the group consisting of 16716P binding domain HCVR SEQ ID NO: 27 (MSVPTQVLGLLLLWLTDARCEVQLVESGG-GLVQPGGSLRLSCAASGFTFSSYVMSWV RQAPGK-GLEWVSAIIGSGGGSTYYADSVKGRFTISRDNSKNT-LYLQMNSLRAEDTAVYYC AKRAGDNWNWFDPWGQGTLVTV) and 16716P binding domain LCVR SEQ ID NO: 28 (DIQMTQSPSSVSASLGDRVTITCRASQGISS-WLAWYQRKPGKAPKLLIYAASSLQSGVPS RFSGSGSGADFTLTISSLQPEDFA-TYYCQQAKSVPFTFGPGTKVDIK); 16747P binding domain HCVR SEQ ID NO: 29 (MSVPTQVLGLLLLWLT-DARCQVQLVESGGGLV KPGGSLRLS-CAASGFTFSDYYISWIRQAPGKGLEWVSYIS-SSGSSIKYADSVKGRFTISRD NAKNSLYLQMNSLRAEDTAVYYCAREGG-NYGMDVWGQGTTVTV) and 16747P binding domain LCVR SEQ ID NO: 30 (DIQMTQSPSSVSASVGDRVTIT-CRASQGINNW LVWYQQKPGKAPKLLIYAAT-SLQSGVPSRFSGSGSGTDFTLTISSLQPEDFA-TYYCQQAN SFPPTFGQGTKLEIK); and 21587N binding domain HCVR SEQ ID NO: 31 (MSVPTQVLGLLLLWLT-DARCQVQLQESGPGLVKPSETLSLTCTVSGGS-INYYYWNWIR QPPGKGLEWIGYISYS-GNTNYNPSLKSRVTISVATSRNQFSLTLS SVTAADTAVYYCARF AEYCGGNI-CYYYGMDVWGQGTTVTV) and 21587N binding domain LCVR SEQ ID NO:32 (EIVLTQSPGTLSLSPGER-ATFSCRASQSVGSSFLAWYQQKPGQAPRRLMY-GASNRATGI PDRFSGSGSGTDFTLTISRLEPED-FAVYYCQQCGGSPWTFGQGTKVEIK).

Provided herein are anti-BCMA CARs comprising variants of any of the HCVR, LCVR, and/or CDR amino acid sequences disclosed herein having one or more substitutions (e.g., conservative substitutions). For example, the present disclosure includes anti-BCMA CARs having HCVR, LCVR, and/or CDR amino acid sequences with, e.g., 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 amino acid substitutions relative to any of the HCVR, LCVR, and/or CDR (e.g., HCDR1, HCDR2, HCDR3, LCDR1, LCDR2, or LCDR3) amino acid sequences disclosed herein. For example, an anti-BCMA CAR can comprise 20, 19, 18, 17, 16, 15, 14 13, 12, 11, 10, 9, 8, 7, 6, 5, 4, 3, 2, or 1 amino acid substitutions (e.g., conservative amino acid substitutions) relative to any of the HCVR, LCVR, and/or CDR (e.g., HCDR1, HCDR2, HCDR3, LCDR1, LCDR2, or LCDR3) amino acid sequences disclosed herein.

Exemplary binding domains described herein typically comprise, in order from the amino to carboxy terminus, a heavy chain region followed by a light chain region (VH-VL). Where a certain order of of VH and VL region in the binding domain is explicitly or implicitly described, the present disclosure is also understand to describe the alternate embodiment in which the order of VH and VL regions are reversed, e.g., in an scFV or a CAR comprising an scFv binding domain. Thus, description of a VH-VL order also describes the alternate VL-VH order, e.g., in an scFV or a CAR comprising an scFv binding domain. Moreover, description of a VL-VH order also describes the alternate VH-VL order, e.g., in an scFV or a CAR comprising an scFv binding domain.

Generally, the CAR encoding nucleic acids described herein include an extracellular linker portion that encodes a peptide linker that links the binding domain to a transmembrane domain. Exemplary linker portions include, without limitation, a linker portion that encodes the CD8α hinge domain, e.g., SEQ ID NO:1 (PTPAPTIASQPLSLRPEACR-PAAGGAVHTRGLDFACDIY) or SEQ ID NO:2 (TTTPA-PRP PTPAPTIASQPLSLRPEACRPAAGGAVHTRGLD-FACDIY). Typically, the region encoding the peptide linker (e.g., CD8α hinge domain) is 3' of the region encoding the binding domain and 5' of a region encoding a transmembrane domain.

The CAR encoding nucleic acids described herein include a transmembrane domain. The transmembrane domain can link an extracellular antigen binding domain, e.g., and hinge, to one or more intracellular signaling components. For example, the transmembrane domain can link an antigen binding domain, e.g., and hinge, to a CD3ζ signaling domain and optionally with one or two costimulation endodomains. Exemplary transmembrane domains include without limitation a CD8α transmembrane domain, e.g., SEQ ID NO:3 (IWAPLAGTCGVLLLSLVITLYC). Typically, the region encoding the transmembrane domain (e.g., CD8α transmembrane domain) is 3' of the region encoding the peptide linker (e.g., CD8α hinge domain) and 5' of a region encoding one or more cytoplasmic domains.

In some embodiments, the isolated nucleic acid encodes a cytoplasmic region containing one or more cytoplasmic domains. The region encoding the cytoplasmic region is typically 3' of the region encoding the transmembrane domain. The cytoplasmic domains are typically signaling domains that provide an activating signal for γδ T cell proliferation, cytotoxic activity, and/or pro-inflammatory cytokine expression (e.g., TNF-α or IFNγ). An exemplary cytoplasmic domain is a CD3ζ signaling domain. In some embodiments, the CD3ζ signaling domain is or comprises SEQ ID NO:4 (RVKFSRSADAPAYQQGQNQLY-NELNLGR REEYDVLDKRR-GRDPEMGGKPQRRKNPQEGLYNELQKDKMAEAY-SEIGMKGERRRGK GHDGLYQGLSTATKDTYDALHMQALPPR). In some embodiments, the CD3ζ signaling domain is or comprises SEQ ID NO:5 (RVKFSRSADAPAYQQGQNQLYNELNL-GRREEYDV LDKRRGRDPEMGGKPRRKNPQEGLY-NELQKDKMAEAYSEIGMKGERRRGKGHDGLY QGL-STATKDTYDALHMQALPPR). In some embodiments, the cytoplasmic region contains multiple (e.g., 2, 3, 4, 5, or 6) signaling domains, such as multiple (e.g., 2, 3, 4, 5, or 6) CD3ζ signaling domains, e.g., each independently selected from SEQ ID NO: 4 and 5. In some embodiments, the cytoplasmic region contains multiple (e.g., 2, 3, 4, 5, or 6) non-CD3ζ signaling domains and a CD3ζ signaling domain. In some embodiments, the cytoplasmic region contains a non-CD3ζ signaling domain and multiple (e.g., 2, 3, 4, 5, or 6) CD3ζ signaling domains.

The cytoplasmic region can contain one or more costimulation endodomains. A region encoding one or more costimulation endodomains can be 5' or 3' of a region encoding a signaling domain. In some embodiments, the region encoding one or more costimulation endodomains is 5' of the region encoding a signaling domain. In some embodiments, a region encoding one or more costimulation endodomains is 5' of a signaling domain and an additional region encoding one or more costimulation endodomains is 3' of the signaling domain. Exemplary costimulation endodomains include, without limitation, CD28; CD137 (4-1BB); CD278 (ICOS); CD27; CD134 (OX40); Dap10; Dap12; DNAm-1; 2B4; a SLAM domain; and TLR2 costimulation endodomains, and combinations thereof.

In some embodiments, the construct encodes at least one 4-1BB costimulation endodomain, and optionally a second costimulation endodomain selected from a 4-1BB, 2B4, ICOS, CD28, and CD27 costimulation endodomain. In some embodiments, the construct encodes at least two 4-1BB costimulation endodomains, or two 4-1BB costimulation endodomains in combination with one, two, three, or four, or more, costimulation endodomains selected from a 4-1BB, ICOS, CD28, and CD27. In some embodiments, the 4-1BB costimulation endodomain comprises SEQ ID NO: 6 (KR-GRKKLLYIFKQPFMRPVQTT QEEDGCSCRFPEEEEGGCEL).

In some embodiments, the construct encodes one CD27 costimulation endodomain, and optionally a second costimulation endodomain selected from a 4-1BB, ICOS, CD28, and CD27 costimulation endodomain. In some embodiments, the construct encodes a CD27 costimulation endodomain, and a 4-1BB costimulation endodomain. In some embodiments, the construct encodes two CD27 costimulation endodomains. In some embodiments, the CD27 costimulation endodomain comprises SEQ ID NO: 7 (QRRKYRSNKGESPVEPAEPCHYSCPREEEGSTIP-IQED YRKPEPACSP).

In some embodiments, the construct encodes a secretion signal, e.g., SEQ ID NO: 33 (MALPVTALLLPLALLL-HAARP) operably linked to facilitate secretion of a C-terminal polypeptide, such as a cytokine that supports the activation, cytotoxicity, and/or persistence of a T cell (e.g., CAR-T cell). In some embodiments, the construct encodes a secretion signal, e.g., SEQ ID NO: 33 operably linked to facilitate secretion of a common gamma chain cytokine such as IL-15 or an active fragment thereof, e.g., SEQ ID NO: 34 (NWVNVISDLKKIED LIQSMHIDATLYTESDVHP-SCKVTAMKCFLLELQVISLESGDASIHDTVEN-LIILANNSLSS NGNVTESGCKECEELEEKNIKE-FLQSFVHIVQMFINTS). Exemplary common gamma chain cytokines include IL-2 and IL-15. In some embodiments, the common gamma chain cytokine is selected from IL-2, IL-7, and IL-15. In some embodiments, the common gamma chain cytokine is IL-15. IL-15 sequences, including codon optimized nucleic acid sequences encoding sIL15, are disclosed herein and in WO 2007/037780.

In some embodiments, the construct encodes one or more multi-cistronic linker regions, e.g., between a signaling domain and/or costimulation endodomain and a secretion signal operably linked to facilitate secretion of a cytokine. A multi-cistronic linker region is a region of polypeptide sequence or RNA sequence that facilitates the production of multiple discrete polypeptides from a single transcription product. In some embodiments, the multi-cistronic linker region encodes a cleavage sequence. Suitable cleavage sequences include self-cleavage sequences such as a P2A, F2A, E2A, or T2A cleavage sequence and/or sequences that are cleaved by an endogenous protease, such as furin.

In some embodiments, the cleavage sequence is a P2A cleavage sequence. In some embodiments, the cleavage sequence is a furin cleavage sequence. In some embodiments, the cleavage sequences are a P2A and a furin cleavage sequence. In some embodiments, the cleavage sequence is the P2A cleavage sequence of SEQ ID NO: 43 (SGSGATNFSLLKQAGDVEENPGP). In some embodiments, the cleavage sequence is a furin cleavage sequence of SEQ ID NO: 44 (RAKR). In some embodiments, the cleavage sequence is a P2A+furin cleavage sequence of SEQ ID NO: 45 (RAKRSGSGATNFSLLKQAG DVEENPGP).

In some embodiments, the cleavage sequence is or comprises a P2A cleavage sequence of SEQ ID NO: 52 (ATNFSLLKQAGDVEENPGP). In some embodiments, the cleavage sequence is or comprises an F2A cleavage sequence of SEQ ID NO: 53 (VKQTLNNFDLLKLAGD-VESNPGP). In some embodiments, the cleavage sequence is or comprises an E2A cleavage sequence of SEQ ID NO: 54 (QCTNYALLKLAGDVESNPGP). In some embodiments, the cleavage sequence is or comprises an T2A cleavage sequence of SEQ ID NO: 55 (EGRSLLTCGD-VEENPGP). In certain aspects, multiple self-cleavage sequences can be encoded carboxy terminal to a signaling and/or costimulatory domain and amino-terminal to an encoded secreted cytokine (e.g., common gamma chain cytokine such as IL-15), preferably wherein the multiple self cleavage sequences are independently selected from the group consisting of a P2A cleavage sequence, a T2A cleavage sequence, an E2A cleavage sequence, and an F2A cleavage sequence. In certain aspects, one or more self-cleavage sequences and one or more sequences cleaved by an endogenous protease are encoded in a construct described herein. In certain embodiments, a endogenous protease recognition site is encoded amino terminal to a self cleavage sequence.

In some embodiments, the multi-cistronic linker region encodes an internal ribosome entry site. An exemplary internal ribosome entry site is encoded by SEQ ID NO: 56 (CTAACGTTACTGGCCGAAGCCGCTTG-GAATAAGGCCGGTGTGCGTTTGTCTATATGT TAT-TTTCCACCATATTGCCGTCTTTTGGCAATGT-GAGGGCCCGGAAACCTGGCCCTGT CTTCTTGACGAGCAT-TCCTAGGGGTCTTTCCCCTCTCGC-CAAAGGAATGCAAGGTCT GTTGAATGTCGT-GAAGGAAGCAGTTCCTCTGGAAGCTTC TTGAAGACAAACAACGTC TGTAGCGACCCTTTGCAGGCAGCGGAACCCCC-CACCTGGCGACAGGTGCCTCTGCG GCCAAAAGC-CACGTGTATAAGATA-CACCTGCAAAGGCGGCACAACCCCAGTGCCAC GTTGTGAGTTGGATAGTTGTGGAAAGAGT-CAAATGGCTCTCCTCAAGCGTATTCAAC AAGGGGCTGAAGGATGCCCAGAAGGTACCCAT-TGTATGGGATCTGATCTGGGGCC TCGGTGCA-CATGCTTTACATGTGTTTAGTCGAGGT-TAAAAAAACGTCTAGGCCCCCC GAACCACGGGGACGTGGTTTTCCTTT-GAAAAACACGATGATA).

Another exemplary internal ribosome entry site is encoded by SEQ ID NO: 60 (AGCAGGTTTCCC-CAACTGACACAAAACGTGCAACTT-GAAACTCCGCCTGGTCTTTC CAGGTCTAGAGGGGTAACACTTTGTACT GCGTTTGGCTCCACGCTCGATCCACTGGC GAGTGT-TAGTAACAGCACTGTTGCTTCGTAGCGGAG-CATGACGGCCGTGGGAACTCC TCCTTGGTAACAAGGACCCACGGGGCCAAAAGC-CACGCCCACACGGGCCCGTCATG TGTGCAACCCCAGCACGGCGACTT-TACTGCGAAACCCACTTTAAAGTGACATTGAAA CTGGTACCCACACACTGGTGACAGGCTAAGGATG CCCTTCAGGTACCCCGAGGTAA CACGCGACACTCGGGATCT-GAGAAGGGGACTGGGGCTTC-TATAAAAGCGCTCGGTT TAAAAAGCTTCTATGCCT-GAATAGGTGACCGGAGGTCGGCACCT TTCCTTTGCAATT ACTGACCAC).

Further suitable internal ribosome entry sites include, but are not limited to, those described in Nucleic Acids Res. 2010 January; 38 (Database issue):D131-6. doi: 10.1093/nar/gkp981. Epub 2009 Nov. 16, those described at iresit-e.org, those described in WO 2018/215787, the sequence described in GenBank accession No. KP019382.1, and the IRES element disclosed in GenBank accession No. LT727339.1.

Additional multi-cistronic linker regions, including cleavage self-cleavage, and IRES elements, are disclosed in US 2018/0360992 and U.S. Pat. No. 8,865,467.

In some embodiments, the isolated nucleic acid encodes SEQ ID NO:8 (MSVPTQVLGLLLLWLTDAR-CEIVMTQSPATLSVSPGERTTLSCRASQSVSSN-LAWYLQ KPGQAPRLLIYGASTRATGI-PARFSGSGSGTEFILTISSLQSEDFAVY YCQQYNNWPITFG QGTRLEIKGGGGSGGGGSGGG-GEVQLVESGGGLVQPGRSLRLSCAASGFTFYDYAMH WVRQAPGKGLEWVSGISWNSGYIG-YADSVKGRFTISRDNAKNSLYLQMNSLRAEDTAL YYCAKDNSYGKFYYGLDVWGQGTTVTVSSTTTPA-PRPPTPAPTIASQPLSLRPEACRPA AGGAVHTRGLD-FACDIYIWAPLAGTCGVLLLSLVIT-LYCQRRKYRSNKGESPVEPAEPC HYSCPREEEGSTIPIQEDYRKPEPACSPRVKFSRSADA-PAYQQGQNQLYNELNLGRREEY DVLDKRR-GRDPEMGGKPQRRKNPQEGLYNELQKDKMAEAY-SEIGMKGERRRGKGHD GLYQGLSTATKDTYDALHMQALPPR), a 3H7-CD8-CD27z polypeptide comprising the following domains in order: a 3H7 binding domain, a CD8α hinge and transmembrane domain, a CD27 costimulation endodomain, and a CD3ζ signaling domain.

In some embodiments, the isolated nucleic acid encodes SEQ ID NO: 9 (MSVPTQVLGLLLLWLTDAR-CEIVMTQSPATLSVSPGERATLSCRASQSVSSN-LAWYQQ KPGQAPRLLIYGTSTRATGI-PARFSGSGSGTEFTLTISSLQSEDFAV YYCQQYNNWPLTFG GGTKVEIKGGGGSGGGGSGGGGEVQLVESGG-GLVQPGRSLRLSCVASGFTFNDYAMH WVRQAPGK-GLEWVSVISWNSDSIGYADSVKGRFTISRDNAKNS-LYLQMHSLRAEDTAL YYCAKDN-HYGSGSYYYYQYGMDVWGQGTTVTVSSTTTPA-PRPPTPAPTIASQPLSLRPE ACRPAAGGAVHTRGLD-FACDIYIWAPLAGTCGVLLLSLVITLYCKRG RKKLLYIFKQPF MRPVQTTQEEDGCSCRFPEEEEGGCELRVKFSRS-ADAPAYQQGQNQLYNELNLGRREE YDVLDKRR-GRDPEMGGKPQRRKNPQEGLYNELQKDKMAEAY-SEIGMKGERRRGKGH DGLYQGLSTATKDTYDALHMQALPPR), a 3B9-CD8-BBz polypeptide comprising the following domains in order: a 3B9 binding domain, a CD8α hinge and transmembrane domain, a 4-1BB costimulation endodomain, and a CD3ζ signaling domain.

In some embodiments, the isolated nucleic acid encodes SEQ ID NO: 10 (MSVPTQVLGLLLLWLTDAR-CEIVMTQSPATLSVSPGERTTLSCRASQSVSSN-LAWYLQ KPGQAPRLLIYGASTRATGI-PARFSGSGSGTEFILTISSLQSEDFAVYYCQ QYNNWPITFG QGTRLEIKGGGGSGGGGSGGG-GEVQLVESGGGLVQPGRSLRLSCAASGFTFYDYAMH WVRQAPGKGLEWVSGISWNSGYIG-YADSVKGRFTISRDNAKNSLYLQMNSLRAEDTAL YYCAKDNSYGKFYYGLDVWGQGTTVTVSSTTTPA-PRPPTPAPTIASQPLSLRPEACRPA AGGAVHTRGLD-FACDIYIWAPLAGTCGVLLLSLVITLYCKRGRKKLLY-IFKQPFMRPVQ TTQEEDGCSCRFPEEEEGGCELRVKFSRSADAPA-YQQGGQNQLYNELNLGRREEYDVLD KRR-GRDPEMGGKPQRRKNPQEGLYNELQKDKMAEAY-SEIGMKGERRRGKGHDGLYQ GLSTATKDTYDALHMQALPPR), a 3H7-CD8-BBz poly-peptide comprising the following domains in order: a 3H7 binding domain, a CD8α hinge and transmembrane domain, a 4-1BB costimulation endodomain, and a CD3ζ signaling domain.

In some embodiments, the isolated nucleic acid encodes SEQ ID NO: 11 (MSVPTQVLGLLLLWLTDAR-CEIVLTQSPATLSLSPGERAALSCRASQSVS-NYLAWYQQ KPGQAPRLLIYDASNRATGI-PARFSGSGSGTDFTLTISSLEPEDFA VYYCQQRSNWPLTFG GGTKVEIR-GGGGSGGGGSGGGGEVQLVESGGGLVQPGRSLRLS-CAASGFTFRDYTMH WVRQGPGKGLEWVS-GISWNSDYIGYADSVKGRFTISRDNAKN SLYLQMNSLRVEDTAL YYCAKLSG-TYRDYFYGVDVWGQGTTVTVSSTTTPAPRPPTPAP-TIASQPLSLRPEACRPA AGGAVHTRGLDFACDIYI-WAPLAGTCGVLLLSLVITLYCKRGRKKLLYIF KQPFMRPVQ TTQEEDGCSCRFPEEEEGGCELRVKFSRSADAPA-YQQGGQNQLYNELNLGRREEYDVLD KRR-GRDPEMGGKPQRRKNPQEGLYNELQKDKMAEAY-SEIGMKGERRRGKGHDGLYQ GLSTATKDTYDALHMQALPPR), a 2B7-CD8-BBz poly-peptide comprising the following domains in order: a 2B7 binding domain, a CD8α hinge and transmembrane domain, a 4-1BB costimulation endodomain, and a CD3ζ signaling domain.

In some embodiments, the isolated nucleic acid encodes SEQ ID NO: 12 (MSVPTQVLGLLLLWLTDARCEIV-VTQSPATLSLSPGERATLSCRTSQTTTSYLAWYRQK PGQAPRLLIYDASNRAAGIPARFSGSGSGTDFTLTIN-SLEPEDFAVYYCQLRTNWITFGQG TRLEIKGGGGSGGGGSGGGGQVQLVES-GGDSVKPGGSLRLSCAASGFTFSDSYMTWIR QAPGKGLEWVSFISSSGSTIYYADSVKGRFTIS-RDNVKKSLYLQMNRLRAEDTAVYYCA REEPGNYVYYGMDVWGQGTTVTVSSTTTPAPRPPT-PAPTIASQPLSLRPEACRPAAGGA VHTRGLD-FACDIYIWAPLAGTCGVLLLSLVITLYCKRGRKKLLY-IFKQPFMRPVQTTQEE DGCSCRFPEEEEGGCELRVKFSRSADAPA-YQQGGQNQLYNELNLGRREEYDVLDKRRGR DPEMGGKPQRRKNPQEGLYNELQKDKMAEAYSEI-GMKGERRRGKGHDGLYQGLSTAT KDTY-DALHMQALPPR), a 9C11-CD8-BBz polypeptide com-prising the following domains in order: a 9C11 binding domain, a CD8α hinge and transmembrane domain, a 4-1BB costimulation endodomain, and a CD3ζ signaling domain.

In some embodiments, the isolated nucleic acid encodes SEQ ID NO: 20 (M S V P T Q V L G L L L L W L T D A R C E I V M T Q S P A T L S V S P G E R I T L S C R A S Q S V S S N L A W Y L Q K P G Q A P R L L I Y G A S T R A T G I P A R F S G S G S G T E F I L T I S S L Q S E D F A V Y Y C Q Q Y N N W P I T F G Q G T R L E I K G G G G S G G G G S G G G G E V Q L V E S G G G L V Q P G R S L R L S C A A S G F T F Y D Y A M H W V R Q A P G K G L E W V S G I S W N S G Y I G Y A D S V K G R F T I S R D N A K N S L Y L Q M N S L R A E D T A L Y Y C A K D N S Y G K F Y Y G L D V W G Q G T T V T V S S T T T P A P R P P T P A P T I A S Q P L S L R P E A C R P A A G G A V H T R G L D F A C D I Y I W A P L A G T C G V L L L S L V I T L Y C R V K F S R S A D A P A Y Q Q G Q N Q L Y N E L N L G R R E E Y D V L D K R R G R D P E M G G K P Q R R K N P Q E G L Y N E L Q K D K M A E A Y S E I G M K G E R R R G K G H D G L Y Q G L S T A T K D T Y D A L H M Q A L P P R), a 3H7-CD3z polypeptide comprising the following domains in order: a 3H7 binding domain, a CD8α hinge and transmembrane domain, and a CD3ζ signaling domain.

In some embodiments, the isolated nucleic acid encoding a 3H7-CD8-27z polypeptide comprises the sequence of SEQ ID NO:13 (ATGTCCGTGCC-TACCCAGGTGCTGGGCCTGCTGCTGCT GTGGCTGACCGACGCCAG ATGCGAAATAGT-GATGACGCAGTCTCCAGC-CACCCTGTCTGTGTCTCCAGGGGAAAG AAC-CACCCTCTCCTGCAGGGCCAGTCAGAG TGTTAGCAGCAACTTAGCCTGGTACCT TCAGAAACCTGGCCCAGGCTCCCAGGCTCCTCATC-TATGGTGCATCCACCAGGGCCAC TGGTATCCCAGCCAGGTTCAGTGGCA GTGGGTCTGGGACAGAGTTCATTCTCACCAT CAGCAGCCTGCAGTCTGAAGATTTTGCAGTTTAT-TACTGTCAGCAGTATAATAACTG GCCGAT-CACCTTCGGCCAAGGGACACGGCTGGAGAT-TAAAGGTGGAGGTGGATCTG GAGGAGGAGGATCCGGTGGAGGAGGT-GAAGTGCAACTGGTGGAGTCTGGGGGAGG CTTGGTACAGCCTGGCAGGTCCCTGA-GACTCTCCTGTGCAGCCTCTGGATTCACCTTT TAT-GATTATGCCATGCACTGGGTCCGGCAAGCTCCAGG-GAAGGGCCTGGAGTGGGT CTCAGGTATTAGTTGGAATAGTGGTTACATAGGC-TATGCGGACTCTGTGAAGGGCCG ATTCAC-CATCTCCAGAGACAACGC-CAAGAACTCCCTGTATCTGCAAATGAACAGTCT GAGAGCTGAGGACACGGCCTTGTAT-TACTGTGCAAAAGATAACAGCTATGGAAAGT TCTACTACGGTTTGGACGTCTGGGGCCAAGGGAC-CACGGTCACCGTCTCCTCAACCA CGACGCCAGCGCCGCGACCACCAACACCGGCGCC-CACCATCGCGTCGCAGCCCCTG TCCCTGCGCCCAGAGGCGTGCCGG CCAGCGGCGGGGGGCGCAGTGCACACGAGGGG GCTGGACTTCGCCTGTGATATCTA-CATCTGGGCGCCCTTGGCCGGGACTTGTGGGGT CCTTCTCCTGTCACTGGTTATCACCCTTTACTGC-CAACGACGCAAGTACCGCTCCAAT AAAGGAGAGT-CACCAGTAGAACCCGCCGAACCTTGTCACTATT-CATGTCCACGCGA AGAGGAGGGTTCAACGATCCCTATTCAGGAAGAT-TACAGAAAGGCCGGAACCTGCTT GTAGCCCCAGAGT-GAAGTTCAGCCGCAGCGCCGACGCCCCTGCC-TACCAGCAGGGC CAGAACCAGCTGTATAACGAGCT- GAACCTGGGCAGGCGGGAGGAATACGACGTGCTGGACAAGCGCAGAGGCCGGGACCCT-GAGATGGGCGGCAAGCCCCAGAGGCGGAAGAACCCCCAG-GAAGGCCTGTATAACGAACTGCAGAAAGACAA-GATGGCCGAGGCCTA CAGCGAGATCGGCAT-GAAGGGCGAGCGGCGACGCGGCAAGGGCCACGACGGCCTG TACCAGGGCCTGTCCACCGC-CACCAAGGACACCTACGACGCCCTGCA-CATGCAGGC CCTGCCTCCCCGTTAG).

In some embodiments, the isolated nucleic acid encoding a 3H7-CD8-BBz polypeptide comprises the sequence of SEQ ID NO:14 (ATGTCCGTGCC-TACCCAGGTGCTGGGCCTGCTGCTGCTGTGGCTGACCGACGCCAG ATGCGAAATAGT-GATGACGCAGTCTCCAGC-CACCCTGTCTGTGTCTCCAGGGGAAAG AAC-CACCCTCTCCTGCAGGGCCAGTCAGAGTGTTAGCAGCAACTTAGCCTGGTACCTTCAGAAACCTGGCCAGGCTCCCAGGCTCCTCATC-TATGGTGCATCCACCAGGGCCACTGGTATCCCAGCCAGGTTCAGTGGCAGTGGGTCTGGGACAGAGTTCATTCTCACCATCAGCAGCCTGCAGTCTGAAGATTTTGCAGTTTAT-TACTGTCAGCAGTATAATAACTG GCCGAT-CACCTTCGGCCAAGGGACACGGCTGGAGAT-TAAAGGTGGAGGTGGATCTGGAGGAGGAGGATCCGGTGGAGGAGGT-GAAGTGCAACTGGTGGAGTCTGGGGGAGGCTTGGTACAGCCTGGCAGGTCCCTGA-GACTCTCCTGTGCAGCCTCTGGATTCACCTTT TAT-GATTATGCCATGCACTGGGTCCGGCAAGCTCCAGG-GAAGGGCCTGGAGTGGGTCTCAGGTATTAGTTGGAATAGTGGTTACATAGGC-TATGCGGACTCTGTGAAGGGCCG ATTCAC-CATCTCCAGAGACAACGC-CAAGAACTCCCTGTATCTGCAAATGAACAGTCTGAGAGCTGAGGACACGGCCTTGTAT-TACTGTGCAAAAGATAACAGCTATGGAAAGTTCTACTACGGTTTGGACGTCTGGGGCCAAGGGAC-CACGGTCACCGTCTCCTCAACCACGACGCCAGCGCCGCGACCACCAACACCGGCGCC-CACCATCGCGTCGCAGCCCCTGTCCCTGCGCCCAGAGGCGTGCCGGCCAGCGGCGGGGGGCGCAGTGCACACGAGGGGGCTGGACTTCGCCTGTGATATCTA-CATCTGGGCGCCCTTGGCCGGGACTTGTGGGGTCCTTCTCCTGTCACTGGTTATCACCCTT-TACTGCAAACGGGGCAGAAAGAAACTCCTGTATATATTCAAACAACCATTTATGAGACCAGTA-CAAACTACTCAAGAGGAAGATG GCTGTAGCTGCC-GATTTCCAGAAGAAGAAGAAGGAGGATGTGAACT-GAGAGTGAAGTTCAGCAGGAGCGCA-GACGCCCCGCGTACCAGCAGGGCCAGAACCAGCTCTATAA CGAGCT-CAATCTAGGACGAAGAGAGGAGTAC-GATGTTTTGGACAAGAGACGTGGCC GGGACCCT-GAGATGGGGGGAAAGCCGCAGAGAAGGAAGAACCCTCAGGAAGGCCT GTACAAT-GAACTGCAGAAAGATAAGATGGCGGAGGCCTA-CAGTGAGATTGGGATGA AAGGCGAGCGCCG-GAGGGGCAAGGGGCACGATGGCCTTTACCAGGGTCTCAGTACA GCCAC-CAAGGACACCTACGACGCCCTTCA-CATGCAGGCCCTGCCCCCTCGCTAA).

In some embodiments, the isolated nucleic acid encoding a 3B9-CD8-BBz polypeptide comprises the sequence of SEQ ID NO:15 (ATGAGCGTTCCAACC-CAAGTTCTGGGACTGCTTCTGCTCT GGTTGACTGACGCTAGG TGCGAAATAGTAATGACCCAATCCCCAGC-CACTCTCTCCGTTAGCCCAGGTGAAAGA GCCACTCTTAGTTGCAGGGCTAGT-CAATCCGTATCTAGCAACCTGGCCTGGTACCAG CAAAAGCCCGGACAAGCGCCGCGGTTGTTGATC-TATGGGACGAGCACACGAGCTAC GGGTAT-TCCGGCCAGGTTCTCAGGGTCTGGCTCCG-GAACCGAATTTACATTGACGAT CAGTAGTCTGCAATCAGAGGATTTCGCCGTTTACT-ATTGCCAACAGTACAATAATTG GCCGCTCACAT-TCGGGGGAGGAACCAAGGTCGAGATTAAGG-GAGGTGGGGGTAGTG GGGGCGGGGGGTCAGGAGGTGGAGGAGAGGTA-CAGTTGGTAGAAAGCGGCGGGGG GTTGGTT-CAACCTGGACGGAGTCTGAGAT-TGTCTTGCGTGGCTTCCGGCTTTACTTTC AATGATTACGC-CATGCACTGGGTACGCCAGGCGCCTG-GAAAGGGTCTGGAGTGGGT TTCCGTGATATCCTG-GAATAGTGATAGTATAGGCTA TGCCGATAGTGTAAAAGGAAG GTTTA-CAATCTCTAGGGA-TAACGCTAAGAACAGCCTGTACCTTCAAATGCAT-AGTCT CCGGGCTGAGGACACAGCCTTGTACTAT-TGTGCTAAGGACAATCATTATGGAAGCG GGTCAT-ATTATTACTATCAATATGGGATG-GATGTGTGGGGTCAGGGAACGACCGTTA CGGTATCCTCAACCACCACCCCTGCAC-CAAGGCCCCCGACTCCCGCGCCCACCATCG CGT-CACAGCCTCTTAGCCTGCGACCGGAAGCATGCA-GACCAGCTGCCGGGGGGGCC GTGCATACGAGAGGTTTGGACTTCGCCTGCGA-TATCTACATCTGGGCGCCCTTGGCC GGGACTTGTGGGGTCCTTCTCCTGTCACTGGTTAT-CACCCTTTACTGCAAACGGGGC AGAAAGAAACTCCTGTATATATTCAAACAACCATT-TATGAGACCAGTACAAACTACT CAAGAGGAA-GATGGCTGTAGCTGCCGAT-TTCCAGAAGAAGAAGAAGGAGGATGTG AACTGAGAGTGAAGTTCAGCAGGAGCGCA-GACGCCCCCGCGTACCAGCAGGGCCAG AACCAGCTCTATAACGAGCT-CAATCTAGGACGAAGAGAGGAGTAC-GATGTTTTGGA CAAGAGACGTGGCCGGGACCCT-GAGATGGGGGGAAAGCCGCAGAGAAGGAAGAAC CCTCAGGAAGGCCTGTACAATGAACTGCAGAAA-GATAAGATGGCGGAGGCCTACAG TGAGATTGG-GATGAAAGGCGAGCGCCG-GAGGGGCAAGGGGCACGATGGCCTTTACC AGGGTCTCAGTACAGCCACCAAGGACACC-TACGACGCCCTTCACATGCAGGCCCTG CCCCCTCGCTAA).

In some embodiments, the isolated nucleic acid encoding a 2B7-CD8-BBz polypeptide comprises the sequence of SEQ ID NO:16 (ATGTCCGTACC-TACCCAGGTGCTGGGCCTGCTGCT GCTGTGGCTGACCGACGCCAG ATGCGAAAT-TGTGTTGACACAGTCTCCAGC-CACCCTGTCTTTGTCTCCAGGGGAAAG AGCCGCCCTCTCCTGCAGGGCCAGTCAGAGTGT-TAGCAACTACTTAGCCTGGTACCA ACAGAAACCTGGCCAGGCTCCCAGGCTCCTCATC-TATGATGCATCCAACAGGGCCA CTGG-CATCCCAGCCAGGTTCAGTGGCAGTGG GTCTGGGACAGACTTCACTCTCACCA TCAGCAGCCTAGAGCCTGAAGATTTTGCAGTTTAT-TACTGTCAGCAGCGTAGCAACT GGCCGCT-CACTTTCGGCGGAGGGACCAAGGTG-GAGATCAGAGGTGGAGGTGGATCT GGAGGAGGAGGATCCGGTGGAGGAGGT-GAAGTGCAGCTGGTGGAGTCTGGGGGAG GCTTGGTA-CAGCCTGGCAGGTCCCTGCGACTCTCCTG TGCAGCCTCTGGATTCACCT TTCGAGATTATAC-CATGCACTGGGTCCGGCAAGGTCCAGG-GAAGGGCCTGGAATGG GTCTCAGGTATTAGTTG-GAATAGTGATTACATAGGCTATGCGGACTCT GTGAAGGGC CGATTCACCATCTCCAGA-GACAACGCCAAGAACTCCCTGTATCTGCAAAT-GAACAGT CTGAGAGTTGAGGACACGGCCTTGTAT-TACTGTGCAAAGCTCAGTGGGACCTACAG GGACTACTTCTACGGAGTGGACGTCTGGGGC-CAAGGGACCACGGTCACCGTCTCCTC AACCAC-CACCCCTGCACCAAGGCCCCCGACTCCCGCGCC-CACCATCGCGTCACAGCC TCTTAGCCTGCGACCGGAAGCATGCA-GACCAGCTGCCGGGGGGGCCGTGCATACGA GAGGTTTGGACTTCGCCTGCGATATCTA-CATCTGGGCGCCCTTGGCCGGGACTTGTG GGGTCCTTCTCCTGTCACTGGTTATCACCCTT-TACTGCAAACGGGGCAGAAAGAAAC TCCTGTATATATTCAAACAACCATTTATGA-GACCAGTACAAACTACTCAAGAGGAAG ATGGCTGTAGCTGCCGAT-TTCCAGAAGAAGAAGAAGGAGGATGTGAACT-GAGAGTG AAGTTCAGCAGGAGCGCA-GACGCCCCCGCGTACCAGCAGGGC CAGAACCAGCTCTA TAACGAGCT-CAATCTAGGACGAAGAGAGGAGTAC-GATGTTTTGGACAAGAGACGTG GCCGGGACCCT-GAGATGGGGGGAAAGCCGCAGAG AAGGAAGAACCCTCAGGAAGG CCTGTACAAT-GAACTGCAGAAAGATAAGATGGCGGAGGCCTA-CAGTGAGATTGGGA TGAAAGGCGAGCGCCG-GAGGGGCAAGGGGCACGATGGCCTTTA CCAGGGTCTCAGT ACAGCCACCAAGGACACC-TACGACGCCCTTCA-CATGCAGGCCCTGCCCCCTCGCTAA).

In some embodiments, the isolated nucleic acid encoding a 9C11-CD8-BBz polypeptide comprises the sequence of SEQ ID NO:17 (ATGTCCGTGCC-TACCCAGGTGCTGGGCCTGCTGCTGC TGTGGCTGACCGACGCCAG ATGCGAAAT-TGTGGTGACACAGTCTCCAGC-CACCCTGTCTTTGTCTCCAGGGGAAAG AGC-CACCCTCTCCTGCAGGACCAGTCAG ACTACTACCAGCTACTTAGCCTGGTACCG ACAGAAACCTGGCCAGGCTCCCAGGCTCCTCATC-TATGATGCATCCAACAGGGCCG CTGG-CATCCCAGCCAGGTTCAGTGGCAGTG GGTCTGGGACAGACTTCACTCTCACCA TCAACAGCCTGGAGCCTGAAGATTTTGCAGTTTAT-TACTGTCAGCTGCGTACCAACT GGAT-CACCTTCGGCCAAGGGACACGACTGGAGAT-TAAAGGTGGAGGTGGATCTGGA GGAGGAGGATCCGGTGGAG-GAGGTCAGGTGCAGCTGGTGGAGTCTGGGGGA-GACTC GGTCAAGCCTGGAGGGTCCCTGA- GACTCTCCTGTGCAGCCTCTGGATTCACCTTCAG TGACTCCTACATGACTTG-GATCCGCCAGGCTCCAGGGAAGGGGCTG-GAGTGGGTTTC ATTCATTAGTAGTAGTGGAAGTAC-CATATATTATGCAGACTCTGTGAAGGGCCGATT CACCATTTCCAGGGACAACGTCAAGAAGTCAT-TGTATCTGCAGATGAACAGACTGA GAGCCGAGGACACGGCCGTGTAT-TACTGTGCGAGAGAAGAACCAGGAAACTACGTC TATTACGGTATGGACGTCTGGGGCCAAGGGAC-CACGGTCACCGTCTCCTCAACCACC ACCCCTGCACCAAGGCCCCCGACTCCCGCGCC-CACCATCGCGTCACAGCCTCTTAGC CTGCGACCG-GAAGCATGCAGACCAGCTGCCGGGGGGGCCGTG-CATACGAGAGGTTT GGACTTCGCCTGCGATATCTA-CATCTGGGCGCCCTTGGCCGGGACTTGTGGGGTCCT TCTCCTGTCACTGGTTATCACCCTT-TACTGCAAACGGGGCAGAAAGAAACTCCTGTA TATATTCAAACAACCATTTATGAGACCAGTA-CAAACTACTCAAGAGGAAGATGGCT GTAGCTGCC-GATTTCCAGAAGAAGAAGAAGGAGGATGTGAACT-GAGAGTGAAGTTC AGCAGGAGCGCA-GACGCCCCCGCGTACCAGCAGGGCCAG AACCAGCTCTATAACGA GCT-CAATCTAGGACGAAGAGAGGAGTAC-GATGTTTTGGACAAGAGACGTGGCCGGG ACCCT-GAGATGGGGGGAAAGCCGCAGAGAA GGAAGAACCCTCAGGAAGGCCTGTA CAAT-GAACTGCAGAAAGATAAGATGGCGGAGGCCTA-CAGTGAGATTGGGATGAAA GGCGAGCGCCG-GAGGGGCAAGGGGCACGATGGCCTTTA CCAGGGTCTCAGTACAGC CACCAAGGACACC-TACGACGCCCTTCA-CATGCAGGCCCTGCCCCCTCGCTAA).

In some embodiments, the isolated nucleic acid comprises a codon optimized sequence encoding a CD8α hinge region. Exemplary codon optimized CD8α hinge region nucleic acid sequences include, without limitation, SEQ ID NO: 18 (ACCACCACCCCTGCAC-CAAGGCCCCCGACTCCCGCGCCCACCATCGCGTCA CAGCCTCTTAGCCTGCGACCGGAAGCATGCA-GACCAGCTGCCGGGGGGGCCGTGCA TACGAGAGGTTTGGACTTCGCCTGCGAT). In some embodiments, the CD8α hinge region is encoded by the following sequence SEQ ID NO:19 (AC-CACGACGCCAGCGCCGCGACCAC-CAACACCGGCGCCCACCATCGCGTCGCAGCC CCTGTCCCTGCGCCCAGAGGCGTG CCGGCCAGCGGCGGGGGGCGCAGTGCACACGA GGGGGCTGGACTTCGCCTGTGAT).

In some embodiments, the isolated nucleic acid encodes a 3B9 binding domain and comprises the following sequence encoding a CD8α hinge domain SEQ ID NO: 18. In some embodiments, the isolated nucleic acid encodes a 2B7 binding domain and comprises the following sequence encoding a CD8α hinge domain SEQ ID NO:18. In some embodiments, the isolated nucleic acid encodes a 9C11 binding domain and comprises the following sequence encoding a CD8α hinge domain SEQ ID NO:18. In some embodiments, the isolated nucleic acid encodes a 3H7 binding domain and comprises the following sequence encoding a CD8α hinge domain SEQ ID NO: 19.

In some embodiments, the isolated nucleic acid encodes SEQ ID NO: 35 (MSVPTQVLGLLLLWLTDARCE-VQLVESGGGLVQPGGSLRLSCAASGFTFSSYVMSWV RQAPGKGLEWVSAIIGSGGSTYYADSVKGRFTIS-
RDNSKNTLYLQMNSLRAEDTAVYYC
AKRAGDNWNWFDPWGQGTLVTVSSGGGG
SGGGGSGGGGDIQMTQSPSSVSASLGDRV TIT-
CRASQGISSWLAWYQRKPGKAPKLLI-
YAASSLQSGVPSRFSGSGSGADFTLTISSLQP EDFA-
TYYCQQAKSVPFTFGPGTKVDIKTTTPAP
RPPTPAPTIASQPLSLRPEACRPAAGGA VHTRGLD-
FACDIYIWAPLAGTCGVLLLSLVITLYCKRGRKKLLY-
IFKQPFMRPVQTTQEE
DGCSCRFPEEEEGGCELRVKFSRSADAPA-
YQQGQNQLYNELNLGRREEYDVLDKRRGR
DPEMGGKPQRRKNPQEGLYNELQKDKMAEAYSEI-
GMKGERRRGKGHDGLYQGLSTAT KDTY-
DALHMQALPPR), an anti-BCMA-CAR polypeptide com-
prising the following domains in order: a 16716P binding
domain, a CD8α hinge and transmembrane domain, a 4-1BB
costimulation endodomain, and a CD3ζ signaling domain.

In some embodiments, the isolated nucleic acid encodes
SEQ ID NO: 36 (MSVPTQVLGLLLLWLT-
DARCQVQLVESGGGLVKPGGSLRLS-
CAASGFTFSDYYISWIR QAPGKGLEWVSYIS-
SSGSSIKYADSVKGRFTISRDNAKNSLYLQMNSLRAE-
DTAVYYCA
REGGNYGMDVWGQGTTVTVSSGGGGSGGG
GSGGGGDIQMTQSPSSVSASVGDRVTIT
CRASQGINNWLVWYQQKPGKAPKLLIYAAT-
SLQSGVPSRFSGSGSGTDFTLTISSLQPED
FATYYCQQANSFPPTFGQGTKLEIKTTTPAPRPPTPAP-
TIASQPLSLRPEACRPAAGGAVH TRGLDFACDIYI-
WAPLAGTCGVLLLSLVITLYCKRGRKKLLY-
IFKQPFMRPVQTTQEEDG
CSCRFPEEEEGGCELRVKFSRSADAPAYQQGQNQLY-
NELNLGRREEYDVLDKRRGRDP
EMGGKPQRRKNPQEGLYNELQKDKMAEAYSEI-
GMKGERRRGKGHDGLYQGLSTATKD
TYDALHMQALPPR), an anti-BCMA-CAR polypeptide
comprising the following domains in order: a 16747P bind-
ing domain, a CD8α hinge and transmembrane domain, a
4-1BB costimulation endodomain, and a CD3C signaling
domain.

In some embodiments, the isolated nucleic acid encodes
SEQ ID NO: 37 (MSVPTQVLGLLLLWLT-
DARCQVQLQESGPGLVKPSETLSLTCTVSGGS-
INYYYWNWIR QPPGKGLEWIGYISYS-
GNTNYNPSLKSRVTISVATSRN
QFSLTLSSVTAADTAVYYCARF AEYCGGNI-
CYYYGMDVWGQGTTVTVSSGGGGSGGGGSGG
GGEIVLTQSPGTLSLSPGE RATFSCRASQSVGSSF-
LAWYQQKPGQAPRRLMYGASNRAT-
GIPDRFSGSGSGTDFTLTIS RLEPED-
FAVYYCQQCGGSPWTFGQGTKVEIKTTTP
APRPPTPAPTIASQPLSLRPEACRPA AGGAVHTRGLD-
FACDIYIWAPLAGTCGVLLLSLVITLYCKRGRKKLLY-
IFKQPFMRPVQ
TTQEEDGCSCRFPEEEEGGCELRVKFSRSADAPA-
YQQGQNQLYNELNLGRREEYDVLD KRR-
GRDPEMGGKPQRRKNPQEGLYNELQKDKMAEAY-
SEIGMKGERRRGKGHDGLYQ
GLSTATKDTYDALHMQALPPR), an anti-BCMA-CAR
polypeptide comprising the following domains in order: a
21587N binding domain, a CD8α hinge and transmembrane
domain, a 4-1BB costimulation endodomain, and a CD3ζ
signaling domain.

In some embodiments, the isolated nucleic acid encodes
SEQ ID NO: 38 (MSVPTQVLGLLLLWLT-
DARCQVQLVESGGGLVKPGGSLRLS- CAASGFTFSDYYISWIR QAPGKGLEWVSYIS-
SSGSSIKYADSVKGRFTISRDNAKNSLYLQMNSLRAE-
DTAVYYCA REGGNYGMDVWGQGTTVTVSSGGG
GSGGGGSGGGGDIQMTQSPSSVSASVGDRVTIT
CRASQGINNWLVWYQQKPGKAPKLLIYAAT-
SLQSGVPSRFSGSGSGTDFTLTISSLQPED
FATYYCQQANSFPPTFGQGTKLEIKTTTPAPRPPTPAP-
TIASQPLSLRPEACRPAAGGAVH TRGLDFACDIYI-
WAPLAGTCGVLLLSLVITLYCKRGRKKLLY-
IFKQPFMRPVQTTQEEDG
CSCRFPEEEEGGCELRVKFSRSADAPAYQQGQNQLY-
NELNLGRREEYDVLDKRRGRDP
EMGGKPQRRKNPQEGLYNELQKDKMAEAYSEI-
GMKGERRRGKGHDGLYQGLSTATKD
TYDALHMQALPPRRAKRSGSGATNFSLLKQAGD-
VEENPGPMALPVTALLLPLALLLHA ARPNWVNVIS-
DLKKIEDLIQSMHIDATLYTESDVHPSCKVTAMKCFL-
LELQVISLESGDA
SIHDTVENLIILANNSLSSNGNVTESGCKE-
CEELEEKNIKEFLQSFVHIVQMFINTS*), an anti-
BCMA-CAR polypeptide comprising the following
domains in order: a 16747P binding domain, a CD8α hinge
and transmembrane domain, a 4-1BB costimulation endodo-
main, a CD3ζ signaling domain, a furin+P2A cleavage
domain, a secretion signal, and a sIL15 domain.

In some embodiments, the isolated nucleic acid encoding
an anti-BCMA CAR 16716P polypeptide comprises the
sequence of SEQ ID NO: 39 (ATGAGCGTGCC-
TACCCAGGTGCTGGGACTGCTGCTGCTG
TGGCTGACAGACGCAAG
GTGCGAGGTGCAGCTGGTGGAGTCCGGAG-
GAGGACTGGTGCAGCCAGGAGGATCCC
TGAGGCTGTCTTGCGCCGCCAGCGGCTTCACCTT-
TAGCTCCTACGTGATGTCCTGGGT
GCGCCAGGCACCTGGCAAGGGACTG-
GAGTGGGTGTCTGCCATCATCGGCTCTGGCG
GCAGCACATACTATGCCGACAGCGT-
GAAGGGCCGGTTCACCATCTCCAGAGATAAC
TCTAAGAATACACTGTATCTGCAGATGAACAGCCT-
GAGGGCAGAGGACACCGCCGT GTACTATTGCGC-
CAAGAGAGCCGGCGACAACTGGAATTGGTTT-
GATCCATGGGGCC
AGGGCACCCTGGTGACAGTGTCTAGCGGAGGAG-
GAGGATCTGGAGGAGGAGGAAG CGGCGGAG-
GAGGCGACATCCAGATGACACAGTCCC-
CATCCTCTGTGAGCGCCTCCC
TGGGCGATAGGGTGACCATCA-
CATGTCGCGCCTCTCAGGG-
CATCAGCTCCTGGCTGG CATGGTACCAGAG-
GAAGCCAGGCAAGGCCCCTAAGCTGCT
GATCTATGCAGCATCT AGCCTGCAGAGCG-
GAGTGCCTTCCCGGTTCTCTGGAAGCGGATCCG-
GAGCAGACTTT
ACCCTGACAATCTCCTCTCTGCAGCCAGAGGAT-
TTCGCCACCTACTATTGTCAGCAG
GCCAAGTCCGTGCCATT-
CACCTTTGGCCCCGGCACAAAGGTGGATATCAA-
GACCACC ACCCCTGCAC-
CAAGGCCCCCGACTCCCGCGCCCACC
ATCGCGTCACAGCCTCTTAGC CTGCGACCG-
GAAGCATGCAGACCAGCTGCCGGGGGGGCCGTG-
CATACGAGAGGTTT GGACTTCGCCTGCGATATCTA-
CATCTGGGCGCCCTTGGCCGGGACTTG
TGGGGTCCT TCTCCTTGTCACTGGTTATCACCCTT-
TACTGCAAACGGGGCAGAAAGAAACTCCTGTA
TATATTCAAACAACCATTTATGAGACCAGTA-
CAAACTACTCAAGAGGAAGATGGCT GTAGCTGCC- GATTTCCAGAAGAAGAAGAAGGAGGATGTGAACT-
GAGAGTGAAGTTC
AGCAGGAGCGCAGACGCCCCCGCGTACCAGCAG
GGCCAGAACCAGCTCTATAACGA GCT-
CAATCTAGGACGAAGAGAGGAGTAC-
GATGTTTTGGACAAGAGACGTGGCCGGG ACCCT-
GAGATGGGGGGAAAGCCGCAGAGAAGGA
AGAACCCTCAGGAAGGCCTGTA CAAT-
GAACTGCAGAAAGATAAGATGGCGGAGGCCTA-
CAGTGAGATTGGGATGAAA GGCGAGCGCCG-
GAGGGGCAAGGGGCACGATGGCCTTTACCA
GGGTCTCAGTACAGC CACCAAGGACACC-
TACGACGCCCTTCA-
CATGCAGGCCCTGCCCCCTCGCTAA).

In some embodiments, the isolated nucleic acid encoding
an anti-BCMA CAR 16747P polypeptide comprises the
sequence of SEQ ID NO: 40 (ATGAGCGTGCC-
TACCCAGGTGCTGGGACTGCTGCTGCTGTGG
CTGACAGACGCAAG GTGCCAGGTGCAGCTGGTG-
GAGAGCGGAGGAGGACTGGTGAAGCCAGGAG-
GAAGC CTGAGGCTGTCCTGCGCCGCCTCTGGCTT-
CACCTTTAGCGACTACTATATCTCCTGGA
TCAGGCAGGCACCTGGCAAGGGACTG-
GAGTGGGTGTCCTACATCAGCTCCTCTGGC AGCTC-
CATCAAGTATGCCGACTCTGTGAAGGGCCGGTT-
CACCATCTCCAGAGATAAC
GCCAAGAATTCTCTGTACCTGCAGAT-
GAACAGCCTGCGGGCCGAGGACACAGCCGT
GTACTATTGCGCCAGAGAGGGCGGCAATTATGG-
CATGGACGTGTGGGGCCAGGGCA
CCACAGTGACCGTGTCTAGCGGCGGCG
GCGGCTCTGGAGGAGGAGGAAGCGGCGG
AGGAGGCGACATCCAGATGACACAGAGCC-
CATCCAGCGTGAGCGCCAGCGTGGGCG
ATAGGGTGACCATCACATGTCGCGCCTCCCAGGG-
CATCAACAATTGGCTGGTGTGGT
ACCAGCAGAAGCCAGGCAAGGCCCCCAAGCTGCT-
GATCTATGCAGCCACCTCCCTG CAGTCTG-
GAGTGCCTAGCCGGTTCTCCGGATCTGGAAGCG-
GAACCGACTTTACCCTG
ACAATCAGCTCCCTGCAGCCAGAGGATTTTGCCA-
CATACTATTGTCAGCAGGCCAAC TCCTTCCCCCC-
TACCTTTGGCCAGGGCACAAAGCTGGAGATCAA-
GACCACCACCCT
GCACCAAGGCCCCCGACTCCCGCGCCCAC-
CATCGCGTCACAGCCTCTTAGCCTGCGA CCG-
GAAGCATGCAGACCAGCTGCCGGTGGGGCGGTG-
CATACGAGAGGTTTGGACTT
CGCCTGCGATATCTA-
CATCTGGGCGCCCTTGGCCGGGACTTGT
GGGGTCCTTCTCCT GTCACTGGTTATCACCCTT-
TACTGCAAACGGGGCAGAAAGAAACTCCTGTATAT-
ATT CAAACAACCATTTATGAGACCAGTACAAAC-
TACTCAAGAGGAAGATGGCTGTAGCT
GCCGATTTCCAGAAGAAGAAGAAGGAGGATGT-
GAACTGAGAGTGAAGTTCAGCAG GAGCGCA-
GACGCCCCCGCGTACCAGCAGGGCCAGA
ACCAGCTCTATAACGAGCTCA
ATCTAGGACGAAGAGAGGAGTAC-
GATGTTTTGGACAAGAGACGTGGCCGGGACCCT
GAGATGGGGG-
GAAAGCCGCAGAGAAGGAAGAACCCTCAG-
GAAGGCCTGTACAATG AACTGCAGAAAGATAA-
GATGGCGGAGGCCTACAGTGAGATTG
GGATGAAAGGCGA GCGCCG-
GAGGGGCAAGGGGCACGATGGCCTT-

TACCAGGGTCTCAGTACAGCCACCA AGGACACC-
TACGACGCCCTTCACATGCAGGCCCTG
CCCCCTCGCTAA).

In some embodiments, the isolated nucleic acid encoding
an anti-BCIA CAR 21587N polypeptide comprises the
sequence of SEQ ID NO: 41 (ATGAGCGTGCC-
TACCCAGGTGCTGGGACTGCTGCTGCTG
TGGCTGACAGACGCAAG
GTGCCAGGTGCAGCTGCAG-
GAGTCTGGCCCTGGCCTGGTGAAGCCATCCGA-
GACCC TGTCTCTGACCTGCACAGT-
GAGCGGCGGCTCCATCAATTACTATTACTGG
AACTGGA TCAGGCAGCCACCTGGCAAGGGACTG-
GAGTGGATCGGCTACATCAGCTATTCCGGC AACAC-
CAATTACAACCCTTCTCTGAAGAGCAGGGTGAC-
CATCAGCGTGGCCACATC
CCGCAATCAGTTCAGCCTGACACT-
GAGCTCCGTGACCGCAGCAGACACAGCCGTGT
ATTACTGCGCAAGGTTTGCAGAGTACTGCG-
GAGGCAACATCTGTTATTACTATGGCA
TGGACGTGTGGGGCCAGGGCAC-
CACAGTGACCGTGTCTAGCGGCGGCGGCGGCTCT
GGAGGAGGAGGAAGCGGAGGAGGAG-
GAGAGATCGTGCTGACCCAGTCCCCAGGCA
CACTGTCTCTGAGCCCTGGAGAGAGGGCCACAT-
TCTCTTGTCGCGCCTCCCAGTCTG
TGGGCTCCTCTTTTCTGGCCTGGTACCAGC
AGAAGCCAGGACAGGCACCACGGAGA
CTGATGTATGGAGCATCCAATAGGGCAACCG-
GAATCCCAGACAGATTCAGCGGCTC
CGGCTCTGGCACAGACTT-
CACCCTGACAATCAGCAGACTG-
GAGCCAGAGGACTTCG CCGTGTACTAT-
TGCCAGCAGTGTGGAGGATCCCCATGGACC
TTTGGCCAGGGAACAA AGGTGGAGATCAAGAC-
CACCACCCTGCAC-
CAAGGCCCCCGACTCCCGCGCCCACC ATCGCGT-
CACAGCCTCTTAGCCTGCGACCGGAAGC
ATGCAGACCAGCTGCCGGGGG GGCCGTGCAT-
ACGAGAGGTTTGGACTTCGCCTGCGATATCTA-
CATCTGGGCGCCCTT
GGCCGGGACTTGTGGGGTCCTTCTCCTGT-
CACTGGTTATCACCCTTTACTGCAAACG
GGGCAGAAAGAAACTCCTGTATATATTCAAACAAC-
CATTTATGAGACCAGTACAAA CTACTCAAGAG-
GAAGATGGCTGTAGCTGCCGAT-
TTCCAGAAGAAGAAGAAGGAGGA
TGTGAACTGAGAGTGAAGTTCAGCAGGAGCGCA-
GACGCCCCGCGTACCAGCAGGG
CCAGAACCAGCTCTATAACGAGCT-
CAATCTAGGACGAAGAGAGGAGTACGATGTTT
TGGACAAGAGACGTGGCCGGGACCCT-
GAGATGGGGGGAAAGCCGCAGAGAAGGAA
GAACCCTCAGGAAGGCCTGTACAAT-
GAACTGCAGAAAGATAAGATGGCGGAGGCCT
ACAGTGAGATTGGGATGAAAGGCGAGCGCCG-
GAGGGGCAAGGGGCACGATGGCCT
TTACCAGGGTCTCAGTACAGCCACCAAGGACACC-
TACGACGCCCTTCACATGCAGG
CCCTGCCCCCTCGCTAA).

In some embodiments, the isolated nucleic acid encoding
an anti-BCMA CAR 16747P+slL15 polypeptide comprises
the sequence of SEQ ID NO: 42 (ATGAGCGTGCC-
TACCCAGGTGCTGGGACTGCTGCTGCTG
TGGCTGACAGACGCAAG
GTGCCAGGTGCAGCTGGTGGTGGAGAGCGGAG-
GAGGACTGGTGAAGCCAGGAGGAAGC
CTGAGGCTGTCCTGCGCCGCCTCTGGCTTCACCTT-
TAGCGACTACTATATCTCCTGGA
TCAGGCAGGCACCTGGCAAGGGACTG- GAGTGGGGTGTCCTACATCAGCTCCTCTGGC AGCTC-
CATCAAGTATGCCGACTCTGTGAAGGGCCGGTT-
CACCATCTCCAGAGATAAC
GCCAAGAATTCTCTGTACCTGCAGAT-
GAACAGCCTGCGGGCCGAGGACACAGCCGT
GTACTATTGCGCCAGAGAGGGCGGCAATTATGG-
CATGGACGTGTGGGGCCAGGGCA
CCACAGTGACCGTGTCTAGCGGCGG
CGGCGGCTCTGGAGGAGGAGGAAGCGGCGG
AGGAGGCGACATCCAGATGACACAGAGCC-
CATCCAGCGTGAGCGCCAGCGTGGGCG
ATAGGGTGACCATCACATGTCGCGCCTCCCAGGG-
CATCAACAATTGGCTGGTGTGGT
ACCAGCAGAAGCCAGGCAAGGCCCCCAAGCTGCT-
GATCTATGCAGCCACCTCCCTG                CAGTCTG-
GAGTGCCTAGCCGGTTCTCCGGATCTGGAAGCG-
GAACCGACTTTACCCTG
ACAATCAGCTCCCTGCAGCCAGAGGATTTTGCCA-
CATACTATTGTCAGCAGGCCAAC   TCCTTCCCCCC-
TACCTTTGGCCAGGGCACAAAGCTGGAGATCAA-
GACCACCACCCCT
GCACCAAGGCCCCCGACTCCCGCGCCCAC-
CATCGCGTCACAGCCTCTTAGCCTGCGA        CCG-
GAAGCATGCAGACCAGCTGCCGGTGGGGCGGTG-
CATACGAGAGGTTTGGACTT
CGCCTGCGATATCTA-
CATCTGGGCGCCCTTGGCCGGGACTTGT
GGGGTCCTTCTCCT      GTCACTGGTTATCACCCTT-
TACTGCAAACGGGGCAGAAAGAAACTCCTGTATAT-
ATT     CAAACAACCATTTATGAGACCAGTACAAAC-
TACTCAAGAGGAAGATGGCTGTAGCT
GCCGATTTCCAGAAGAAGAAGAAGGAGGATGT-
GAACTGAGAGTGAAGTTCAGCAG        GAGCGCA-
GACGCCCCCGCGTACCAGCAGGGCCAGAA
CCAGCTCTATAACGAGCTCA
ATCTAGGACGAAGAGAGGAGTAC-
GATGTTTTGGACAAGAGACGTGGCCGGGACCCT
GAGATGGGGG-
GAAAGCCGCAGAGAAGGAAGAACCCTCAG-
GAAGGCCTGTACAATG    AACTGCAGAAAGATAA-
GATGGCGGAGGCCTACAGTGAGATTGGG
ATGAAAGGCGA GCGCCGGAGGGGCAAGGGGCAC-
GATGGGCCTTTACCAGGGTGCTCAGTACAGCCACCA
AGGACACCTACGACGCCCTTCA-
CATGCAGGCCCTGCCCCCTCGCCGCGCGAAGCGA
TCAGGCAGCGGGGCGACAAATTTCAGCCTTCT-
GAAACAAGCAGGCGACGTGGAAGA
AAACCCCGGTCCAATGGCCT-
TACCAGTGACCGCCTTGCTCCTGCCGC
TGGCCTTGCT                                    GCTC-
CACGCCGCCAGGCCGAACTGGGT-
GAATGTAATAAGTGATTTGAAAAAAATTG
AAGATCTTATTCAATCTATGCATATTGATGCTACTT-
TATATACGGAAAGTGATGTTCA
CCCCAGTTGCAAAGTAACAGCAAT-
GAAGTGCTTTCTCTTGGAGTTACAAGTTATTTC
ACTTGAGTCCGGAGATGCAAGTATTCATGATA-
CAGTAGAAAATCTGATCATCCTAGC
AAACAACAGTTTGTCTTCTAATGG-
GAATGTAACAGAATCTGGATGCAAGAATGTG
AGGAACTGGAGGAAAAAAATATTAAAGAAT-
TTTTGCAGAGTTTTGTACATATTGTCC   AAATGTT-
CATCAACACTTCTTGA).

In some embodiments, the isolated nucleic acid encodes SEQ ID NO: 46 (MSVPTQVLGLLLLWLTDAR-CEIVMTQSPATLSVSPGERTTLSCRASQSVSSN-LAWYLQ            KPGQAPRLLIYGASTRATGI- PARFSGSGSGTEFILTISSLQSEDFAVYYCQQ
YNNWPITFG        QGTRLEIKGGGGSGGGGSGGG-
GEVQLVESGGGLVQPGRSLRLSCAASGFTFYDYAMH
WVRQAPGKGLEWVSGISWNSGYIG-
YADSVKGRFTISRDNAKNSLYLQMNSLRAEDTAL
YYCAKDNSYGKFYYGLDVWGQGTTVTVSSTTTPA-
PRPPTPAPTIASQPLSLRPEACRPA    AGGAVHTRGLD-
FACDIYIWAPLAGTCGVLLLSLVITLYCKRGRKKLLY-
IFKQPFMRPVQ
TTQEEDGCSCRFPEEEEGGCELRVKFSRSADAPA-
YQQGQNQLYNELNLGRREEYDVLD                    KRR-
GRDPEMGGKPQRRKNPQEGLYNELQKDKMAEAY-
SEIGMKGERRRGKGHDGLYQ
GLSTATKDTYDALHMQALPPRGS-
GATNFSLLKQAGDVEENPGPMALPVTALLLPLALLL
HAARPNWVNVISDLKKIEDLIQSMHIDAT-
LYTESDVHPSCKVTAMKCFLLELQVISLESG
DASIHDTVENLIILANNSLSSNGNVTESGCKE-
CEELEEKNIKEFLQSFVHIVQMFINTS*), an anti-CD20-CAR polypeptide comprising the following domains in order: a 3H7 binding domain, a CD8α hinge and transmembrane domain, a 4-1BB costimulation endodomain, a CD3ζ signaling domain, a P2A cleavage domain (GS-GATNFSLLKQAGDVEENPGP, SEQ ID NO: 47), a secretion signal, and a sIL15 domain.

In some embodiments, the isolated nucleic acid encodes SEQ ID NO: 48 (MSVPTQVLGLLLLWLTDAR-CEIVMTQSPATLSVSPGERTTLSCRASQSVSSN-LAWYLQ                KPGQAPRLLIYGASTRATGI-PARFSGSGSGTEFILTISSLQSEDFAVYYC
QQYNNWPITFG        QGTRLEIKGGGGSGGGGSGGG-
GEVQLVESGGGLVQPGRSLRLSCAASGFTFYDYAMH
WVRQAPGKGLEWVSGISWNSGYIG-
YADSVKGRFTISRDNAKNSLYLQMNSLRAEDTAL
YYCAKDNSYGKFYYGLDVWGQGTTVTVSSTTTPA-
PRPPTPAPTIASQPLSLRPEACRPA    AGGAVHTRGLD-
FACDIYIWAPLAGTCGVLLLSLVITLYCKRGRKKLLY-
IFKQPFMRPVQ
TTQEEDGCSCRFPEEEEGGCELRVKFSRSADAPA-
YQQGQNQLYNELNLGRREEYDVLD                    KRR-
GRDPEMGGKPQRRKNPQEGLYNELQKDKMAEAY-
SEIGMKGERRRGKGHDGLYQ
GLSTATKDTYDALHMQALPPRGS-
GATNFSLLKQAGDVEENPGPMRISKPHLRSISIQCYL
CLLLNSHFLTEAGIHVFILGCFSAGLPKTEANWVN-
VISDLKKIEDLIQSMHIDATLYTESD                    VHP-
SCKVTAMKCFLLELQVISLESGDASIHDTVEN-
LIILANNSLSSNGNVTESGCKECEEL
EEKNIKEFLQSFVHIVQMFINTS*), an anti-CD20-CAR polypeptide comprising the following domains in order: a 3H7 binding domain, a CD8α hinge and transmembrane domain, a 4-1BB costimulation endodomain, a CD3ζ signaling domain, a P2A cleavage domain of SEQ ID NO: 47, a secretion signal of SEQ ID NO: 49 (MRISKPHLRSI-SIQCYLCLLLNSHFLTEAG IHVFILGCFSAGLPKTEA), and a sIL15 domain.

In some embodiments, the isolated nucleic acid encoding an anti-CD20 CAR+sIL15 polypeptide comprises the sequence of SEQ ID NO: 50 (ATGTCCGTGCC-TACCCAGGTGCTGGGCCTGCTGCTGCTG
TGGCTGACCGACGCCAG            ATGCGAAATAGT-
GATGACGCAGTCTCCAGC-
CACCCTGTCTGTGTCTCCAGGGGAAAG        AAC-
CACCCTCTCCTGCAGGGCCAGTCAGAGTGTT
AGCAGCAACTTAGCCTGGTACCT
TCAGAAACCTGGCCAGGCTCCCAGGCTCCTCATC-
TATGGTGCATCCACCAGGGCCAC TGGTATCCCAGCCAGGTTCAGTGGCAGT
GGGTCTGGGACAGAGTTCATTCTCACCAT
CAGCAGCCTGCAGTCTGAAGATTTTGCAGTTTAT-
TACTGTCAGCAGTATAATAACTG GCCGAT-
CACCTTCGGCCAAGGGACACGGCTGGAGAT-
TAAAGGTGGAGGTGGATCTG
GAGGAGGAGGATCCGGTGGAGGAGGT-
GAAGTGCAACTGGTGGAGTCTGGGGGAGG
CTTGGTACAGCCTGGCAGGTCCCTGA-
GACTCTCCTGTGCAGCCTCTGGATTCACCTTT TAT-
GATTATGCCATGCACTGGGTCCGGCAAGCTCCAGG-
GAAGGGCCTGGAGTGGGT
CTCAGGTATTAGTTGGAATAGTGGTTACATAGGC-
TATGCGGACTCTGTGAAGGGCCG ATTCAC-
CATCTCCAGAGACAACGC-
CAAGAACTCCCTGTATCTGCAAATGAACAGTCT
GAGAGCTGAGGACACGGCCTTGTAT-
TACTGTGCAAAAGATAACAGCTATGGAAAGT
TCTACTACGGTTTGGACGTCTGGGGCCAAGGGAC-
CACGGTCACCGTCTCCTCAACCA
CGACGCCAGCGCCGCGACCACCAACACCGGCGCC-
CACCATCGCGTCGCAGCCCCTG
TCCCTGCGCCCAGAGGCGTGCCGGCCAGCGG
CGGGGGGCGCAGTGCACACGAGGGG
GCTGGACTTCGCCTGTGATATCTA-
CATCTGGGCGCCCTTGGCCGGGACTTGTGGGGT
CCTTCTCCTGTCACTGGTTATCACCCTT-
TACTGCAAACGGGGCAGAAAGAAACTCCT
GTATATATTCAAACAACCATTTATGAGACCAGTA-
CAAACTACTCAAGAGGAAGATG GCTGTAGCTGCC-
GATTTCCAGAAGAAGAAGAAGGAGGATGTGAACT-
GAGAGTGAAG
TTCAGCAGGAGCGCA-
GACGCCCCGCGTACCAGCAGGGCCAGA
ACCAGCTCTATAA CGAGCT-
CAATCTAGGACGAAGAGAGGAGTAC-
GATGTTTTGGACAAGAGACGTGGCC GGGACCCT-
GAGATGGGGGGAAAGCCGCAGAGAAGGA
AGAACCCTCAGGAAGGCCT GTACAAT-
GAACTGCAGAAAGATAAGATGGCGGAGGCCTA-
CAGTGAGATTGGGATGA AAGGCGAGCGCCG-
GAGGGGCAAGGGGCACGATGGCCTTT
ACCAGGGTCTCAGTACA GCCACCAAGGACACC-
TACGACGCCCTTCA-
CATGCAGGCCCTGCCCCCTCGCGGTAGC GGGGC-
TACGAACTTCTCCCTTCTTAAACAAGCG
GGAGACGTGGAAGAAAATCCCGG ACCTA
TGGCCTTACCAGTGACCGCCTTGCTCCTGCCGCTG
GCCTTGCTGCTCCACGCC
GCCAGGCCGAACTGGGTGAATGTAATAAGTGATTT-
GAAAAAAATTGAAGATCTTAT TCAATCTATGCATAT-
TGATGCTACTTTATATACGGAAAGTGATGTT-
CACCCCAGTTGC
AAAGTAACAGCAATGAAGTGCTTTCTCTTGGAGT-
TACAAGTTATTTCACTTGAGTCC GGAGATGCAAGT-
ATTCATGATACAGTAGAAAATCTGAT-
CATCCTAGCAAACAACAG
TTTGTCTTCTAATGGGAATGTAACAGAATCTG-
GATGCAAAGAATGTGAGGAACTGG
AGGAAAAAAATATTAAAGAAT-
TTTTGCAGAGTTTTGTACATATTGTCCAAATGTTCA
TCAACACTTCTTGA).

In some embodiments, the isolated nucleic acid encoding
an anti-CD20 CAR+sIL15 polypeptide comprises the
sequence of SEQ ID NO: 51 (ATGTCCGTGCC-
TACCCAGGTGCTGGGCCTGCTGCTGC
TGTGGCTGACCGACGCCAG ATGCGAAATAGT- GATGACGCAGTCTCCAGC-
CACCCTGTCTGTGTCTCCAGGGGAAAG AAC-
CACCCTCTCCTGCAGGGCCAGTCAGAG
TGTTAGCAGCAACTTAGCCTGGTACCT
TCAGAAACCTGGCCAGGCTCCCAGGCTCCTCATC-
TATGGTGCATCCACCAGGGCCAC
TGGTATCCCAGCCAGGTTCAGTGGCAG
TGGGTCTGGGACAGAGTTCATTCTCACCAT
CAGCAGCCTGCAGTCTGAAGATTTTGCAGTTTAT-
TACTGTCAGCAGTATAATAACTG GCCGAT-
CACCTTCGGCCAAGGGACACGGCTGGAGAT-
TAAAGGTGGAGGTGGATCTG
GAGGAGGAGGATCCGGTGGAGGAGGT-
GAAGTGCAACTGGTGGAGTCTGGGGGAGG
CTTGGTACAGCCTGGCAGGTCCCTGA-
GACTCTCCTGTGCAGCCTCTGGATTCACCTTT TAT-
GATTATGCCATGCACTGGGTCCGGCAAGCTCCAGG-
GAAGGGCCTGGAGTGGGT
CTCAGGTATTAGTTGGAATAGTGGTTACATAGGC-
TATGCGGACTCTGTGAAGGGCCG ATTCAC-
CATCTCCAGAGACAACGC-
CAAGAACTCCCTGTATCTGCAAATGAACAGTCT
GAGAGCTGAGGACACGGCCTTGTAT-
TACTGTGCAAAAGATAACAGCTATGGAAAGT
TCTACTACGGTTTGGACGTCTGGGGCCAAGGGAC-
CACGGTCACCGTCTCCTCAACCA
CGACGCCAGCGCCGCGACCACCAACACCGGCGCC-
CACCATCGCGTCGCAGCCCCTG
TCCCTGCGCCCAGAGGCGTGCCG
GCCAGCGGCGGGGGGCGCAGTGCACACGAGGGG
GCTGGACTTCGCCTGTGATATCTA-
CATCTGGGCGCCCTTGGCCGGGACTTGTGGGGT
CCTTCTCCTGTCACTGGTTATCACCCTT-
TACTGCAAACGGGGCAGAAAGAAACTCCT
GTATATATTCAAACAACCATTTATGAGACCAGTA-
CAAACTACTCAAGAGGAAGATG GCTGTAGCTGCC-
GATTTCCAGAAGAAGAAGAAGGAGGATGTGAACT-
GAGAGTGAAG
TTCAGCAGGAGCGCA-
GACGCCCCGCGTACCAGCAGGGCC
AGAACCAGCTCTATAA CGAGCT-
CAATCTAGGACGAAGAGAGGAGTAC-
GATGTTTTGGACAAGAGACGTGGCC GGGACCCT-
GAGATGGGGGGAAAGCCGCAG
AGAAGGAAGAACCCTCAGGAAGGCCT GTACAAT-
GAACTGCAGAAAGATAAGATGGCGGAGGCCTA-
CAGTGAGATTGGGATGA AAGGCGAGCGCCG-
GAGGGGCAAGGGGCACGATGGCCT
TTACCAGGGTCTCAGTACA GCCACCAAGGACACC-
TACGACGCCCTTCA-
CATGCAGGCCCTGCCCCCTCGCGGTAGC GGGGC-
TACGAACTTCTCCCTTCTTAAACA
AGCGGGAGACGTGGAAGAAAATCCCGG ACCTAT-
GAGAATTTCGAAACCACATTTGAGAAGTATTTC-
CATCCAGTGCTACTTGTG TTTACTTCTAAACAGT-
CATTTTCTAACTGAAGCTGGCATTCATGTCTT
CATTTTGGGC
TGTTTCAGTGCAGGGCTTCCTAAAACAGAAGC-
CAACTGGGTGAATGTAATAAGTGAT
TTGAAAAAAATTGAAGATCTTATTCAATCTATGCAT-
ATTGATGCTACTTTATATACG GAAAGTGATGTT-
CACCCCAGTTGCAAAGTAACAGCAAT-
GAAGTGCTTTCTCTTGGAG
TTACAAGTTATTTCACTTGAGTCCG-
GAGATGCAAGTATTCATGATACAGTAGAAAAT
CTGAT-
CATCCTAGCAAACAACAGTTTGTCTTCTAATGG- GAATGTAACAGAATCTGGA TGCAAAGAATGTGAG-
GAACTGGAGGAAAAAAATATT
AAAGAATTTTTGCAGAGTTT TGTACATATTGTC-
CAAATGTTCATCAACACTTCTTGA).

In some embodiments, the isolated nucleic acid encodes
SEQ ID NO: 57 (MSVPTQVLGLLLLWLTDAR-
CEIVMTQSPATLSVSPGERTTLSCRASQSVSSN-
LAWYLQ KPGQAPRLLIYGASTRATGI-
PARFSGSGSGTEFILTISSLQSEDFAVYY
CQQYNNWPITFG QGTRLEIKGGGGSGGGGSGGG-
GEVQLVESGGGLVQPGRSLRLSCAASGFTFYDYAMH
WVRQAPGKGLEWVSGISWNSGYIG-
YADSVKGRFTISRDNAKNSLYLQMNSLRAEDTAL
YYCAKDNSYGKFYYGLDVWGQGTTVTVSSTTTPA-
PRPPTPAPTIASQPLSLRPEACRPA AGGAVHTRGLD-
FACDIYIWAPLAGTCGVLLLSLVITLYCKRGRKKLLY-
IFKQPFMRPVQ
TTQEEDGCSCRFPEEEEGGCELRVKFSRSADAPA-
YQQGQNQLYNELNLGRREEYDVLD KRR-
GRDPEMGGKPQRRKNPQEGLYNELQKDKMAEAY-
SEIGMKGERRRGKGHDGLYQ
GLSTATKDTYDALHMQALPPR*), an anti-CD20-CAR
polypeptide comprising the following domains in order: a
3H7 binding domain, a CD8α hinge and transmembrane
domain, a 4-1BB costimulation endodomain, and a CD3ζ
signaling domain; and, via an internal ribosome entry site
(e.g., encoded by SEQ ID NO: 56) 3' of the region encoding
SEQ ID NO: 57, the isolated nucleic acid further encodes
SEQ ID NO: 58 (MALPVTALLLPLALLLHAARPNWVN-
VISDLKKIEDLIQSMHIDATLYTESDVHP
SCKVTAMKCFLLELQVISLESGDASIHDTVEN-
LIILANNSLSSNGNVTESGCKECEELEEK NIKE-
FLQSFVHIVQMFINTS*), a secretion signal of SEQ ID
NO: 33 and a sIL15 domain.

In some embodiments, the isolated nucleic acid encoding
an anti-CD20 CAR+sIL15 polypeptide comprises the
sequence of SEQ ID NO: 59 (ATGTCCGTGCC-
TACCCAGGTGCTGGGCCTGCTGCTGCTG
TGGCTGACCGACGCCAG ATGCGAAATAGT-
GATGACGCAGTCTCCAGC-
CACCCTGTCTGTGTCTCCAGGGGAAAG AAC-
CACCCTCTCCTGCAGGGCCAGTCAGA
GTGTTAGCAGCAACTTAGCCTGGTACCT
TCAGAAACCTGGCCAGGCTCCCAGGCTCCTCATC-
TATGGTGCATCCACCAGGGCCAC
TGGTATCCCAGCCAGGTTCAGTGGCAGT
GGGTCTGGGACAGAGTTCATTCTCACCAT
CAGCAGCCTGCAGTCTGAAGATTTTGCAGTTTAT-
TACTGTCAGCAGTATAATAACTG GCCGAT-
CACCTTCGGCCAAGGGACACGGCTGGAGAT-
TAAAGGTGGAGGTGGATCTG
GAGGAGGAGGATCCGGTGGAGGAGGT-
GAAGTGCAACTGGTGGAGTCTGGGGGAGG
CTTGGTACAGCCTGGCAGGTCCCTGA-
GACTCTCCTGTGCAGCCTCTGGATTCACCTTT TAT-
GATTATGCCATGCACTGGGTCCGGCAAGCTCCAGG-
GAAGGGCCTGGAGTGGGT
CTCAGGTATTAGTTGGAATAGTGGTTACATAGGC-
TATGCGGACTCTGTGAAGGGCCG ATTCAC-
CATCTCCAGAGACAACGC-
CAAGAACTCCCTGTATCTGCAAATGAACAGTCT
GAGAGCTGAGGACACGGCCTTGTAT-
TACTGTGCAAAAGATAACAGCTATGGAAAGT
TCTACTACGGTTTGGACGTCTGGGGCCAAGGGAC
CACGGTCACCGTCTCCTCAACCA
CGACGCCAGCGCCGCGACCACCAACACCGGCGCC-
CACCATCGCGTCGCAGCCCCTG TCCCTGCGCCCAGAGGCGT
GCCGGCCAGCGGCGGGGGGCGCAG
TGCACACGAGGGG GCTGGACTTCGCCTGTGA-
TATCTA-
CATCTGGGCGCCCTTGGCCGGGACTTGTGGGGT
CCTTCTCCTGTCACTGGTTATCACCCTT-
TACTGCAAACGGGGCAGAAAGAAACTCCT
GTATATATTCAAACAACCATTTATGAGACCAGTA-
CAAACTACTCAAGAGGAAGATG GCTGTAGCTGCC-
GATTTCCAGAAGAAGAAGAAGGAGGATGTGAACT-
GAGAGTGAAG
TTCAGCAGGAGCGCA-
GACGCCCCCGCGTACCAGCAGGG
CCAGAACCAGCTCTATAA CGAGCT-
CAATCTAGGACGAAGAGAGGAGTAC-
GATGTTTTGGACAAGAGACGTGGCC GGGACCCT-
GAGATGGGGGGGAAAGCCGCA
GAGAAGGAAGAACCCTCAGGAAGGCCT GTACAAT-
GAACTGCAGAAAGATAAGATGGCGGAGGCCTA-
CAGTGAGATTGGGATGA AAGGCGAGCGCCG-
GAGGGGCAAGGGGCACG
ATGGCCTTTACCAGGGTCTCAGTACA GCCAC-
CAAGGACACCTACGACGCCCTTCA-
CATGCAGGCCCTGCCCCCTCGCTAGAGT
ACTGCGGCCGCTACGTAAAT-
TCCGCCCCTCTCCCTCCCCCCCCCCTAACGT-
TACTGGC CGAAGCCGCTTG-
GAATAAGGCCGGTGTGCGTTTGTCTA
TATGTTATTTTCCACCATAT
TGCCGTCTTTTGGCAATGTGAGGGCCCG-
GAAACCTGGCCCTGTCTTCTTGACGAGCA
TTCCTAGGGGTCTTTCCCCTCTCGC-
CAAAGGAATGCAAGGTCTGTTGAATGTCGTGA
AGGAAGCAGTTCCTCTGGAAGCTTCTTGAA-
GACAAACAACGTCTGTAGCGACCCTTT
GCAGGCAGCGGAACCCCC-
CACCTGGCGACAGGTGCCTCTGCGGCCAAAAGC-
CACGT GTATAAGATACACCTGCAAAGGCGGCAC
AACCCCAGTGCCACGTTGTGAGTTGGAT
AGTTGTGGAAAGAGTCAAATGGCTCTCCT-
CAAGCGTATTCAACAAGGGGCTGAAGG
ATGCCCAGAAGGTACCCCATTGTATGGGATCT-
GATCTGGGGCCTCGGTGCACATGCT TTA-
CATGTGTTTAGTCGAGGT-
TAAAAAAACGTCTAGGCCCCCCGAACCACGGGGAC
GTGGTTTTCCTTTGAAAAACACGATGATATTAAT-
TAAGCCACCGCCATGGCCTTACC
AGTGACCGCCTTGCTCCTGCCGCT
GGCCTTGCTGCTCCACGCCGCCAGGCCGAACTG
GGTGAATGTAATAAGTGATTTGAAAAAAATTGAA-
GATCTTATTCAATCTATGCATAT TGATGCTACTT-
TATATACGGAAAGTGATGTT-
CACCCCAGTTGCAAAGTAACAGCAAT
GAAGTGCTTTCTCTTGGAGTTACAAGTTATTT-
CACTTGAGTCCGGAGATGCAAGTAT TCATGATA-
CAGTAGAAAATCTGAT-
CATCCTAGCAAACAACAGTTTGTCTTCTAATGG
GAATGTAACAGAATCTGGATGCAAAGAATGTGAG-
GAACTGGAGGAAAAAAATATTA AAGAAT-
TTTTGCAGAGTTTTGTACATATTGTCCAAATGTT-
CATCAACACTTCTTGA).

In some embodiments, the isolated nucleic acid is a linear
nucleic acid. In some embodiments, the isolated nucleic acid
is a circular nucleic acid. In some embodiments, the isolated
nucleic acid is a vector, such as a plasmid vector, an
adenoviral vector, an adeno-associated viral vector, a viral
vector, a retroviral vector, or a lentiviral vector. In some embodiments, the isolated nucleic acid, or an, e.g., contiguous, portion thereof containing the binding domain transmembrane domain and one or more signaling and/or costimulation endodomains is integrated into the genome of a host cell, such as a host γδ T cell. In an exemplary embodiment, the isolated nucleic acid is retroviral vector.

γδ T Cells:

Aspects of the invention include γδ T cells that functionally express an isolated nucleic acid described herein, and thereby expresses a CAR on the surface of the γδ T cell.

Aspects of the invention can additionally or alternatively include γδ T cells having in vitro or in vivo cytotoxic activity against a hematological tumor cell that exhibits cell surface expression of the tumor associated antigen (TAA). In some cases, the cytotoxic activity is innate activity. In some cases, the cytotoxicity is at least in part, significantly (>about 25%), or entirely, due to the presence of a CAR construct having a binding domain that specifically binds the TAA expressed on the surface of the hematological tumor cell. In some cases, the γδ T cells exhibit hematological tumor cell killing activity of said γδ T cell is greater than an innate level of in vitro and/or in vivo hematological tumor cell killing activity in a control γδ T cell. In some cases, the control γδ T cell does not comprise a CAR construct. In some cases, the control γδ T cell comprises a CAR construct lacking a binding domain described herein, a hinge region described herein, a transmembrane domain described herein, a signaling domain described herein, and/or a costimulation endodomain described herein.

In some cases, the cytotoxicity is at least in part, significantly (>about 25%), or entirely, due to the presence of a CAR construct having a binding domain that specifically binds CD20 or an epitope within CD20. In some cases, the γδ T cells functionally express a CD20 specific CAR encoded by an isolated nucleic acid described herein.

In some embodiments, γδ T cells described herein can exhibit HLA-restricted (e.g., HLA class I restricted) cytotoxicity. In other embodiments, most (>50%), substantially all (>90%), or all of the cytotoxic activity is not HLA-restricted (e.g., HLA class I restricted). HLA-restricted cytotoxic activity can be assessed by comparing in vitro cytotoxicity against an HLA (e.g., HLA class I) (null) tumor cell line versus in vitro cytotoxicity against an HLA+(e.g., HLA class I⁺) tumor cell line. In some embodiments, the HLA-restricted cytotoxic activity is at least in part, significantly (>25%), or entirely, provided by the use of a T cell Receptor-like binding domain. T cell receptor like binding domains are binding domains that specifically recognize the antigen when presented on the surface of a cell in complex with an MIC molecule. T cell Receptor-like binding domains are further described, e.g., in WO 2016/199141.

γδ T cells described herein can exhibit robust and/or persistent hematological tumor cell killing activity. In some cases, the hematological tumor cell killing activity can persist for at least about 6 days to 120 days, or for at least about 6 days to 180 days, from first contact with a hematological tumor cell. In some cases, the hematological tumor cell killing activity of a γδ T cell described herein, or a progeny thereof, can persist for at least about 6 days to 120 days, or for at least about 6 days to 180 days, from first contact with a hematological tumor cell, or from administration of the γδ T cell described herein. This persistent hematological tumor cell killing activity can be exhibited in vitro, in vivo, or both in vitro and in vivo.

Aspects of the invention can additionally or alternatively include γδ T cells that proliferate in response to contact with cells that exhibit cell surface expression, or overexpression, of the tumor associated antigen (TAA). The cells that exhibit cell surface expression of the tumor associated antigen (TAA) can be normal hematological cells, such as normal B cells. The cells that exhibit cell surface expression, or overexpression, of the tumor associated antigen (TAA) can be hematological tumor cells. In some cases, the proliferation is an innate activity. In some cases, the proliferation is at least in part, significantly (>about 20% or >about 25%), or entirely, due to the presence of a CAR construct having a binding domain that specifically binds the TAA expressed on the surface of the hematological cell or hematological tumor cell. In some cases, the γδ T cells exhibit a greater level of in vitro and/or in vivo proliferation as compared to a control γδ T cell. In some cases, the control γδ T cell does not comprise a CAR construct. In some cases, the control γδ T cell comprises a CAR construct lacking a binding domain described herein, a hinge region described herein, a transmembrane domain described herein, a signaling domain described herein, and/or a costimulation endodomain described herein.

In some cases, the proliferation is at least in part, significantly (>about 20 or >about 25%), or entirely, due to the presence of a CAR construct having a binding domain that specifically binds CD20 or an epitope within CD20. In some cases, γδ T cells exhibiting proliferation in response to contact with a hematological cell or hematological tumor cell that exhibits cell surface expression of CD20 functionally express a CD20 specific CAR encoded by an isolated nucleic acid described herein.

γδ T cells described herein can exhibit robust and/or persistent proliferation in a host organism that comprises the hematological cell or hematological tumor cell that exhibits cell surface expression, or overexpression, of the tumor associated antigen (TAA). In some cases, the proliferation can persist for at least about 6 days to 120 days, or for at least about 6 days to 180 days, from first contact with a hematological tumor cell or from a date of administration of the γδ T cell to the host organism. In some cases, the proliferation of a γδ T cell described herein, or a progeny thereof, in the host organism that comprises the hematological cell or hematological tumor cell that exhibits cell surface expression, or overexpression, of the tumor associated antigen (TAA) can persist for at least about 6 days to 120 days, or for at least about 6 days to 180 days, from first contact with a hematological cell or hematological tumor cell or from the date of first administration of the γδ T cell to the host organism. In some cases, the proliferation in the host organism is at least in part, significantly (>about 20% or >about 25%), or entirely, due to the presence of a CAR construct having a binding domain that specifically binds CD20 or an epitope within CD20. In some cases, γδ T cells exhibiting proliferation in the host organism comprising a hematological cell or hematological tumor cell that exhibits cell surface expression of CD20 functionally express a CD20 specific CAR encoded by an isolated nucleic acid described herein.

In some embodiments, the γδ T cells described herein express, or persistently express, pro-inflammatory cytokines such as tumor necrosis factor alpha or interferon gamma after contact with the hematological cell or hematological tumor cell. In some embodiments, the γδ T cells described herein, or progeny thereof, express, or persistently express, pro-inflammatory cytokines such as tumor necrosis factor alpha or interferon gamma after contact with the hematological cell or hematological tumor cell, e.g., in a host organism comprising the hematological cell or hematological tumor cell.

In some embodiments, the γδ T cell, or a pharmaceutical composition containing the γδ T cell, exhibits essentially no, or no graft versus host response when introduced into an allogeneic host. In some embodiments, the γδ T cell, or a pharmaceutical composition containing the γδ T cell, exhibits a clinically acceptable level of graft versus host response when introduced into an allogeneic host. In some embodiments, a clinically acceptable level is an amount of graft versus host response that does not require cessation of a γδ T cell treatment to achieve a therapeutically effective treatment. In some embodiments, a clinically acceptable level of graft versus host response (GvHD) is an acute response that is less severe than Grade C according to an applicable IBMTR grading scale. The severity of acute graft versus host response is determined by an assessment of the degree of involvement of the skin, liver, and gastrointestinal tract. The stages of individual organ involvement are combined to produce an overall grade, which has prognostic significance. Grade I(A) GvHD is characterized as mild disease, grade II(B) GvHD as moderate, grade III(C) as severe, and grade IV(D) life-threatening. The IBMTR grading system defines the severity of acute GvHD as follows (Rowlings et al., Br J Haematol 1997; 97:855):

Grade A—Stage 1 skin involvement alone (maculopapular rash over <25 percent of the body) with no liver or gastrointestinal involvement Grade B—Stage 2 skin involvement; Stage 1 to 2 gut or liver involvement Grade C—Stage 3 involvement of any organ system (generalized erythroderma; bilirubin 6.1 to 15.0 mg/dL; diarrhea 1500 to 2000 mL/day)

Grade D—Stage 4 involvement of any organ system (generalized erythroderma with bullous formation; bilirubin >15 mg/dL; diarrhea >2000 mL/day OR pain OR ileus).

See also, Schoemans et al., *Bone Marrow Transplantation* volume 53, pages 1401-1415 (2018), e.g., at Tables 1 and 2, which discloses criteria for assessing and grading acute GvHD.

In some embodiments, the γδ T cell, or a pharmaceutical composition containing the γδ T cell, exhibits reduced or substantially reduced graft versus host response when introduced into an allogeneic host as compared to a graft versus host response exhibited by control αβ T cells, or a control pharmaceutical composition comprising the control αβ T cells, administered to an allogeneic host. In some cases, the control αβ T cell is an allogeneic non-engineered control αβ T cell. In some cases, the control αβ T cell does not comprise a CAR or does not comprise the same CAR as a reference γδ T cell.

The γδ T cells described herein can be δ1, δ2, δ3, or δ4 γT cells, or combinations thereof. In some cases, the γδ T cells are mostly (>50%), substantially (>90%), essentially all, or entirely 62-γδ T cells. In some cases, the γδ T cells are mostly (>50%), substantially (>90%), essentially all, or entirely δ1 γδ T cells.

γδ T cells can be obtained from an allogeneic or an autologous donor. The γδ T cells can be, partially or entirely purified, or not purified, and expanded ex vivo. Methods and compositions for ex vivo expansion include, without limitation, those described in WO 2017/197347. The expansion may be performed before or after, or before and after, a CAR construct is introduced into the γδ T cell (s).

γδ T cells described herein can be stored, e.g., cryopreserved, for use in adoptive cell transfer.

Methods of Inhibiting or Killing Tumor Cells

One or multiple non-engineered, γδ T-cell populations, engineered, γδ T-cell populations, and/or admixtures thereof, having cytotoxic activity against a hematological tumor cell can be administered to a subject in any order or simultaneously. If simultaneously, the multiple non-engineered, γδ T-cell population, engineered, γδ T-cell population, and/or admixtures thereof, of the invention can be provided in a single, unified form, such as an intravenous injection, or in multiple forms, for example, as multiple intravenous infusions, s.c, injections or pills. The non-engineered, γδ T-cell population, engineered, γδ T-cell population, and/or admixtures thereof, of the invention can be packed together or separately, in a single package or in a plurality of packages. One or all of the non-engineered γδ T-cell population, engineered γδ T-cell population, and/or admixtures thereof, of the invention can be given in multiple doses. If not simultaneous, the timing between the multiple doses may vary to as much as about a week, a month, two months, three months, four months, five months, six months, or about a year. In some cases, a non-engineered, enriched γδ T-cell population, an engineered, enriched γδ T-cell population, and/or admixtures thereof, of the invention can proliferate within a subject's body, in vivo, after administration to a subject. One or more non-engineered γδ T-cell populations, one or more engineered γδ T-cell populations, and/or admixtures thereof, can be frozen to provide cells for multiple treatments with the same cell preparation. One or more non-engineered γδ T-cell populations, one or more engineered γδ T-cell populations, and/or admixtures thereof, of the disclosure, and pharmaceutical compositions comprising the same, can be packaged as a kit. A kit may include instructions (e.g., written instructions) on the use of the non-engineered γδ T-cell population, the engineered γδ T-cell population, and/or admixtures thereof, and compositions comprising the same.

In some cases, a method of treating a hematological cancer comprises administering to a subject a therapeutically-effective amount of a non-engineered γδ T-cell population, an engineered γδ T-cell population, and/or admixtures thereof, wherein the administration treats the hematological cancer. In some embodiments the therapeutically-effective amount of the non-engineered, γδ T-cell population, the engineered γδ T-cell population, and/or admixtures thereof, is administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In some embodiments the therapeutically-effective amount of the non-engineered γδ T-cell population, the engineered γδ T-cell population, and/or admixtures thereof, is administered for at least one week. In some embodiments the therapeutically-effective amount of the non-engineered γδ T-cell population, the engineered γδ T-cell population, and/or admixtures thereof, is administered for at least two weeks.

A non-engineered γδ T-cell population, an engineered γδ T-cell population, and/or admixtures thereof, described herein can be administered before, during, or after the occurrence of a disease or condition, and the timing of administering a pharmaceutical composition containing the γδ T-cell population can vary. For example, the γδ T-cell population can be used as a prophylactic and can be administered continuously to subjects with a propensity to conditions or diseases in order to lessen a likelihood of the occurrence of the disease or condition. The initial administration can be via any route practical, such as by any route described herein using any formulation described herein. In some examples, the administration of a γδ T-cell population of the disclosure is an intravenous administration. One or multiple dosages of the γδ T-cell population can be administered as soon as is practicable after the onset of a hematological cancer and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. In some embodiments, one or multiple dosages of the γδ T-cell population can be administered years after onset of the cancer and before or after other treatments.

In some embodiments, the γδ T-cell population is administered simultaneously or sequentially with one or more methods to elevate common gamma chain cytokine(s). As used herein, "one or more methods to elevate common gamma chain cytokine(s): refers to a method, or combination of methods, that alters the physiological state of a subject, such that at least one common gamma chain cytokine level is elevated in the subject. In some embodiments, the method elevates the level of one or more common gamma chain cytokine(s) selected from the group consisting of IL-2, IL-7, and IL-15, preferably wherein the method elevates the level of IL-15 in the subject. In some embodiments, the method comprises lymphodepletion. In some embodiments, the method comprises administering one or more common gamma chain cytokine(s) to the subject. In some cases, IL-2, IL-7, and/or IL-15, preferably IL-15, are administered. In some embodiments, the method comprises secreting common gamma chain cytokine(s) from an administered, e.g., γδ T cell. In some cases, IL-2, IL-7, and/or IL-15, preferably IL-15, are secreted.

In some embodiments, the administering one or more methods to elevate common gamma chain cytokine(s) comprises lymphodepletion before introducing the γδ T cell(s). In some embodiments, the administering one or more methods to elevate common gamma chain cytokine(s) comprises administering simultaneously with introducing the γδ T cell(s) or sequentially an amount of common gamma chain cytokine(s) effective to increase proliferation, cytotoxic activity, persistence, or the combination thereof of the introduced γδ T cell(s), preferably wherein the method comprises administering IL-2 or one or more mimetics thereof, more preferably wherein the method comprises administering IL-15 or one or more mimetics thereof. The amount of administered common gamma chain cytokine(s) can be an amount effective to increase proliferation, cytotoxic activity, persistence, or the combination thereof of the introduced γδ T cell(s) before and/or after introducing the γδ T cell(s). Exemplary amounts of IL-15 include, without limitation between 0.01-10 µg/kg/dose every 24 hours for IL-15. Exemplary amounts of IL-2 include, without limitation, between about $3 \times 10^6$ and about $22 \times 10^6$ units every 8-48 hours. For example, the dosing regimen for IL2 in RCC is 600,000 International Units/kg (0.037 mg/kg) IV q8 hr infused over 15 minutes for a maximum 14 doses.

In some embodiments, the administering one or more methods to elevate common gamma chain cytokine(s) comprises lymphodepletion before administering the γδ T cell(s) and administering simultaneously with introducing the γδ T cell(s) or sequentially an amount of common gamma chain cytokine(s) effective to increase proliferation, cytotoxic activity, persistence, or the combination thereof of the introduced γδ T cell(s).

EXAMPLES

Example 1

Figure 3:
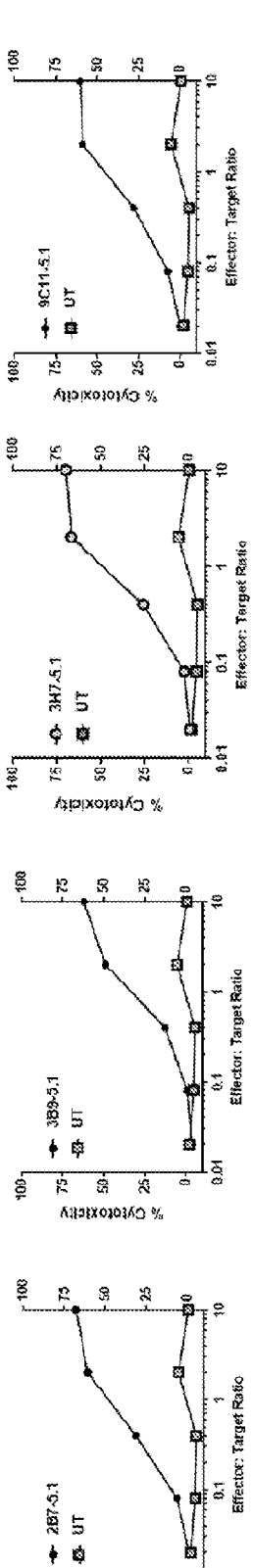
FIG. 3 illustrates induction of apoptosis CD20-expressing normal B cells by untransduced Vδ1 cells and Vδ1 cells transduced with various CD20-specific CAR constructs.

Human PBMCs at $1 \times 10^6$/mL were activated in a modified cell culture media on pre-coated anti-Vδ1 antibody D1-08 or D1-35 (see, WO 2017/197347) for 5 days in the presence of IL-2 (100 U/mL) in 24-well plates (Costar). On day 5, cell cultures were transduced with γ-retroviral constructs encoding chimeric antigen receptors (2B7-5.1, SEQ ID NO: 11; 3B9-5.1, SEQ ID NO:9; 3H7-5.1, SEQ ID NO:10; 9C11-5.1, SEQ ID NO:12) in the presence of retronectin. On day 6 cells were returned to the modified cell culture media and further expanded with feeding and IL-2 replacement as needed. On days 17, 18 or 19, cells were harvested, and remaining up T cells were depleted using AutoMACS® kit (Miltenyi Biotec). Purity of 76 cell population and transduction efficiency was assessed by FACS. In parallel, untransduced cell cultures were expanded in the same manner, without adding the retroviral supernatant. As shown in FIG. 3, untransduced expanded Vδ1 cells from multiple donors are not cytotoxic to normal B cells from an allogeneic donor. Introduction of CD20 CAR into Vδ1 cells conferred robust cytotoxicity to these cells against normal B cells. Cytotoxicity was measured as % Annexin V+ cells by flow cytometry in 4 hr assay.

Example 2

Figure 4:
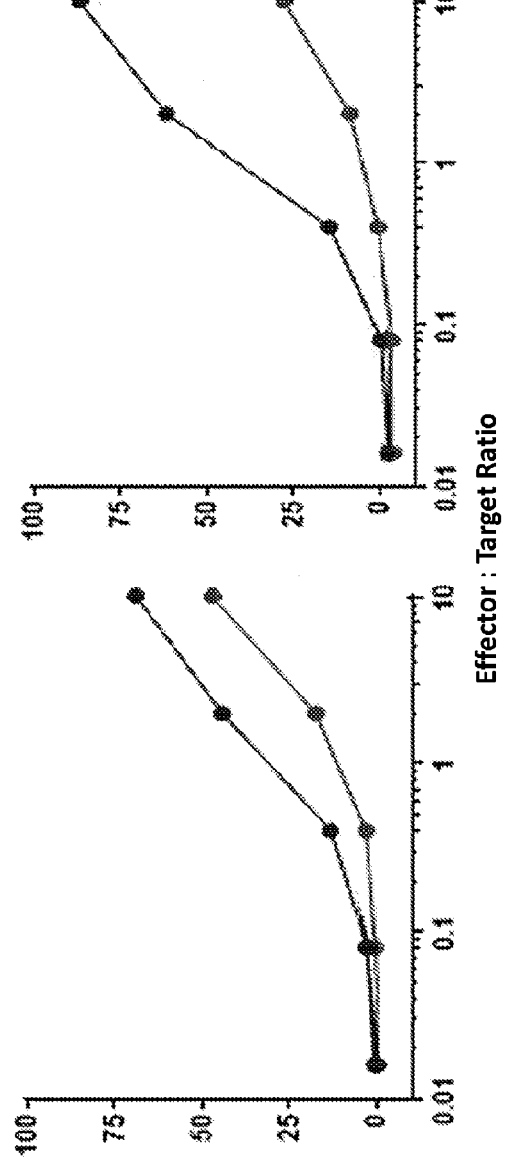
FIG. 4 illustrates potent cytotoxic activity of CD20-specific CAR γδ T cells against lymphoma cell lines

Vδ1 cells were activated, transduced and expanded in the same manner as described above. 3H7 CAR construct SEQ ID NO:10 was used to demonstrate cytotoxicity against two CD20+ cell lines—Daudi and Raji. As shown in FIG. 4, introduction of the CAR potentiated innate cytotoxicity of unengineered Vδ1 cells.

Example 3

Figure 5:
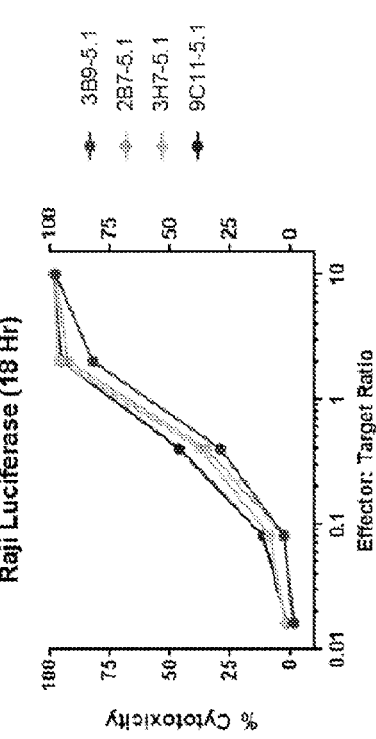
FIG. 5 illustrates cytotoxicity of engineered CAR γδ T cells described herein against Raji cells. Top: Binding domains containing CDRs of 3B9, 2B7, 3H7, and 9C11 are tested in a CAR construct encoding a 4-1BB costimulation endodomain and CD3ζ signaling domain.

Vδ1 cells were activated, transduced and expanded in the same manner as described above. Four different constructs (SEQ ID NOs:9, 10, 11, 12) were introduced into Vδ1 cells during expansion and tested against Raji-Luc cells. Cytotoxicity was determined by total luminescence measurement after adding luminescent substrate D-Luciferin (Perkin Elmer) after 18 hr co-incubation at varying E/T ratios. As shown in FIG. 5, anti-CD20 CAR cells comprising a 4-1BB costimulation endodomain described herein exhibited robust cell killing activity against Raji cells.

Example 4

CARs constructs were made with several different domains and CD20 binding domains (3H7-CD3z, SEQ ID NO:20; 3H7-5.1, SEQ ID NO:10; and 3H7-CD27z, SEQ ID NO:8). CAR constructs were introduced as describe above and cytotoxicity was tested against Raji-Luc cells as described in previous example (18 hr cytotoxicity at varying E/T ratios). FIG. 6 illustrates robust cell killing activity against Raji cells with different signaling and/or costimulation endodomain(s).

Example 5

Figure 7:
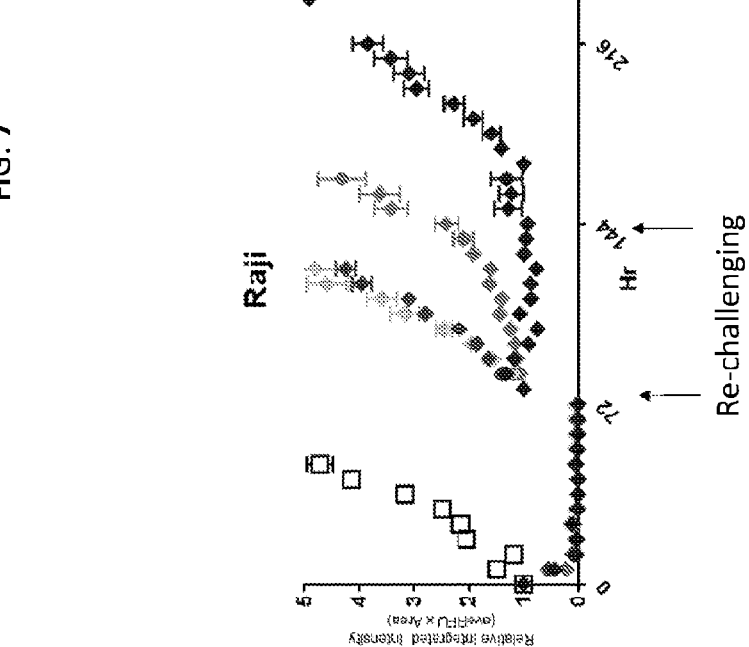
FIG. 7 illustrates results of a cytotoxicity assay with re-challenge of the indicated γδ T cells. Arrows indicate time of re-administration.

Various CAR constructs were introduced into expanded Vδ1 cells and tested in long-term cytotoxicity assay with target cell re-challenging (Serial Killing) using IncuCyte® instrument. Briefly, Raji cells were labeled with NucRed reagent and total fluorescence of cells was recorded over time. Cells were co-incubated at E/T ratio of 3 for 72 hours in growth media without any cytokine addition. At the end of 72 h, cultures were re-challenged with another dose of Raji cells, and monitored for killing. This procedure was repeated with cultures where Raji cells were cleared by 144 h. FIG. 7. 3H7-ICOSz is a construct in which 4-1BB costimulation endodomain is replaced with an ICOS endodomain (WLTKKKYSSSVHDPNGEYMFMRAVN-TAKKSRLTDVTL (SEQ ID NO: 354)).

Example 6

Figure 8:
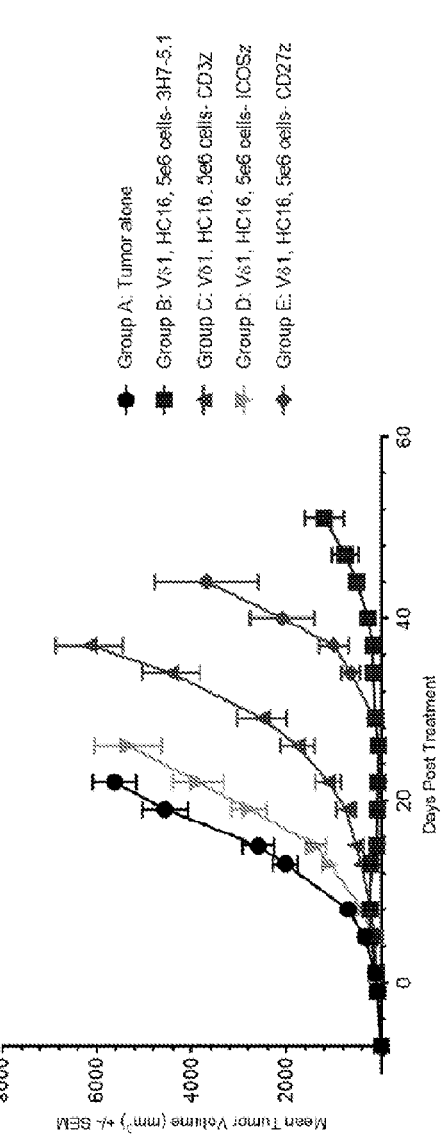
FIG. 8 illustrates in vivo efficacy of γδ T cell s described herein in a subcutaneous Raji cell NOD scid gamma (NSG) mouse model.

Raji cells were subcutaneously implanted into NSG mice (Jackson Labs). When tumors reached about 100 mm$^3$ size, animals were treated with 5×10$^6$ Vδ1 CD20 CAR+cells to compare efficacy of various costimulation endodomains ("co-stim" or "costim") in vivo. Animals were dosed concomitantly with IL-2 (60,000 U/dose) 3 times a week throughout the study. As shown in FIG. 8, the tested constructs exhibited robust in vivo efficacy in treating hematological tumors in NSG mice. Without wishing to be bound by theory, it is hypothesized that the optimized CAR constructs of 3H7-5.1, 3H7-CD3z, and 3H7-CD27z exhibit superior in vivo tumor control, proliferation, activation, persistence, and/or cytotoxicity as compared to non-optimized CAR constructs.

Example 7

Figure 9:
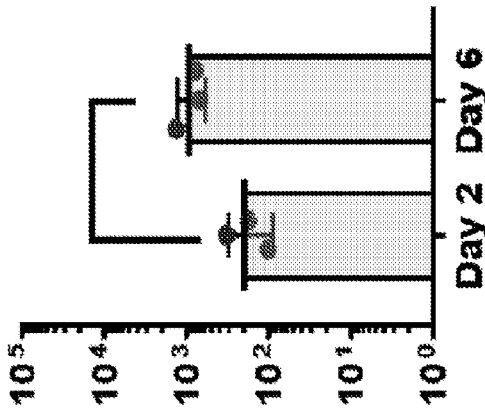
FIG. 9 illustrates enumeration of intratumoral CD20-specific γδ CAR-T cells in vivo indicating in vivo expansion of 76 CAR-T cells and tumor clearance.
Figure 10:
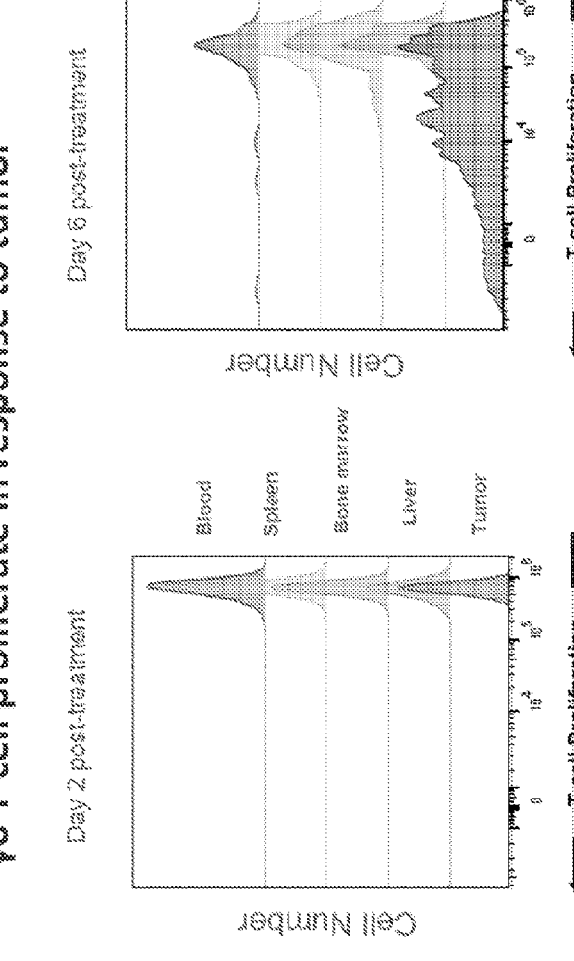
FIG. 10 illustrates in vivo proliferation of CD20-specific γδ CAR-T cells in CD20⁺ lymphoma tumor and other organs.

Raji cells were subcutaneously implanted into NSG mice (Jackson Labs). When tumors reached about 100 mm$^3$ animals were treated with 5×10$^6$ Vδ1 CD20 CAR+cells that were pre-labeled with CellTrace Violet. On Day 2 and Day 6 tumors and various other organs were extracted, digested and the resulting cell suspension analyzed for (A) presence of γδ T cells and Raji cells (FIG. 9) and (B) proliferation of γδ cells as evidenced by CellTrace Violet dye dilution (FIG. 10). Animals received concomitant IL-2 (60,000 U/dose) 3 times a week until Day 6. As shown in FIG. 9, the introduced γδ T cell s robustly increased in the intratumoral milieu, and facilitated a significant decrease in the ratio of tumor cells to γδ T cells from day 2 to day 6. As shown in FIG. 10, γδ T cells proliferated robustly and preferentially in the intratumoral space.

Example 8

Figure 11:
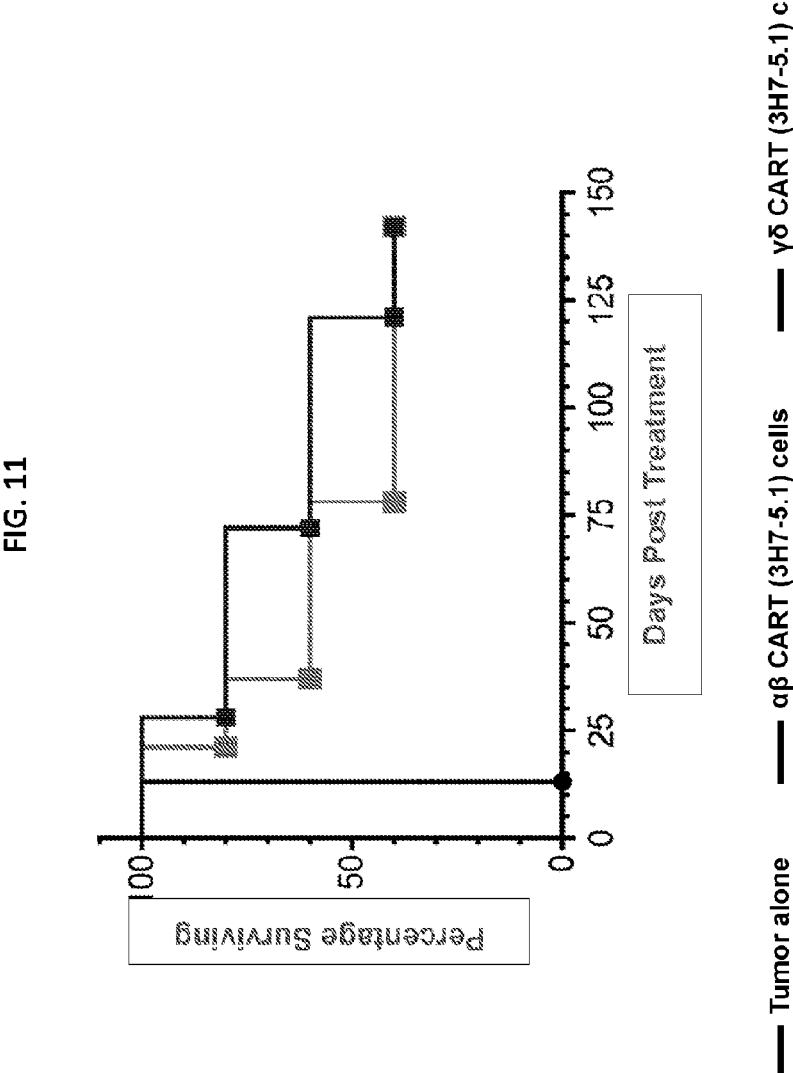
FIG. 11 illustrates in vivo efficacy of γδ T cells described herein in a disseminated Raji cell NOD scid gamma (NSG) mouse model.

NSG mice were inoculated with Raji-Luc cells (0.5 mln/animal). On Day 4 animals were treated with 8.7×10$^6$ Vδ1 CAR+cells (SEQ ID NO: 10) or 6.8×10$^5$ αβ T cells transduced with the same construct. Survival of animals was monitored over the period of 140 days. All animals received 3 doses of IL-2 (60,000/animal) on Day 0, Day 1, and Day 2. FIG. 11. As shown in FIG. 11, administration of γδ T cell s described herein increased the survival of subjects having a hematological cancer.

Example 9

Figure 12:
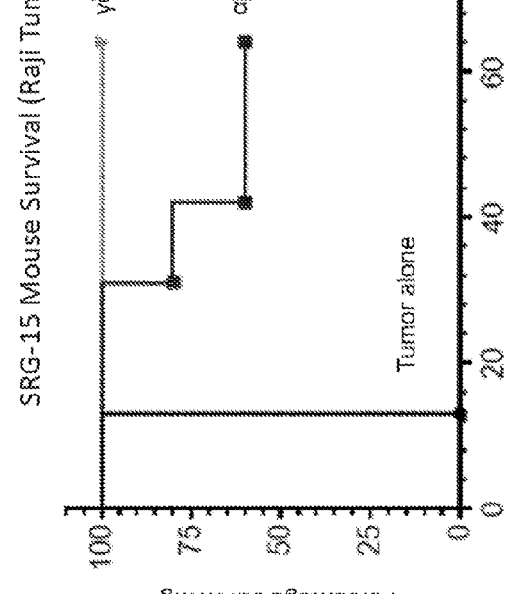
FIG. 12 illustrates effective treatment of a disseminated Raji tumor with CD20-specific γδ CAR-T cells in the SRG-15 mouse model that expresses human IL-15, without induction of a Graft versus Host (GVH) response. In contrast, CD20-specific αβ CAR-T cells elicit a lethal GVH response.

SRG-15 mice (Herndler-Brandstetter et al., PNAS, 2017) expressing human IL-15 were inoculated with Raji-Luc cells (0.5×10$^6$/animal). On Day 4 animals were treated with 20.2×10$^6$ of Vδ1 CAR+cells (SEQ ID NO: 10) or 1.9×10$^6$ of αβ T cells transduced with the same construct. Survival of animals was monitored over the period of 70 days. FIG. 12.

As shown in FIG. 12, the introduced γδ T cell s did not elicit a GvHD response. In contrast, introduced αβ T cells elicited a GvHD response.

Example 10

Figure 14:
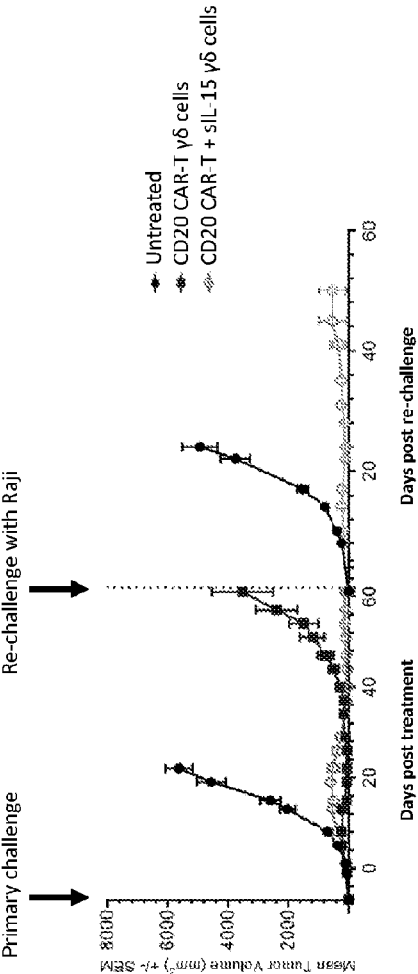
FIG. 14 illustrates therapeutic efficacy and persistence of CD20 CAR Vδ1 T cells expressing sIL15 in NSG mice subcutaneously implanted with Raji cells and subsequently re-challenged (Day 62) with Raji cells at a different implantation site.

NSG mice were inoculated with Raji cells (1×10$^6$/animal) subcutaneously in right hind flank. When tumor volumes reached ~100 mm$^3$ mice were randomized and treated with 5×10$^6$ Vδ1 CAR T cells encoding CD20 CAR or CD20 CAR and soluble IL-15. Animals were concomitantly dosed with IL-2 (60,000 U/dose, Peprotech, 3× week) throughout the study. Four animals from CD20+sIL15 CAR T group that had no measurable tumor at Day 62 were re-challenged with 1×10$^6$ Raji cells subcutaneously on opposite (left) flank. A control group of animals was also included to demonstrate tumor growth kinetics. Results are illustrated in FIG. 14. As shown in FIG. 14, administration of γδ CAR-T cells having a nucleic acid construct that encodes a heterologous soluble IL-15 produced a persistent anti-tumor effect that lasted beyond 60 days (e.g., from 60 to 110 days).

Example 11

Figure 15:
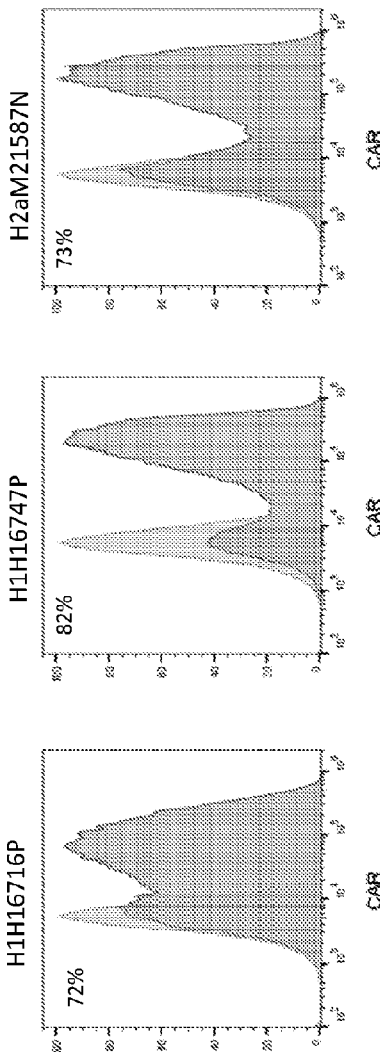
FIG. 15 illustrates transduction efficiency of Vδ1 cells with indicated anti-B cell maturation antigen (BCMA) scFv CAR constructs. BCMA is also known as tumor necrosis factor receptor superfamily member 17 (TNFRSF17).
Figure 16:
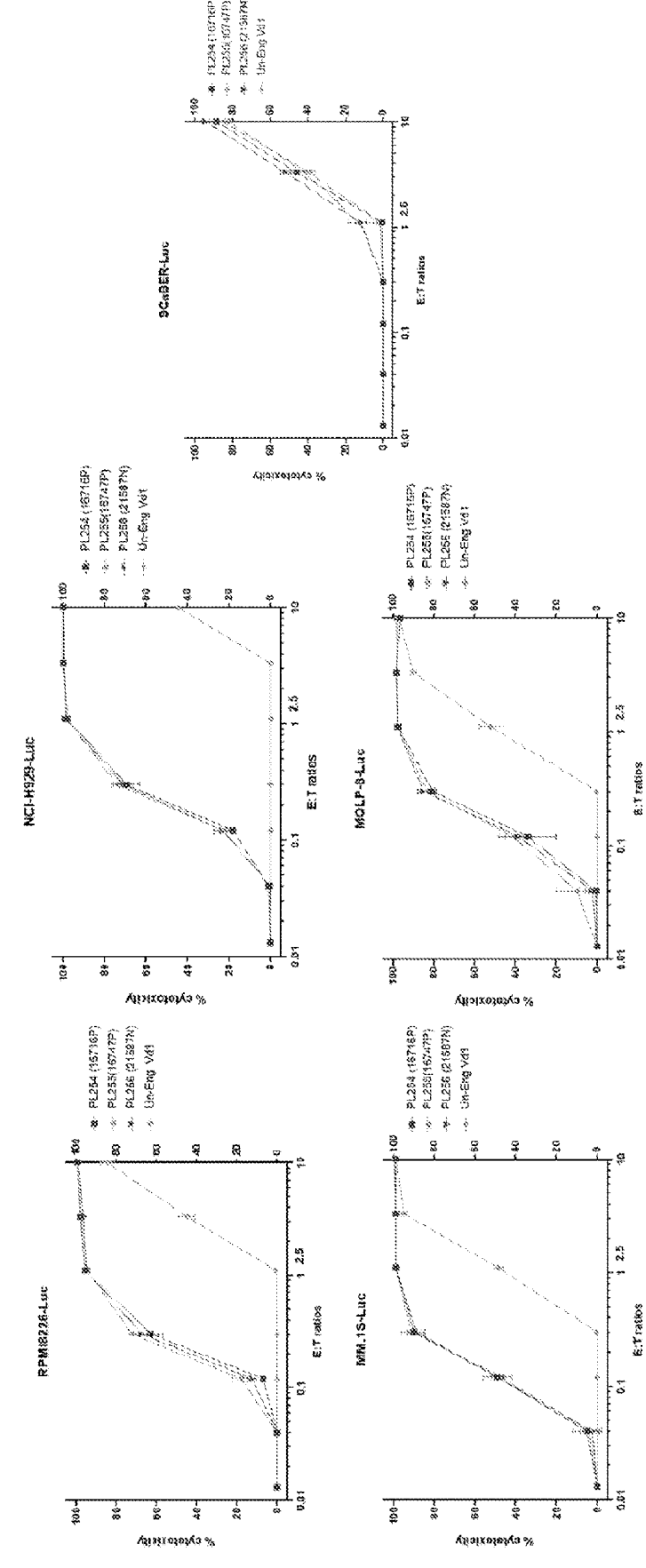
FIG. 16 illustrates cytotoxic activity of Vδ1 T cells transduced with various anti-BCMA CAR constructs against a panel of multiple myeloma BCMA+ cell lines. The SCABER-Luc cell line is a control cell line that is BCMA-negative.

Human PBMCs at 1×10$^6$/mL in growth media were activated in a 24-well plate (Costar) pre-coated with anti-Vδ1 antibody D1-08 or D1-35 for 5 days in the presence of IL-2 (100 U/mL). On day 5, cell cultures were transduced with γ-retroviral constructs encoding BCMA chimeric antigen receptor (SEQ ID NOs: 35-38) in the presence of retronectin. On day 6 cells were returned to growth media and further expanded with feeding and IL-2 replacement as needed. On days 17, 18 or 19, cells were harvested, and remaining αβ T cells were depleted using AutoMACS@ kit (Miltenyi Biotec). Purity of γδ cell population and transduction efficiency was assessed by FACS (FIG. 15). Briefly, CAR-T cells were stained by incubating cells with 1 μg/mL of soluble recombinant biotinylated BCMA (Acro Biosystems). Detection of binding was performed using streptavidin-BV421 at the manufacturer-suggested dilution of 1:500. In parallel, untransduced cell cultures were expanded in the same manner, without adding the retroviral supernatant. Expanded cells were tested in the in vitro cytotoxicity assay on BCMA positive cell lines. As shown in FIG. 16 and FIG. 17, untransduced expanded Vδ1 cells elicited some degree of cytotoxicity against multiple myeloma and Burkitt lymphoma cell lines that are known to express BCMA to various degrees. This cytotoxicity was potentiated by introduction of BCMA CAR constructs. Cytotoxicity was determined by total luminescence measurement in 96-well plates, by adding luminescent substrate D-Luciferin (Perkin Elmer) after 18 hr co-incubation at indicated E/T ratios. A BCMA negative SCABER cell line was used as control.

Example 12

Figure 18:
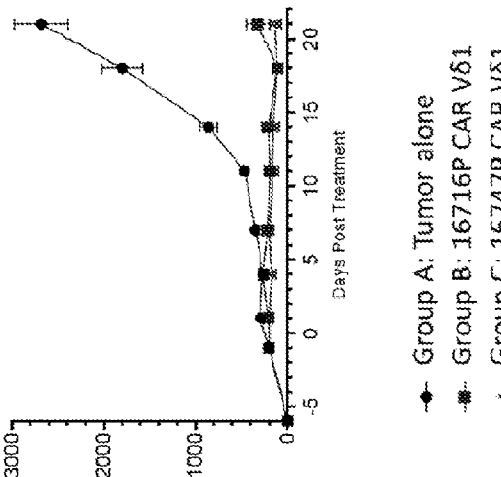
FIG. 18 illustrates in vivo therapeutic efficacy of anti-BCMA CAR Vδ1 T cells against subcutaneously implanted NCI-H929 cells.

NCI-H929 multiple myeloma cells (1×10$^6$/animal) were subcutaneously implanted into NSG mice (Jackson Labs). When tumors reached about 200 mm$^3$ size, animals were treated with 5×10$^6$ Vδ1 BCMA CAR+cells to compare efficacy of 16716P and 16747P scFv derived CAR constructs in vivo. Animals were dosed concomitantly with IL-2 (13,000 IU/dose, Proleukin®) 3 times a week throughout the study. Results are illustrated in FIG. 18. As shown in FIG. 19, anti-BCMA CAR+cells exhibited robust in vivo tumor burden control.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A δ1 γδ T cell comprising:

a. a nucleic acid encoding a chimeric antigen receptor (CAR), wherein the CAR comprises (i) a binding domain that specifically binds to CD20;

(ii) a CD8α hinge domain;

(iii) a CD8 α transmembrane domain;

(iv) a costimulatory signaling region; and (v) a CD3α signaling domain; or b. a polypeptide comprising a CAR comprising an amino acid sequence encoded by the nucleic acid of (a);

wherein the δ1 γδ T cell functionally expresses the binding domain of the polypeptide or the nucleic acid encoded CAR on the surface of the δ1 γδ T cell, and wherein the binding domain comprises anti-CD20 antibody 3H7; or the binding domain comprises the complementary determining regions of anti-CD20 antibody 3H7.

2. The δ1 γδ T cell of claim 1, wherein the (i)-(v) are in 5' to 3' order.

3. The δ1 γδ T cell of claim 1, wherein the binding domain encodes:

a. a heavy chain variable region (HCVR) sequence and a light chain variable region (LCVR) sequence, wherein the HCVR and LCVR sequences are SEQ ID NO: 99 and 107 respectively; or b. a heavy chain complementarity determining region 1, 2, and 3 sequence of SEQ ID NOs: 101, 103, and 105 respectively, and a light chain complementarity determining region 1, 2, and 3 sequence of SEQ ID NOs: 109, 111, and 113 respectively.

4. The δ1 γδ T cell of claim 1, wherein the CAR comprises:

a. a CD8α hinge domain comprising SEQ ID NO:1 (PTPAPTIASQPLSLRPEACRPAAGGAVHTRGLD-FACDIY) or SEQ ID NO:2 (TTTPAPRPPTPAPTIA-SQPLSLRPEACRPAAGGAVHTRGLDFACDIY);

b. a CD8α transmembrane domain comprising SEQ ID NO:3 (IWAPLAGTCGVLLLSLVITLYC); and/or c. a CD33 signaling domain comprising:

(i)
                                    SEQ ID NO: 4
(RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKDT

YDALHMQALPPR);

or (ii)
                                    SEQ ID NO: 5
(RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTY

DALHMQALPPR).

5. The δ1 γδ T cell of claim 4, wherein the CAR comprises:

a. a 4-1BB costimulatory signaling region comprising SEQ ID NO:6 (KRGRKKLLY-IFKQPFMRPVQTTQEEDGCSCRFPEEEEGGCEL); or b. a CD27 costimulatory signaling region comprising SEQ ID NO:7, (QRRKYRSNKGESPVEPAEPCHY-SCPREEEGSTIPIQEDYRKPEPACSP), or wherein the isolated nucleic acid encodes the 4-1BB costimulatory signaling region comprising SEQ ID NO:6 and the CD27 costimulatory signaling region comprising SEQ ID NO:7.

6. The δ1 γδ T cell of claim 1, wherein the nucleic acid further encodes:

a. a secreted cytokine;

b. a secreted common gamma chain interleukin;

c. a secreted IL-15; or d. a secreted common gamma chain interleukin, preferably IL 15, and a multi-cistronic linker region amino terminal to the interleukin or interleukin secretion signal.

7. The δ1 γδ T cell of claim 1, wherein the nucleic acid encodes SEQ ID NO:10.

8. The δ1 γδ T cell of claim 7, wherein the nucleic acid comprises the sequence of SEQ ID NO:14.

9. The δ1 γδ T cell of claim 1, wherein the δ1 γδ T cell proliferates in response to contact with cells that exhibit cell surface expression, or overexpression, of CD20; wherein the cells that exhibit cell surface expression of CD20 are normal hematological cells.

10. The δ1 γδ T cell of claim 9, wherein the cells that exhibit cell surface expression of CD20 are normal B cells.

11. The δ1 γδ T cell of claim 1, wherein the δ1 γδ T cell proliferates in response to contact with cells that exhibit cell surface expression, or overexpression, of CD20; wherein the cells that exhibit cell surface expression of CD20 are hematological tumor cells.

12. A cell population comprising a plurality of δ1 γδ T cells according to claim 1.

13. The cell population of claim 12, wherein the plurality comprises a least about $10^8$ δ1 γδ T cells, preferablyor from about $10^{11}$ δ1 γδ T cells to about $10^{11}$ δ1 γδ T cells.

14. The cell population of claim 12, wherein the plurality comprises composition that is at least 60%, 80%, or from about 60% or 80% to about 90% or 95% δ1 γδ T cells.

15. A method of making the δ1 γδ T cell of claim 1 or the cell population of claims 12, wherein the method comprises transfecting δ1 γδ T cell(s) with a construct comprising the nucleic acid as defined in claim 1.

16. The method of claim 15, wherein the method comprises retroviral transduction.

17. The method of claim 15, wherein the method comprises ex vivo expansion of the δ1 γδ T cell(s), wherein the ex vivo expansion is performed before transfection and/or after transfection of the nucleic acid.

18. A pharmaceutical composition comprising a pharmaceutically acceptable excipient and the δ1 γδ T cell of claim 1 or the cell population of claim 12.

19. A method of killing a hematological tumor cell that exhibits cell surface expression of CD20, the method comprising contacting the hematological tumor cell with a tumor cell killing effective amount of the δ1 γδ T cell of claim 1; the cell population of claim 12; or the pharmaceutical composition of claim 18.

20. The method of claim 19, wherein the method comprises introducing a therapeutically effective amount of the δ1 γδ T cell(s) or the pharmaceutical composition into a host organism comprising the hematological tumor cell.

21. The method of claim 20, wherein the method comprises introducing into a host organism comprising the hematological tumor cell a therapeutically effective amount of the δ1γδ T cell(s) or the pharmaceutical composition and simultaneously or sequentially administering one or more methods to elevate common gamma chain cytokine(s).

22. The method of claim 21, wherein the administering one or more methods to elevate common gamma chain cytokine(s) comprises administering simultaneously with introducing the δ1 γδ T cell(s) or sequentially an amount of common gamma chain cytokine(s) effective to increase proliferation, cytotoxic activity, persistence, or the combination thereof of the introduced δ1 γδ T cell(s).

23. The method of claim 22, wherein the one or more methods to elevate common gamma chain cytokine(s) comprise administering an amount of common gamma chain cytokine(s) effective to increase proliferation, cytotoxic activity, persistence, or the combination thereof of the introduced δ1 γδ T cell(s) before and/or after introducing the δ1 γδ T cell(s).

24. The method of claim 21, wherein the one or more methods to elevate common gamma chain cytokine(s) comprises lymphodepletion before introducing the δ1 γδ T cell(s).

25. The method of claim 21, wherein the one or more methods to elevate common gamma chain cytokine(s) comprises secretion of one or more common gamma chain cytokine(s) from the introduced δ1 γδ T cell(s).

26. The method of claim 20, wherein the method reduces the in vivo tumor burden in the host organism, and/or increases the mean survival time of the host organism as compared to a control organism, wherein the control organism is not treated with the δ1 γδ T cell(s) or the pharmaceutical composition.

27. The method of claim 19, wherein the method is a method of treating cancer in a subject in need thereof.

28. A method of treating cancer in a subject in need thereof, the method comprising:
   a. administering a therapeutically effective amount of δ1γδ T cells according to claim 1, wherein the cancer comprises hematological tumor cells that exhibit cell surface expression of CD20.

29. The method of claim 28, wherein the method comprises simultaneously with the administering of δ1 γδ T cells or sequentially, administering one or more methods to elevate common gamma chain cytokine(s).

30. The method of claim 28 or 29, wherein the method comprises performing a plurality of administrations of the δ1 γδ T cells, wherein the interval between the plurality of administrations is at least about a week, or at least about 2, 3, 4, 5, 6, 7, 8, or 12 weeks, and/or no more than once every 6 or 12 months.

31. The δ1 γδ T cell of claim 1, wherein the costimulatory signaling region is a 4-1BB (CD137) costimulatory signaling region or a CD27 costimulatory signaling region.

32. The δ1 γδ T cell of claim 6, wherein the IL-15 in c comprises the sequence of SEQ ID NO:34.

33. The δ1 γδ T cell of claim 32, wherein the IL-15 comprises the sequence of SEQ ID NO: 34 operably linked to a secretion signal sequence of SEQ ID NO:33, or the IL-15 comprises the sequence of SEQ ID NO:34 operably linked to a secretion signal sequence of SEQ ID NO:49.

34. The δ1 γδ T cell of claim 6, wherein the secreted common gamma chain interleukin in d is IL-15.

35. The δ1 γδ T cell of claim 6, wherein the multicistronic linker region in d comprises any one of SEQ ID NOs:43-45, 47, or 52-55 or a combination thereof, or encodes an internal ribosome entry site, e.g., SEQ ID NO: 56 or 60.

36. The method of claim 22, wherein the method further comprises administering IL-2.

37. The method of claim 22, wherein the method further comprises administering IL-15.

* * * * *

SEQUENCE LISTING

```
<160> NUMBER OF SEQ ID NOS: 370

<210> SEQ ID NO 1
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Pro Thr Pro Ala Pro Thr Ile Ala Ser Gln Pro Leu Ser Leu Arg Pro
1               5                   10                  15

Glu Ala Cys Arg Pro Ala Ala Gly Gly Ala Val His Thr Arg Gly Leu
            20                  25                  30

Asp Phe Ala Cys Asp Ile Tyr
        35

<210> SEQ ID NO 2
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 3
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 4
```

```
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 5
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 6
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Lys Arg Gly Arg Lys Lys Leu Leu Tyr Ile Phe Lys Gln Pro Phe Met
```

-continued

```
1               5                    10                    15

Arg Pro Val Gln Thr Thr Gln Glu Glu Asp Gly Cys Ser Cys Arg Phe
            20                    25                    30

Pro Glu Glu Glu Glu Gly Gly Cys Glu Leu
        35                    40
```

<210> SEQ ID NO 7
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Gln Arg Arg Lys Tyr Arg Ser Asn Lys Gly Glu Ser Pro Val Glu Pro
1               5                    10                    15

Ala Glu Pro Cys His Tyr Ser Cys Pro Arg Glu Glu Glu Gly Ser Thr
            20                    25                    30

Ile Pro Ile Gln Glu Asp Tyr Arg Lys Pro Glu Pro Ala Cys Ser Pro
        35                    40                    45
```

<210> SEQ ID NO 8
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Met Ser Val Pro Thr Gln Val Leu Gly Leu Leu Leu Leu Trp Leu Thr
1               5                    10                    15

Asp Ala Arg Cys Glu Ile Val Met Thr Gln Ser Pro Ala Thr Leu Ser
            20                    25                    30

Val Ser Pro Gly Glu Arg Thr Thr Leu Ser Cys Arg Ala Ser Gln Ser
        35                    40                    45

Val Ser Ser Asn Leu Ala Trp Tyr Leu Gln Lys Pro Gly Gln Ala Pro
    50                    55                    60

Arg Leu Leu Ile Tyr Gly Ala Ser Thr Arg Ala Thr Gly Ile Pro Ala
65                    70                    75                    80

Arg Phe Ser Gly Ser Gly Ser Gly Thr Glu Phe Ile Leu Thr Ile Ser
            85                    90                    95

Ser Leu Gln Ser Glu Asp Phe Ala Val Tyr Tyr Cys Gln Gln Tyr Asn
            100                   105                   110

Asn Trp Pro Ile Thr Phe Gly Gln Gly Thr Arg Leu Glu Ile Lys Gly
        115                   120                   125

Gly Gly Gly Ser Gly Gly Gly Gly Ser Gly Gly Gly Gly Glu Val Gln
    130                   135                   140

Leu Val Glu Ser Gly Gly Gly Leu Val Gln Pro Gly Arg Ser Leu Arg
145                   150                   155                   160

Leu Ser Cys Ala Ala Ser Gly Phe Thr Phe Tyr Asp Tyr Ala Met His
            165                   170                   175

Trp Val Arg Gln Ala Pro Gly Lys Gly Leu Glu Trp Val Ser Gly Ile
            180                   185                   190

Ser Trp Asn Ser Gly Tyr Ile Gly Tyr Ala Asp Ser Val Lys Gly Arg
            195                   200                   205
```

-continued

```
Phe Thr Ile Ser Arg Asp Asn Ala Lys Asn Ser Leu Tyr Leu Gln Met
    210                 215                 220

Asn Ser Leu Arg Ala Glu Asp Thr Ala Leu Tyr Tyr Cys Ala Lys Asp
225                 230                 235                 240

Asn Ser Tyr Gly Lys Phe Tyr Tyr Gly Leu Asp Val Trp Gly Gln Gly
                245                 250                 255

Thr Thr Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Gln Arg Arg Lys
                325                 330                 335

Tyr Arg Ser Asn Lys Gly Glu Ser Pro Val Glu Pro Ala Glu Pro Cys
                340                 345                 350

His Tyr Ser Cys Pro Arg Glu Glu Glu Gly Ser Thr Ile Pro Ile Gln
                355                 360                 365

Glu Asp Tyr Arg Lys Pro Glu Pro Ala Cys Ser Pro Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Gln Arg Arg
                420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

```
<210> SEQ ID NO 9
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Ser Val Pro Thr Gln Val Leu Gly Leu Leu Leu Leu Trp Leu Thr
1               5                   10                  15

Asp Ala Arg Cys Glu Ile Val Met Thr Gln Ser Pro Ala Thr Leu Ser
                20                  25                  30

Val Ser Pro Gly Glu Arg Ala Thr Leu Ser Cys Arg Ala Ser Gln Ser
            35                  40                  45

Val Ser Ser Asn Leu Ala Trp Tyr Gln Gln Lys Pro Gly Gln Ala Pro
    50                  55                  60
```

```
Arg Leu Leu Ile Tyr Gly Thr Ser Thr Arg Ala Thr Gly Ile Pro Ala
65               70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Leu Thr Phe Gly Gly Gly Thr Lys Val Glu Ile Lys Gly
        115                 120                 125

Gly Gly Gly Ser Gly Gly Gly Ser Gly Gly Gly Gly Glu Val Gln
    130                 135                 140

Leu Val Glu Ser Gly Gly Gly Leu Val Gln Pro Gly Arg Ser Leu Arg
145                 150                 155                 160

Leu Ser Cys Val Ala Ser Gly Phe Thr Phe Asn Asp Tyr Ala Met His
            165                 170                 175

Trp Val Arg Gln Ala Pro Gly Lys Gly Leu Glu Trp Val Ser Val Ile
            180                 185                 190

Ser Trp Asn Ser Asp Ser Ile Gly Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

His Ser Leu Arg Ala Glu Asp Thr Ala Leu Tyr Tyr Cys Ala Lys Asp
225                 230                 235                 240

Asn His Tyr Gly Ser Gly Ser Tyr Tyr Tyr Tyr Gln Tyr Gly Met Asp
            245                 250                 255

Val Trp Gly Gln Gly Thr Thr Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Gln Arg Arg Lys
        420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
```

-continued

```
                 485                   490

<210> SEQ ID NO 10
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Ser Val Pro Thr Gln Val Leu Gly Leu Leu Leu Trp Leu Thr
1               5                   10                  15

Asp Ala Arg Cys Glu Ile Val Met Thr Gln Ser Pro Ala Thr Leu Ser
            20                  25                  30

Val Ser Pro Gly Glu Arg Thr Thr Leu Ser Cys Arg Ala Ser Gln Ser
        35                  40                  45

Val Ser Ser Asn Leu Ala Trp Tyr Leu Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Ile Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Ile Thr Phe Gly Gln Gly Thr Arg Leu Glu Ile Lys Gly
        115                 120                 125

Gly Gly Gly Ser Gly Gly Gly Gly Ser Gly Gly Gly Gly Glu Val Gln
    130                 135                 140

Leu Val Glu Ser Gly Gly Gly Leu Val Gln Pro Gly Arg Ser Leu Arg
145                 150                 155                 160

Leu Ser Cys Ala Ala Ser Gly Phe Thr Phe Tyr Asp Tyr Ala Met His
                165                 170                 175

Trp Val Arg Gln Ala Pro Gly Lys Gly Leu Glu Trp Val Ser Gly Ile
            180                 185                 190

Ser Trp Asn Ser Gly Tyr Ile Gly Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Leu Tyr Tyr Cys Ala Lys Asp
225                 230                 235                 240

Asn Ser Tyr Gly Lys Phe Tyr Tyr Gly Leu Asp Val Trp Gly Gln Gly
                245                 250                 255

Thr Thr Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350
```

-continued

```
Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
        370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Gln Arg Arg Lys Asn Pro Gln Glu Gly
                420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

```
<210> SEQ ID NO 11
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

```
Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Ala Thr Leu Ser
                20                  25                  30

Leu Ser Pro Gly Glu Arg Ala Ala Leu Ser Cys Arg Ala Ser Gln Ser
        35                  40                  45

Val Ser Asn Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
                100                 105                 110

Asn Trp Pro Leu Thr Phe Gly Gly Gly Thr Lys Val Glu Ile Arg Gly
        115                 120                 125

Gly Gly Gly Ser Gly Gly Gly Gly Ser Gly Gly Gly Gly Glu Val Gln
        130                 135                 140

Leu Val Glu Ser Gly Gly Gly Leu Val Gln Pro Gly Arg Ser Leu Arg
145                 150                 155                 160

Leu Ser Cys Ala Ala Ser Gly Phe Thr Phe Arg Asp Tyr Thr Met His
                165                 170                 175

Trp Val Arg Gln Gly Pro Gly Lys Gly Leu Glu Trp Val Ser Gly Ile
                180                 185                 190

Ser Trp Asn Ser Asp Tyr Ile Gly Tyr Ala Asp Ser Val Lys Gly Arg
        195                 200                 205
```

```
Phe Thr Ile Ser Arg Asp Asn Ala Lys Asn Ser Leu Tyr Leu Gln Met
    210             215             220

Asn Ser Leu Arg Val Glu Asp Thr Ala Leu Tyr Tyr Cys Ala Lys Leu
225             230             235             240

Ser Gly Thr Tyr Arg Asp Tyr Phe Tyr Gly Val Asp Val Trp Gly Gln
            245             250             255

Gly Thr Thr Val Thr Val Ser Ser Thr Thr Thr Pro Ala Pro Arg Pro
            260             265             270

Pro Thr Pro Ala Pro Thr Ile Ala Ser Gln Pro Leu Ser Leu Arg Pro
            275             280             285

Glu Ala Cys Arg Pro Ala Ala Gly Gly Ala Val His Thr Arg Gly Leu
    290             295             300

Asp Phe Ala Cys Asp Ile Tyr Ile Trp Ala Pro Leu Ala Gly Thr Cys
305             310             315             320

Gly Val Leu Leu Leu Ser Leu Val Ile Thr Leu Tyr Cys Lys Arg Gly
            325             330             335

Arg Lys Lys Leu Leu Tyr Ile Phe Lys Gln Pro Phe Met Arg Pro Val
            340             345             350

Gln Thr Thr Gln Glu Glu Asp Gly Cys Ser Cys Arg Phe Pro Glu Glu
            355             360             365

Glu Glu Gly Gly Cys Glu Leu Arg Val Lys Phe Ser Arg Ser Ala Asp
    370             375             380

Ala Pro Ala Tyr Gln Gln Gly Gln Asn Gln Leu Tyr Asn Glu Leu Asn
385             390             395             400

Leu Gly Arg Arg Glu Glu Tyr Asp Val Leu Asp Lys Arg Arg Gly Arg
            405             410             415

Asp Pro Glu Met Gly Gly Lys Pro Gln Arg Arg Lys Asn Pro Gln Glu
            420             425             430

Gly Leu Tyr Asn Glu Leu Gln Lys Asp Lys Met Ala Glu Ala Tyr Ser
            435             440             445

Glu Ile Gly Met Lys Gly Glu Arg Arg Arg Gly Lys Gly His Asp Gly
    450             455             460

Leu Tyr Gln Gly Leu Ser Thr Ala Thr Lys Asp Thr Tyr Asp Ala Leu
465             470             475             480

His Met Gln Ala Leu Pro Pro Arg
                485
```

<210> SEQ ID NO 12
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 12

```
Met Ser Val Pro Thr Gln Val Leu Gly Leu Leu Leu Leu Trp Leu Thr
1               5               10              15

Asp Ala Arg Cys Glu Ile Val Val Thr Gln Ser Pro Ala Thr Leu Ser
            20              25              30

Leu Ser Pro Gly Glu Arg Ala Thr Leu Ser Cys Arg Thr Ser Gln Thr
            35              40              45

Thr Thr Ser Tyr Leu Ala Trp Tyr Arg Gln Lys Pro Gly Gln Ala Pro
    50              55              60

Arg Leu Leu Ile Tyr Asp Ala Ser Asn Arg Ala Ala Gly Ile Pro Ala
```

-continued

```
                 65                    70                    75                    80

Arg Phe Ser Gly Ser Gly Ser Gly Thr Asp Phe Thr Leu Thr Ile Asn
                 85                    90                    95

Ser Leu Glu Pro Glu Asp Phe Ala Val Tyr Tyr Cys Gln Leu Arg Thr
                100                   105                   110

Asn Trp Ile Thr Phe Gly Gln Gly Thr Arg Leu Glu Ile Lys Gly Gly
                115                   120                   125

Gly Gly Ser Gly Gly Gly Gly Ser Gly Gly Gly Gln Val Gln Leu
                130                   135                   140

Val Glu Ser Gly Gly Asp Ser Val Lys Pro Gly Gly Ser Leu Arg Leu
145                   150                   155                   160

Ser Cys Ala Ala Ser Gly Phe Thr Phe Ser Asp Ser Tyr Met Thr Trp
                165                   170                   175

Ile Arg Gln Ala Pro Gly Lys Gly Leu Glu Trp Val Ser Phe Ile Ser
                180                   185                   190

Ser Ser Gly Ser Thr Ile Tyr Tyr Ala Asp Ser Val Lys Gly Arg Phe
                195                   200                   205

Thr Ile Ser Arg Asp Asn Val Lys Lys Ser Leu Tyr Leu Gln Met Asn
                210                   215                   220

Arg Leu Arg Ala Glu Asp Thr Ala Val Tyr Tyr Cys Ala Arg Glu Glu
225                   230                   235                   240

Pro Gly Asn Tyr Val Tyr Tyr Gly Met Asp Val Trp Gly Gln Gly Thr
                245                   250                   255

Thr Val Thr Val Ser Ser Thr Thr Thr Pro Ala Pro Arg Pro Pro Thr
                260                   265                   270

Pro Ala Pro Thr Ile Ala Ser Gln Pro Leu Ser Leu Arg Pro Glu Ala
                275                   280                   285

Cys Arg Pro Ala Ala Gly Gly Ala Val His Thr Arg Gly Leu Asp Phe
                290                   295                   300

Ala Cys Asp Ile Tyr Ile Trp Ala Pro Leu Ala Gly Thr Cys Gly Val
305                   310                   315                   320

Leu Leu Leu Ser Leu Val Ile Thr Leu Tyr Cys Lys Arg Gly Arg Lys
                325                   330                   335

Lys Leu Leu Tyr Ile Phe Lys Gln Pro Phe Met Arg Pro Val Gln Thr
                340                   345                   350

Thr Gln Glu Glu Asp Gly Cys Ser Cys Arg Phe Pro Glu Glu Glu Glu
                355                   360                   365

Gly Gly Cys Glu Leu Arg Val Lys Phe Ser Arg Ser Ala Asp Ala Pro
                370                   375                   380

Ala Tyr Gln Gln Gly Gln Asn Gln Leu Tyr Asn Glu Leu Asn Leu Gly
385                   390                   395                   400

Arg Arg Glu Glu Tyr Asp Val Leu Asp Lys Arg Arg Gly Arg Asp Pro
                405                   410                   415

Glu Met Gly Gly Lys Pro Gln Arg Arg Lys Asn Pro Gln Glu Gly Leu
                420                   425                   430

Tyr Asn Glu Leu Gln Lys Asp Lys Met Ala Glu Ala Tyr Ser Glu Ile
                435                   440                   445

Gly Met Lys Gly Glu Arg Arg Arg Gly Lys Gly His Asp Gly Leu Tyr
                450                   455                   460

Gln Gly Leu Ser Thr Ala Thr Lys Asp Thr Tyr Asp Ala Leu His Met
465                   470                   475                   480

Gln Ala Leu Pro Pro Arg
                485
```

```
<210> SEQ ID NO 13
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
atgtccgtgc ctacccaggt gctgggcctg ctgctgctgt ggctgaccga cgccagatgc      60
gaaatagtga tgacgcagtc tccagccacc ctgtctgtgt ctccagggga aagaaccacc     120
ctctcctgca gggccagtca gagtgttagc agcaacttag cctggtacct tcagaaacct     180
ggccaggctc ccaggctcct catctatggt gcatccacca gggccactgg tatcccagcc     240
aggttcagtg gcagtgggtc tgggacagag ttcattctca ccatcagcag cctgcagtct     300
gaagattttg cagtttatta ctgtcagcag tataataact ggccgatcac cttcggccaa     360
gggacacggc tggagattaa aggtggaggt ggatctggag gaggaggatc cggtggagga     420
ggtgaagtgc aactggtgga gtctggggga ggcttggtac agcctggcag gtccctgaga     480
ctctcctgtg cagcctctgg attcaccttt tatgattatg ccatgcactg ggtccggcaa     540
gctccaggga agggcctgga gtgggtctca ggtattagtt ggaatagtgg ttacataggc     600
tatgcggact ctgtgaaggg ccgattcacc atctccagag acaacgccaa gaactccctg     660
tatctgcaaa tgaacagtct gagagctgag gacacggcct gtattactg tgcaaaagat      720 aacagctatg gaaagttcta ctacggtttg gacgtctggg gccaagggac cacggtcacc     780
gtctcctcaa ccacgacgcc agcgccgcga ccaccaacac cggcgcccac catcgcgtcg     840
cagcccctgt ccctgcgccc agaggcgtgc cggccagcgg cggggggcgc agtgcacacg     900 aggggggctgg acttcgcctg tgatatctac atctgggcgc ccttggccgg acttgtggg      960 gtccttctcc tgtcactggt tatcacccctt tactgccaac gacgcaagta ccgctccaat    1020
aaaggagagt caccagtaga acccgccgaa ccttgtcact attcatgtcc acgcgaagag    1080
gagggttcaa cgatccctat tcaggaagat tacagaaagc cggaacctgc ttgtagccc     1140 agagtgaagt tcagccgcag cgccgacgcc cctgcctacc agcagggcca gaaccagctg    1200
tataacgagc tgaacctggg caggcgggag gaatacgacg tgctggacaa gcgcagaggc    1260
cgggaccctg agatgggcgg caagccccag aggcggaaga acccccagga aggcctgtat    1320
aacgaactgc agaaagacaa gatggccgag gcctacagcg agatcggcat gaagggcgag    1380
cggcgacgcg gcaagggcca cgacggcctg taccagggcc tgtccaccgc caccaaggac    1440
acctacgacg ccctgcacat gcaggccctg cctccccgtt ag                       1482

<210> SEQ ID NO 14
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
atgtccgtgc ctacccaggt gctgggcctg ctgctgctgt ggctgaccga cgccagatgc      60
gaaatagtga tgacgcagtc tccagccacc ctgtctgtgt ctccagggga aagaaccacc     120
```

```
ctctcctgca gggccagtca gagtgttagc agcaacttag cctggtacct tcagaaacct        180
ggccaggctc ccaggctcct catctatggt gcatccacca gggccactgg tatcccagcc        240
aggttcagtg gcagtgggtc tgggacagag ttcattctca ccatcagcag cctgcagtct        300
gaagattttg cagtttatta ctgtcagcag tataataact ggccgatcac cttcggccaa        360
gggacacggc tggagattaa aggtggaggt ggatctggag gaggaggatc cggtggagga        420
ggtgaagtgc aactggtgga gtctggggga ggcttggtac agcctggcag gtccctgaga        480
ctctcctgtg cagcctctgg attcaccttt tatgattatg ccatgcactg ggtccggcaa        540
gctccaggga agggcctgga gtgggtctca ggtattagtt ggaatagtgg ttacataggc        600
tatgcggact ctgtgaaggg ccgattcacc atctccagag acaacgccaa gaactccctg        660
tatctgcaaa tgaacagtct gagagctgag gacacggcct gtattactg tgcaaaagat        720 aacagctatg gaaagttcta ctacggtttg gacgtctggg gccaagggac cacggtcacc        780
gtctcctcaa ccacgacgcc agcgccgcga ccaccaacac cggcgcccac catcgcgtcg        840
cagcccctgt ccctgcgccc agaggcgtgc cggccagcgg cggggggcgc agtgcacacg        900 aggggggctgg acttcgcctg tgatatctac atctgggcgc ccttggccgg acttgtgggg        960
gtccttctcc tgtcactggt tatcaccctt tactgcaaac ggggcagaaa gaaactcctg       1020
tatatattca aacaaccatt tatgagacca gtacaaacta ctcaagagga agatggctgt       1080
agctgccgat ttccagaaga agaagaagga ggatgtgaac tgagagtgaa gttcagcagg       1140
agcgcagacg cccccgcgta ccagcagggc cagaaccagc tctataacga gctcaatcta       1200
ggacgaagag aggagtacga tgttttggac aagagacgtg gccgggaccc tgagatgggg       1260
ggaaagccgc agagaaggaa gaaccctcag aaggcctgt acaatgaact gcagaaagat       1320
aagatggcgg aggcctacag tgagattggg atgaaaggcg agcgccggag gggcaagggg       1380
cacgatggcc tttaccaggg tctcagtaca gccaccaagg acacctacga cgcccttcac       1440
atgcaggccc tgccccctcg ctaa                                              1464
```

```
<210> SEQ ID NO 15
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
```

```
atgagcgttc caacccaagt tctgggactg cttctgctct ggttgactga cgctaggtgc         60
gaaatagtaa tgacccaatc cccagccact ctctccgtta gcccaggtga aagagccact        120
cttagttgca gggctagtca atccgtatct agcaacctgg cctggtacca gcaaaagccc        180
ggacaagcgc cgcggttgtt gatctatggg acgagcacac gagctacggg tattccggcc        240
aggttctcag ggtctggctc cggaaccgaa tttacattga cgatcagtag tctgcaatca        300
gaggatttcg ccgtttacta ttgccaacag tacaataatt ggccgctcac attcgggga        360 ggaaccaagg tcgagattaa gggaggtggg gtagtgggg cggggggtc aggaggtgga        420 ggagaggtac agttggtaga aagcggcggg gggttggttc aacctggacg gagtctgaga        480
ttgtcttgcg tggcttccgg ctttactttc aatgattacg ccatgcactg ggtacgccag        540
gcgcctggaa agggtctgga gtgggtttcc gtgatatcct ggaatagtga tagtataggc        600
tatgccgata gtgtaaaagg aaggtttaca atctctaggg ataacgctaa gaacagcctg        660
```

-continued

```
taccttcaaa tgcatagtct ccgggctgag gacacagcct tgtactattg tgctaaggac        720
aatcattatg gaagcgggtc atattattac tatcaatatg ggatggatgt gtggggtcag        780
ggaacgaccg ttacggtatc ctcaaccacc acccctgcac caaggccccc gactcccgcg        840
cccaccatcg cgtcacagcc tcttagcctg cgaccggaag catgcagacc agctgccggg        900
ggggccgtgc atacgagagg tttggacttc gcctgcgata tctacatctg ggcgcccttg        960
gccgggactt gtggggtcct tctcctgtca ctggttatca ccctttactg caaacggggc       1020
agaaagaaac tcctgtatat attcaaacaa ccatttatga gaccagtaca aactactcaa       1080
gaggaagatg gctgtagctg ccgatttcca gaagaagaag aaggaggatg tgaactgaga       1140
gtgaagttca gcaggagcgc agacgccccc gcgtaccagc agggccagaa ccagctctat       1200
aacgagctca atctaggacg aagagaggag tacgatgttt tggacaagag acgtggccgg       1260
gaccctgaga tggggggaaa gccgcagaga aggaagaacc ctcaggaagg cctgtacaat       1320
gaactgcaga aagataagat ggcggaggcc tacagtgaga ttgggatgaa aggcgagcgc       1380 cggagggca aggggcacga tggcctttac cagggtctca gtacagccac caaggacacc       1440
tacgacgccc ttcacatgca ggccctgccc cctcgctaa                             1479
```

<210> SEQ ID NO 16
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

```
atgtccgtac ctacccaggt gctgggcctg ctgctgctgt ggctgaccga cgccagatgc         60
gaaattgtgt tgacacagtc tccagccacc ctgtctttgt ctccagggga aagagccgcc        120
ctctcctgca gggccagtca gagtgttagc aactacttag cctggtacca acagaaacct        180
ggccaggctc ccaggctcct catctatgat gcatccaaca gggccactgg catcccagcc        240
aggttcagtg gcagtgggtc tgggacagac ttcactctca ccatcagcag cctagagcct        300
gaagattttg cagtttatta ctgtcagcag cgtagcaact ggccgctcac tttcggcgga        360
gggaccaagg tggagatcag aggtggaggt ggatctggag gaggaggatc cggtggagga        420
ggtgaagtgc agctggtgga gtctggggga ggcttggtac agcctggcag gtccctgcga        480
ctctcctgtg cagcctctgg attcaccttt cgagattata ccatgcactg ggtccggcaa        540
ggtccaggga agggcctgga atgggtctca ggtattagtt ggaatagtga ttacataggc        600
tatgcggact ctgtgaaggg ccgattcacc atctccagac acaacgccaa gaactccctg        660
tatctgcaaa tgaacagtct gagagttgag gacacggcct tgtattactg tgcaaagctc        720
agtgggacct acagggacta cttctacgga gtggacgtct ggggccaagg gaccacggtc        780
accgtctcct caaccaccac ccctgcacca aggcccccga ctcccgcgcc caccatcgcg        840
tcacagcctc ttagcctgcg accggaagca tgcagaccag ctgccggggg ggccgtgcat        900
acgagaggtt tggacttcgc ctgcgatatc tacatctggg cgcccttggc cgggacttgt        960
ggggtccttc tcctgtcact ggttatcacc ctttactgca acgggcag aaagaaactc       1020 ctgtatatat tcaaacaacc atttatgaga ccagtacaaa ctactcaaga ggaagatggc       1080
tgtagctgcc gatttccaga agaagaagaa ggaggatgtg aactgagagt gaagttcagc       1140
```

-continued

```
aggagcgcag acgcccccgc gtaccagcag ggccagaacc agctctataa cgagctcaat    1200
ctaggacgaa gagaggagta cgatgttttg gacaagagac gtggccggga ccctgagatg    1260
gggggaaagc cgcagagaag gaagaaccct caggaaggcc tgtacaatga actgcagaaa    1320
gataagatgg cggaggccta cagtgagatt gggatgaaag cgagcgccg gaggggcaag    1380 gggcacgatg gcctttacca gggtctcagt acagccacca aggacaccta cgacgccctt    1440
cacatgcagg ccctgccccc tcgctaa                                        1467

<210> SEQ ID NO 17
<211> LENGTH: 1461
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
atgtccgtgc ctacccaggt gctgggcctg ctgctgctgt ggctgaccga cgccagatgc      60
gaaattgtgg tgacacagtc tccagccacc ctgtctttgt ctccagggga aagagccacc     120
ctctcctgca ggaccagtca gactactacc agctacttag cctggtaccg acagaaacct     180
ggccaggctc ccaggctcct catctatgat gcatccaaca gggccgctgg catcccagcc     240
aggttcagtg gcagtgggtc tgggacagac ttcactctca ccatcaacag cctggagcct     300
gaagattttg cagtttatta ctgtcagctg cgtaccaact ggatcacctt cggccaaggg     360
acacgactgg agattaaagg tggaggtgga tctggaggag gaggatccgg tggaggaggt     420
caggtgcagc tggtggagtc tgggggagac tcggtcaagc ctggagggtc cctgagactc     480
tcctgtgcag cctctggatt caccttcagt gactcctaca tgacttggat ccgccaggct     540
ccagggaagg ggctggagtg ggtttcattc attagtagta gtggaagtac catatattat     600
gcagactctg tgaagggccg attcaccatt tccagggaca cgtcaagaa gtcattgtat     660 ctgcagatga acagactgag agccgaggac acggccgtgt attactgtgc gagagaagaa     720
ccaggaaact acgtctatta cggtatggac gtctgggggcc aagggaccac ggtcaccgtc     780
tcctcaacca ccacccctgc accaaggccc ccgactcccg cgccaccat cgcgtcacag     840 cctcttagcc tgcgaccgga agcatgcaga ccagctgccg ggggggccgt gcatacgaga     900
ggtttggact cgcctgcga tatctacatc tgggcgccct tggccgggac ttgtgggggtc     960 cttctcctgt cactggttat cacccttac tgcaaacggg gcagaaagaa actcctgtat    1020
atattcaaac aaccatttat gagaccagta caaactactc aagaggaaga tggctgtagc    1080
tgccgatttc cagaagaaga agaaggagga tgtgaactga gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tggggggga    1260 aagccgcaga gaaggaagaa ccctcaggaa ggcctgtaca tgaactgca gaaagataag    1320 atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc ccctcgcta a                                              1461

<210> SEQ ID NO 18
<211> LENGTH: 135
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic polynucleotide"

<400> SEQUENCE: 18
accaccaccc ctgcaccaag gcccccgact cccgcgccca ccatcgcgtc acagcctctt      60
agcctgcgac cggaagcatg cagaccagct gccggggggg ccgtgcatac gagaggtttg     120
gacttcgcct gcgat                                                     135

<210> SEQ ID NO 19
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
accacgacgc cagcgccgcg accaccaaca ccggcgccca ccatcgcgtc gcagcccctg      60
tccctgcgcc cagaggcgtg ccggccagcg gcggggggcg cagtgcacac gaggggggctg    120 gacttcgcct gtgat                                                     135

<210> SEQ ID NO 20
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Ser Val Pro Thr Gln Val Leu Gly Leu Leu Leu Leu Trp Leu Thr
1               5                   10                  15

Asp Ala Arg Cys Glu Ile Val Met Thr Gln Ser Pro Ala Thr Leu Ser
                20                  25                  30

Val Ser Pro Gly Glu Arg Thr Thr Leu Ser Cys Arg Ala Ser Gln Ser
            35                  40                  45

Val Ser Ser Asn Leu Ala Trp Tyr Leu Gln Lys Pro Gly Gln Ala Pro
        50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Ile Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Ile Thr Phe Gly Gln Gly Thr Arg Leu Glu Ile Lys Gly
        115                 120                 125

Gly Gly Gly Ser Gly Gly Gly Gly Ser Gly Gly Gly Gly Glu Val Gln
        130                 135                 140

Leu Val Glu Ser Gly Gly Gly Leu Val Gln Pro Gly Arg Ser Leu Arg
145                 150                 155                 160

Leu Ser Cys Ala Ala Ser Gly Phe Thr Phe Tyr Asp Tyr Ala Met His
                165                 170                 175

Trp Val Arg Gln Ala Pro Gly Lys Gly Leu Glu Trp Val Ser Gly Ile
            180                 185                 190
```

-continued

```
Ser Trp Asn Ser Gly Tyr Ile Gly Tyr Ala Asp Ser Val Lys Gly Arg
        195                 200                 205

Phe Thr Ile Ser Arg Asp Asn Ala Lys Asn Ser Leu Tyr Leu Gln Met
        210                 215                 220

Asn Ser Leu Arg Ala Glu Asp Thr Ala Leu Tyr Tyr Cys Ala Lys Asp
225                 230                 235                 240

Asn Ser Tyr Gly Lys Phe Tyr Tyr Gly Leu Asp Val Trp Gly Gln Gly
                245                 250                 255

Thr Thr Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Val Lys Phe
                325                 330                 335

Ser Arg Ser Ala Asp Ala Pro Ala Tyr Gln Gln Gly Gln Asn Gln Leu
                340                 345                 350

Tyr Asn Glu Leu Asn Leu Gly Arg Arg Glu Glu Tyr Asp Val Leu Asp
                355                 360                 365

Lys Arg Arg Gly Arg Asp Pro Glu Met Gly Gly Lys Pro Gln Arg Arg
        370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
                405                 410                 415

Lys Gly His Asp Gly Leu Tyr Gln Gly Leu Ser Thr Ala Thr Lys Asp
                420                 425                 430

Thr Tyr Asp Ala Leu His Met Gln Ala Leu Pro Pro Arg
        435                 440                 445
```

```
<210> SEQ ID NO 21
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Arg Ala Gly Asp Asn Trp Asn Trp Phe Asp Pro
1               5                   10
```

```
<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gln Gln Ala Lys Ser Val Pro Phe Thr
1               5
```

```
<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Glu Gly Gly Asn Tyr Gly Met Asp Val
1               5

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Gln Ala Asn Ser Phe Pro Pro Thr
1               5

<210> SEQ ID NO 25
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Phe Ala Glu Tyr Cys Gly Gly Asn Ile Cys Tyr Tyr Tyr Gly Met Asp
1               5                   10                  15

Val

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Gln Cys Gly Gly Ser Pro Trp Thr
1               5

<210> SEQ ID NO 27
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Ser Val Pro Thr Gln Val Leu Gly Leu Leu Leu Leu Trp Leu Thr
1               5                   10                  15

Asp Ala Arg Cys Glu Val Gln Leu Val Glu Ser Gly Gly Gly Leu Val
                20                  25                  30
```

Gln Pro Gly Gly Ser Leu Arg Leu Ser Cys Ala Ala Ser Gly Phe Thr
        35              40                  45

Phe Ser Ser Tyr Val Met Ser Trp Val Arg Gln Ala Pro Gly Lys Gly
    50                  55                  60

Leu Glu Trp Val Ser Ala Ile Ile Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Arg Ala Gly Asp Asn Trp Asn Trp Phe Asp
        115                 120                 125

Pro Trp Gly Gln Gly Thr Leu Val Thr Val
    130                 135

<210> SEQ ID NO 28
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Gln Met Thr Gln Ser Pro Ser Ser Val Ser Ala Ser Leu Gly
1               5                   10                  15

Asp Arg Val Thr Ile Thr Cys Arg Ala Ser Gln Gly Ile Ser Ser Trp
            20                  25                  30

Leu Ala Trp Tyr Gln Arg Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ala Lys Ser Val Pro Phe
                85                  90                  95

Thr Phe Gly Pro Gly Thr Lys Val Asp Ile Lys
            100                 105

<210> SEQ ID NO 29
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Ser Val Pro Thr Gln Val Leu Gly Leu Leu Leu Leu Trp Leu Thr
1               5                   10                  15

Asp Ala Arg Cys Gln Val Gln Leu Val Glu Ser Gly Gly Gly Leu Val
            20                  25                  30

Lys Pro Gly Gly Ser Leu Arg Leu Ser Cys Ala Ala Ser Gly Phe Thr
        35                  40                  45

Phe Ser Asp Tyr Tyr Ile Ser Trp Ile Arg Gln Ala Pro Gly Lys Gly
    50                  55                  60

Leu Glu Trp Val Ser Tyr Ile Ser Ser Ser Gly Ser Ser Ile Lys Tyr

```
65                    70                    75                    80

Ala Asp Ser Val Lys Gly Arg Phe Thr Ile Ser Arg Asp Asn Ala Lys
                    85                    90                    95

Asn Ser Leu Tyr Leu Gln Met Asn Ser Leu Arg Ala Glu Asp Thr Ala
                    100                   105                   110

Val Tyr Tyr Cys Ala Arg Glu Gly Gly Asn Tyr Gly Met Asp Val Trp
            115                   120                   125

Gly Gln Gly Thr Thr Val Thr Val
    130                   135
```

<210> SEQ ID NO 30
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

```
Asp Ile Gln Met Thr Gln Ser Pro Ser Ser Val Ser Ala Ser Val Gly
1                    5                    10                    15

Asp Arg Val Thr Ile Thr Cys Arg Ala Ser Gln Gly Ile Asn Asn Trp
                    20                    25                    30

Leu Val Trp Tyr Gln Gln Lys Pro Gly Lys Ala Pro Lys Leu Leu Ile
            35                    40                    45

Tyr Ala Ala Thr Ser Leu Gln Ser Gly Val Pro Ser Arg Phe Ser Gly
    50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln Ala Asn Ser Phe Pro Pro
                    85                    90                    95

Thr Phe Gly Gln Gly Thr Lys Leu Glu Ile Lys
            100                   105
```

<210> SEQ ID NO 31
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

```
Met Ser Val Pro Thr Gln Val Leu Gly Leu Leu Leu Leu Trp Leu Thr
1                    5                    10                    15

Asp Ala Arg Cys Gln Val Gln Leu Gln Glu Ser Gly Pro Gly Leu Val
                    20                    25                    30

Lys Pro Ser Glu Thr Leu Ser Leu Thr Cys Thr Val Ser Gly Gly Ser
            35                    40                    45

Ile Asn Tyr Tyr Tyr Trp Asn Trp Ile Arg Gln Pro Pro Gly Lys Gly
    50                    55                    60

Leu Glu Trp Ile Gly Tyr Ile Ser Tyr Ser Gly Asn Thr Asn Tyr Asn
65                    70                    75                    80

Pro Ser Leu Lys Ser Arg Val Thr Ile Ser Val Ala Thr Ser Arg Asn
                    85                    90                    95

Gln Phe Ser Leu Thr Leu Ser Ser Val Thr Ala Ala Asp Thr Ala Val
            100                   105                   110
```

-continued

```
Tyr Tyr Cys Ala Arg Phe Ala Glu Tyr Cys Gly Gly Asn Ile Cys Tyr
        115                 120                 125

Tyr Tyr Gly Met Asp Val Trp Gly Gln Gly Thr Thr Val Thr Val
        130                 135                 140

<210> SEQ ID NO 32
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Ile Val Leu Thr Gln Ser Pro Gly Thr Leu Ser Leu Ser Pro Gly
1               5                   10                  15

Glu Arg Ala Thr Phe Ser Cys Arg Ala Ser Gln Ser Val Gly Ser Ser
                20                  25                  30

Phe Leu Ala Trp Tyr Gln Gln Lys Pro Gly Gln Ala Pro Arg Arg Leu
            35                  40                  45

Met Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Cys Gly Gly Ser Pro
                85                  90                  95

Trp Thr Phe Gly Gln Gly Thr Lys Val Glu Ile Lys
            100                 105

<210> SEQ ID NO 33
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Met Ala Leu Pro Val Thr Ala Leu Leu Leu Pro Leu Ala Leu Leu Leu
1               5                   10                  15

His Ala Ala Arg Pro
            20

<210> SEQ ID NO 34
<211> LENGTH: 114
<212> TYPE: PRT
<213> ORGANISM: Homo sapiens

<400> SEQUENCE: 34

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
```

```
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 35
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Ser Val Pro Thr Gln Val Leu Gly Leu Leu Leu Leu Trp Leu Thr
1               5                   10                  15

Asp Ala Arg Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Val Met Ser Trp Val Arg Gln Ala Pro Gly Lys Gly
    50                  55                  60

Leu Glu Trp Val Ser Ala Ile Ile Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Arg Ala Gly Asp Asn Trp Asn Trp Phe Asp
            115                 120                 125

Pro Trp Gly Gln Gly Thr Leu Val Thr Val Ser Ser Gly Gly Gly Gly
        130                 135                 140

Ser Gly Gly Gly Gly Ser Gly Gly Gly Gly Asp Ile Gln Met Thr Gln
145                 150                 155                 160

Ser Pro Ser Ser Val Ser Ala Ser Leu Gly Asp Arg Val Thr Ile Thr
                165                 170                 175

Cys Arg Ala Ser Gln Gly Ile Ser Ser Trp Leu Ala Trp Tyr Gln Arg
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Ala Asp
    210                 215                 220

Phe Thr Leu Thr Ile Ser Ser Leu Gln Pro Glu Asp Phe Ala Thr Tyr
225                 230                 235                 240

Tyr Cys Gln Gln Ala Lys Ser Val Pro Phe Thr Phe Gly Pro Gly Thr
                245                 250                 255

Lys Val Asp Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300
```

-continued

```
Cys Asp Ile Tyr Ile Trp Ala Pro Leu Ala Gly Thr Cys Gly Val Leu
305             310             315             320

Leu Leu Ser Leu Val Ile Thr Leu Tyr Cys Lys Arg Gly Arg Lys Lys
                325             330             335

Leu Leu Tyr Ile Phe Lys Gln Pro Phe Met Arg Pro Val Gln Thr Thr
            340             345             350

Gln Glu Glu Asp Gly Cys Ser Cys Arg Phe Pro Glu Glu Glu Glu Gly
        355             360             365

Gly Cys Glu Leu Arg Val Lys Phe Ser Arg Ser Ala Asp Ala Pro Ala
    370             375             380

Tyr Gln Gln Gly Gln Asn Gln Leu Tyr Asn Glu Leu Asn Leu Gly Arg
385             390             395             400

Arg Glu Glu Tyr Asp Val Leu Asp Lys Arg Arg Gly Arg Asp Pro Glu
            405             410             415

Met Gly Gly Lys Pro Gln Arg Arg Lys Asn Pro Gln Glu Gly Leu Tyr
            420             425             430

Asn Glu Leu Gln Lys Asp Lys Met Ala Glu Ala Tyr Ser Glu Ile Gly
        435             440             445

Met Lys Gly Glu Arg Arg Arg Gly Lys Gly His Asp Gly Leu Tyr Gln
    450             455             460

Gly Leu Ser Thr Ala Thr Lys Asp Thr Tyr Asp Ala Leu His Met Gln
465             470             475             480

Ala Leu Pro Pro Arg
            485

<210> SEQ ID NO 36
<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Ser Val Pro Thr Gln Val Leu Gly Leu Leu Leu Leu Trp Leu Thr
1               5               10              15

Asp Ala Arg Cys Gln Val Gln Leu Val Glu Ser Gly Gly Gly Leu Val
            20              25              30

Lys Pro Gly Gly Ser Leu Arg Leu Ser Cys Ala Ala Ser Gly Phe Thr
        35              40              45

Phe Ser Asp Tyr Tyr Ile Ser Trp Ile Arg Gln Ala Pro Gly Lys Gly
    50              55              60

Leu Glu Trp Val Ser Tyr Ile Ser Ser Ser Gly Ser Ser Ile Lys Tyr
65              70              75              80

Ala Asp Ser Val Lys Gly Arg Phe Thr Ile Ser Arg Asp Asn Ala Lys
            85              90              95

Asn Ser Leu Tyr Leu Gln Met Asn Ser Leu Arg Ala Glu Asp Thr Ala
            100             105             110

Val Tyr Tyr Cys Ala Arg Glu Gly Gly Asn Tyr Gly Met Asp Val Trp
            115             120             125

Gly Gln Gly Thr Thr Val Thr Val Ser Ser Gly Gly Gly Gly Ser Gly
        130             135             140

Gly Gly Gly Ser Gly Gly Gly Gly Asp Ile Gln Met Thr Gln Ser Pro
145             150             155             160

Ser Ser Val Ser Ala Ser Val Gly Asp Arg Val Thr Ile Thr Cys Arg
```

-continued

```
                165               170               175
Ala Ser Gln Gly Ile Asn Asn Trp Leu Val Trp Tyr Gln Gln Lys Pro
            180               185               190

Gly Lys Ala Pro Lys Leu Leu Ile Tyr Ala Ala Thr Ser Leu Gln Ser
        195               200               205

Gly Val Pro Ser Arg Phe Ser Gly Ser Gly Ser Gly Thr Asp Phe Thr
    210               215               220

Leu Thr Ile Ser Ser Leu Gln Pro Glu Asp Phe Ala Thr Tyr Tyr Cys
225               230               235               240

Gln Gln Ala Asn Ser Phe Pro Pro Thr Phe Gly Gln Gly Thr Lys Leu
            245               250               255

Glu Ile Lys Thr Thr Thr Pro Ala Pro Arg Pro Pro Thr Pro Ala Pro
            260               265               270

Thr Ile Ala Ser Gln Pro Leu Ser Leu Arg Pro Glu Ala Cys Arg Pro
            275               280               285

Ala Ala Gly Gly Ala Val His Thr Arg Gly Leu Asp Phe Ala Cys Asp
        290               295               300

Ile Tyr Ile Trp Ala Pro Leu Ala Gly Thr Cys Gly Val Leu Leu Leu
305               310               315               320

Ser Leu Val Ile Thr Leu Tyr Cys Lys Arg Gly Arg Lys Lys Leu Leu
            325               330               335

Tyr Ile Phe Lys Gln Pro Phe Met Arg Pro Val Gln Thr Thr Gln Glu
            340               345               350

Glu Asp Gly Cys Ser Cys Arg Phe Pro Glu Glu Glu Gly Gly Cys
        355               360               365

Glu Leu Arg Val Lys Phe Ser Arg Ser Ala Asp Ala Pro Ala Tyr Gln
    370               375               380

Gln Gly Gln Asn Gln Leu Tyr Asn Glu Leu Asn Leu Gly Arg Arg Glu
385               390               395               400

Glu Tyr Asp Val Leu Asp Lys Arg Arg Gly Arg Asp Pro Glu Met Gly
            405               410               415

Gly Lys Pro Gln Arg Arg Lys Asn Pro Gln Glu Gly Leu Tyr Asn Glu
            420               425               430

Leu Gln Lys Asp Lys Met Ala Glu Ala Tyr Ser Glu Ile Gly Met Lys
        435               440               445

Gly Glu Arg Arg Arg Gly Lys Gly His Asp Gly Leu Tyr Gln Gly Leu
    450               455               460

Ser Thr Ala Thr Lys Asp Thr Tyr Asp Ala Leu His Met Gln Ala Leu
465               470               475               480

Pro Pro Arg
```

```
<210> SEQ ID NO 37
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Ser Val Pro Thr Gln Val Leu Gly Leu Leu Leu Leu Trp Leu Thr
1               5               10                15

Asp Ala Arg Cys Gln Val Gln Leu Gln Glu Ser Gly Pro Gly Leu Val
            20               25               30
```

-continued

```
Lys Pro Ser Glu Thr Leu Ser Leu Thr Cys Thr Val Ser Gly Gly Ser
        35                  40                  45

Ile Asn Tyr Tyr Tyr Trp Asn Trp Ile Arg Gln Pro Pro Gly Lys Gly
        50                  55                  60

Leu Glu Trp Ile Gly Tyr Ile Ser Tyr Ser Gly Asn Thr Asn Tyr Asn
65                  70                  75                  80

Pro Ser Leu Lys Ser Arg Val Thr Ile Ser Val Ala Thr Ser Arg Asn
                85                  90                  95

Gln Phe Ser Leu Thr Leu Ser Ser Val Thr Ala Ala Asp Thr Ala Val
            100                 105                 110

Tyr Tyr Cys Ala Arg Phe Ala Glu Tyr Cys Gly Gly Asn Ile Cys Tyr
            115                 120                 125

Tyr Tyr Gly Met Asp Val Trp Gly Gln Gly Thr Thr Val Thr Val Ser
        130                 135                 140

Ser Gly Gly Gly Gly Ser Gly Gly Gly Gly Ser Gly Gly Gly Gly Glu
145                 150                 155                 160

Ile Val Leu Thr Gln Ser Pro Gly Thr Leu Ser Leu Ser Pro Gly Glu
                165                 170                 175

Arg Ala Thr Phe Ser Cys Arg Ala Ser Gln Ser Val Gly Ser Ser Phe
            180                 185                 190

Leu Ala Trp Tyr Gln Gln Lys Pro Gly Gln Ala Pro Arg Arg Leu Met
            195                 200                 205

Tyr Gly Ala Ser Asn Arg Ala Thr Gly Ile Pro Asp Arg Phe Ser Gly
        210                 215                 220

Ser Gly Ser Gly Thr Asp Phe Thr Leu Thr Ile Ser Arg Leu Glu Pro
225                 230                 235                 240

Glu Asp Phe Ala Val Tyr Tyr Cys Gln Gln Cys Gly Gly Ser Pro Trp
                245                 250                 255

Thr Phe Gly Gln Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
        290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
        370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Gln Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
```

-continued

```
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 38
<211> LENGTH: 645
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Ser Val Pro Thr Gln Val Leu Gly Leu Leu Leu Leu Trp Leu Thr
1               5                   10                  15

Asp Ala Arg Cys Gln Val Gln Leu Val Glu Ser Gly Gly Gly Leu Val
                20                  25                  30

Lys Pro Gly Gly Ser Leu Arg Leu Ser Cys Ala Ala Ser Gly Phe Thr
            35                  40                  45

Phe Ser Asp Tyr Tyr Ile Ser Trp Ile Arg Gln Ala Pro Gly Lys Gly
        50                  55                  60

Leu Glu Trp Val Ser Tyr Ile Ser Ser Ser Gly Ser Ser Ile Lys Tyr
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Arg Glu Gly Gly Asn Tyr Gly Met Asp Val Trp
            115                 120                 125

Gly Gln Gly Thr Thr Val Thr Val Ser Ser Gly Gly Gly Gly Ser Gly
        130                 135                 140

Gly Gly Gly Ser Gly Gly Gly Gly Asp Ile Gln Met Thr Gln Ser Pro
145                 150                 155                 160

Ser Ser Val Ser Ala Ser Val Gly Asp Arg Val Thr Ile Thr Cys Arg
                165                 170                 175

Ala Ser Gln Gly Ile Asn Asn Trp Leu Val Trp Tyr Gln Gln Lys Pro
            180                 185                 190

Gly Lys Ala Pro Lys Leu Leu Ile Tyr Ala Ala Thr Ser Leu Gln Ser
            195                 200                 205

Gly Val Pro Ser Arg Phe Ser Gly Ser Gly Ser Gly Thr Asp Phe Thr
        210                 215                 220

Leu Thr Ile Ser Ser Leu Gln Pro Glu Asp Phe Ala Thr Tyr Tyr Cys
225                 230                 235                 240

Gln Gln Ala Asn Ser Phe Pro Pro Thr Phe Gly Gln Gly Thr Lys Leu
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
        290                 295                 300

Ile Tyr Ile Trp Ala Pro Leu Ala Gly Thr Cys Gly Val Leu Leu Leu
305                 310                 315                 320
```

-continued

```
Ser Leu Val Ile Thr Leu Tyr Cys Lys Arg Gly Arg Lys Lys Leu Leu
            325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Gln
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Gln Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg Arg Ala Lys Arg Ser Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Leu Pro Val Thr Ala Leu Leu Leu Pro Leu Ala Leu Leu Leu His Ala
            515                 520                 525

Ala Arg Pro Asn Trp Val Asn Val Ile Ser Asp Leu Lys Lys Ile Glu
        530                 535                 540

Asp Leu Ile Gln Ser Met His Ile Asp Ala Thr Leu Tyr Thr Glu Ser
545                 550                 555                 560

Asp Val His Pro Ser Cys Lys Val Thr Ala Met Lys Cys Phe Leu Leu
                565                 570                 575

Glu Leu Gln Val Ile Ser Leu Glu Ser Gly Asp Ala Ser Ile His Asp
            580                 585                 590

Thr Val Glu Asn Leu Ile Ile Leu Ala Asn Asn Ser Leu Ser Ser Asn
            595                 600                 605

Gly Asn Val Thr Glu Ser Gly Cys Lys Glu Cys Glu Glu Leu Glu Glu
        610                 615                 620

Lys Asn Ile Lys Glu Phe Leu Gln Ser Phe Val His Ile Val Gln Met
625                 630                 635                 640

Phe Ile Asn Thr Ser
                645
```

```
<210> SEQ ID NO 39
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
atgagcgtgc ctacccaggt gctgggactg ctgctgctgt ggctgacaga cgcaaggtgc      60
gaggtgcagc tggtggagtc cggaggagga ctggtgcagc caggaggatc cctgaggctg     120
```

```
tcttgcgccg ccagcggctt cacctttagc tcctacgtga tgtcctgggt gcgccaggca      180
cctggcaagg gactggagtg ggtgtctgcc atcatcggct ctggcggcag cacatactat      240
gccgacagcg tgaagggccg gttcaccatc tccagagata actctaagaa tacactgtat      300
ctgcagatga acagcctgag ggcagaggac accgccgtgt actattgcgc caagagagcc      360
ggcgacaact ggaattggtt tgatccatgg ggccagggca ccctggtgac agtgtctagc      420
ggaggaggag gatctggagg aggaggaagc ggcggaggag gcgacatcca gatgacacag      480
tccccatcct ctgtgagcgc ctccctgggc gatagggtga ccatcacatg tcgcgcctct      540
cagggcatca gctcctggct ggcatggtac cagaggaagc caggcaaggc ccctaagctg      600
ctgatctatg cagcatctag cctgcagagc ggagtgcctt cccggttctc tggaagcgga      660
tccggagcag actttaccct gacaatctcc tctctgcagc cagaggattt cgccacctac      720
tattgtcagc aggccaagtc cgtgccattc acctttggcc ccggcacaaa ggtggatatc      780
aagaccacca cccctgcacc aaggcccccg actcccgcgc ccaccatcgc gtcacagcct      840
cttagcctgc gaccggaagc atgcagacca gctgccgggg gggccgtgca tacgagaggt      900
ttggacttcg cctgcgatat ctacatctgg gcgcccttgg ccgggacttg tggggtcctt      960
ctcctgtcac tggttatcac cctttactgc aaacggggca gaaagaaact cctgtatata     1020
ttcaaacaac catttatgag accagtacaa actactcaag aggaagatgg ctgtagctgc     1080
cgatttccag aagaagaaga aggaggatgt gaactgagag tgaagttcag caggagcgca     1140
gacgcccccg cgtaccagca gggccagaac cagctctata cgagctcaa tctaggacga      1200 agagaggagt acgatgtttt ggacaagaga cgtggccggg accctgagat ggggggaaag     1260
ccgcagagaa ggaagaaccc tcaggaaggc ctgtacaatg aactgcagaa agataagatg     1320
gcggaggcct acagtgagat tgggatgaaa ggcgagcgcc ggaggggcaa ggggcacgat     1380
ggcctttacc agggtctcag tacagccacc aaggacacct acgacgccct tcacatgcag     1440
gccctgcccc ctcgctaa                                                     1458
```

```
<210> SEQ ID NO 40
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
```

```
atgagcgtgc ctacccaggt gctgggactg ctgctgctgt ggctgacaga cgcaaggtgc       60
caggtgcagc tggtggagag cggaggagga ctggtgaagc caggaggaag cctgaggctg      120
tcctgcgccg cctctggctt cacctttagc gactactata tctcctggat caggcaggca      180
cctggcaagg gactggagtg ggtgtcctac atcagctcct ctggcagctc catcaagtat      240
gccgactctg tgaagggccg gttcaccatc tccagagata cgccaagaa ttctctgtac       300 ctgcagatga acagcctgcg ggccgaggac acagccgtgt actattgcgc cagagagggc      360
ggcaattatg catggacgt gtggggccag ggcaccacg tgaccgtgtc tagcggcggc       420
ggcggctctg gaggaggagg aagcggcgga ggaggcgaca tccagatgac acagagccca      480
tccagcgtga cgccagcgt gggcgatagg gtgaccatca catgtcgcgc ctcccagggc      540
atcaacaatt ggctggtgtg gtaccagcag aagccaggca aggccccaa gctgctgatc       600
```

-continued

```
tatgcagcca cctccctgca gtctggagtg cctagccggt tctccggatc tggaagcgga    660
accgacttta ccctgacaat cagctccctg cagccagagg attttgccac atactattgt    720
cagcaggcca actccttccc ccctaccttt ggccagggca caaagctgga gatcaagacc    780
accacccctg caccaaggcc cccgactccc gcgcccacca tcgcgtcaca gcctcttagc    840
ctgcgaccgg aagcatgcag accagctgcc ggtggggcgg tgcatacgag aggtttggac    900
ttcgcctgcg atatctacat ctgggcgccc ttggccggga cttgtggggt ccttctcctg    960
tcactggtta tcacccttta ctgcaaacgg ggcagaaaga aactcctgta tatattcaaa   1020
caaccattta tgagaccagt acaaactact caagaggaag atggctgtag ctgccgattt   1080
ccagaagaag aagaaggagg atgtgaactg agagtgaagt tcagcaggag cgcagacgcc   1140
cccgcgtacc agcagggcca gaaccagctc tataacgagc tcaatctagg acgaagagag   1200
gagtacgatg tttggacaa gagacgtggc cgggaccctg agatgggggg aaagccgcag   1260
agaaggaaga accctcagga aggcctgtac aatgaactgc agaaagataa gatggcggag   1320
gcctacagtg agattgggat gaaaggcgag cgccggaggg gcaaggggca cgatggcctt   1380
taccagggtc tcagtacagc caccaaggac acctacgacg cccttcacat gcaggccctg   1440 cccctcgct aa                                                        1452
```

```
<210> SEQ ID NO 41
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
```

```
atgagcgtgc ctacccaggt gctgggactg ctgctgctgt ggctgacaga cgcaaggtgc     60
caggtgcagc tgcaggagtc tggccctggc ctggtgaagc catccgagac cctgtctctg    120
acctgcacag tgagcggcgg ctccatcaat tactattact ggaactggat caggcagcca    180
cctggcaagg gactggagtg gatcggctac atcagctatt ccggcaacac caattacaac    240
ccttctctga gagcagggt gaccatcagc gtggccacat cccgcaatca gttcagcctg    300
acactgagct ccgtgaccgc agcagacaca gccgtgtatt actgcgcaag gtttgcagag    360
tactgcggag gcaacatctg ttattactat ggcatggacg tgtggggcca gggcaccaca    420
gtgaccgtgt ctagcggcgg cggcggctct ggaggaggag gaagcggagg aggaggagag    480
atcgtgctga cccagtcccc aggcacactg tctctgagcc ctggagagag ggccacattc    540
tcttgtcgcg cctcccagtc tgtgggctcc tcttttctgg cctggtacca gcagaagcca    600
ggacaggcac cacggagact gatgtatgga gcatccaata gggcaaccgg aatcccagac    660
agattcagcg gctccggctc tggcacagac ttcaccctga caatcagcag actggagcca    720
gaggacttcg ccgtgtacta ttgccagcag tgtggaggat ccccatggac ctttggccag    780
ggaacaaagg tggagatcaa gaccaccacc cctgcaccaa ggcccccgac tcccgcgccc    840
accatcgcgt cacagcctct tagcctgcga ccggaagcat gcagaccagc tgccgggggg    900
gccgtgcata cgagaggttt ggacttcgcc tgcgatatct acatctgggc gcccttggcc    960
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
```

-continued

```
aagttcagca ggagcgcaga cgcccccgcg taccagcagg gccagaacca gctctataac      1200
gagctcaatc taggacgaag agaggagtac gatgttttgg acaagagacg tggccgggac      1260
cctgagatgg ggggaaagcc gcagagaagg aagaaccctc aggaaggcct gtacaatgaa      1320
ctgcagaaag ataagatggc ggaggcctac agtgagattg ggatgaaagg cgagcgccgg      1380
aggggcaagg ggcacgatgg cctttaccag ggtctcagta cagccaccaa ggacacctac      1440
gacgcccttc acatgcaggc cctgcccccct cgctaa                              1476
```

<210> SEQ ID NO 42
<211> LENGTH: 1938
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42

```
atgagcgtgc ctacccaggt gctgggactg ctgctgctgt ggctgacaga cgcaaggtgc       60
caggtgcagc tggtggagag cggaggagga ctggtgaagc caggaggaag cctgaggctg      120
tcctgcgccg cctctggctt caccttfagc gactactata tctcctggat caggcaggca      180
cctggcaagg gactggagtg ggtgtcctac atcagctcct ctggcagctc catcaagtat      240
gccgactctg tgaagggccg gttcaccatc tccagagata cgccaagaa ttctctgtac       300 ctgcagatga acagcctgcg ggccgaggac acagccgtgt actattgcgc cagagagggc      360
ggcaattatg gcatggacgt gtggggccag ggcaccacag tgaccgtgtc tagcggcggc      420
ggcggctctg gaggaggagg aagcggcgga ggaggcgaca tccagatgac acagagccca      480
tccagcgtga gcgccagcgt gggcgatagg gtgaccatca catgtcgcgc ctcccagggc      540
atcaacaatt ggctggtgtg gtaccagcag aagccaggca aggcccccaa gctgctgatc      600
tatgcagcca cctccctgca gtctggagtg cctagccggt tctccggatc tggaagcgga      660
accgacttta ccctgacaat cagctccctg cagccagagg attttgccac atactattgt      720
cagcaggcca actccttccc ccctacctttt ggccagggca aaagctgga gatcaagacc       780 accacccctg caccaaggcc cccgactccc gcgcccacca tcgcgtcaca gcctcttagc      840
ctgcgaccgg aagcatgcag accagctgcc ggtggggcgg tgcatacgag aggtttggac      900
ttcgcctgcg atatctacat ctgggcgccc ttggccggga cttgtggggt ccttctcctg      960
tcactggtta tcacccttta ctgcaaacgg ggcagaaaga aactcctgta tatattcaaa     1020
caaccattta tgagaccagt acaaactact caagaggaag atggctgtag ctgccgattt     1080
ccagaagaag aagaaggagg atgtgaactg agagtgaagt tcagcaggag cgcagacgcc     1140
cccgcgtacc agcagggcca gaaccagctc tataacgagc tcaatctagg acgaagagag     1200
gagtacgatg ttttggacaa gagacgtggc cgggaccctg agatgggggg aaagccgcag     1260
agaaggaaga accctcagga aggcctgtac aatgaactgc agaaagataa gatggcggag     1320
gcctacagtg agattgggat gaaaggcgag cgccggaggg gcaaggggca cgatggcctt     1380
taccagggtc tcagtacagc caccaaggac acctacgacg cccttcacat gcaggccctg     1440 cccctcgcc gcgcgaagcg atcaggcagc ggggcgacaa atttcagcct tctgaaacaa     1500
gcaggcgacg tggaagaaaa ccccggtcca atggccttac cagtgaccgc cttgctcctg     1560
ccgctggcct tgctgctcca cgccgccagg ccgaactggg tgaatgtaat aagtgatttg     1620
```

-continued

```
aaaaaaattg aagatcttat tcaatctatg catattgatg ctactttata tacggaaagt   1680
gatgttcacc ccagttgcaa agtaacagca atgaagtgct ttctcttgga gttacaagtt   1740
atttcacttg agtccggaga tgcaagtatt catgatacag tagaaaatct gatcatccta   1800
gcaaacaaca gtttgtcttc taatgggaat gtaacagaat ctggatgcaa agaatgtgag   1860
gaactggagg aaaaaaatat taaagaattt ttgcagagtt ttgtacatat tgtccaaatg   1920
ttcatcaaca cttcttga                                                 1938
```

```
<210> SEQ ID NO 43
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Gly Ser Gly Ala Thr Asn Phe Ser Leu Leu Lys Gln Ala Gly Asp
1               5                   10                  15

Val Glu Glu Asn Pro Gly Pro
            20
```

```
<210> SEQ ID NO 44
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      furin cleavage sequence"

<400> SEQUENCE: 44

Arg Ala Lys Arg
1
```

```
<210> SEQ ID NO 45
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

```
<210> SEQ ID NO 46
<211> LENGTH: 644
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Met Ser Val Pro Thr Gln Val Leu Gly Leu Leu Leu Leu Trp Leu Thr
1               5                   10                  15

Asp Ala Arg Cys Glu Ile Val Met Thr Gln Ser Pro Ala Thr Leu Ser
```

-continued

```
                20              25              30

Val Ser Pro Gly Glu Arg Thr Thr Leu Ser Cys Arg Ala Ser Gln Ser
        35              40              45

Val Ser Ser Asn Leu Ala Trp Tyr Leu Gln Lys Pro Gly Gln Ala Pro
        50              55              60

Arg Leu Leu Ile Tyr Gly Ala Ser Thr Arg Ala Thr Gly Ile Pro Ala
65              70              75              80

Arg Phe Ser Gly Ser Gly Ser Gly Thr Glu Phe Ile Leu Thr Ile Ser
                85              90              95

Ser Leu Gln Ser Glu Asp Phe Ala Val Tyr Tyr Cys Gln Gln Tyr Asn
                100             105             110

Asn Trp Pro Ile Thr Phe Gly Gln Gly Thr Arg Leu Glu Ile Lys Gly
        115             120             125

Gly Gly Gly Ser Gly Gly Gly Gly Ser Gly Gly Gly Gly Glu Val Gln
        130             135             140

Leu Val Glu Ser Gly Gly Gly Leu Val Gln Pro Gly Arg Ser Leu Arg
145             150             155             160

Leu Ser Cys Ala Ala Ser Gly Phe Thr Phe Tyr Asp Tyr Ala Met His
                165             170             175

Trp Val Arg Gln Ala Pro Gly Lys Gly Leu Glu Trp Val Ser Gly Ile
                180             185             190

Ser Trp Asn Ser Gly Tyr Ile Gly Tyr Ala Asp Ser Val Lys Gly Arg
                195             200             205

Phe Thr Ile Ser Arg Asp Asn Ala Lys Asn Ser Leu Tyr Leu Gln Met
        210             215             220

Asn Ser Leu Arg Ala Glu Asp Thr Ala Leu Tyr Tyr Cys Ala Lys Asp
225             230             235             240

Asn Ser Tyr Gly Lys Phe Tyr Tyr Gly Leu Asp Val Trp Gly Gln Gly
                245             250             255

Thr Thr Val Thr Val Ser Ser Thr Thr Thr Pro Ala Pro Arg Pro Pro
                260             265             270

Thr Pro Ala Pro Thr Ile Ala Ser Gln Pro Leu Ser Leu Arg Pro Glu
                275             280             285

Ala Cys Arg Pro Ala Ala Gly Gly Ala Val His Thr Arg Gly Leu Asp
        290             295             300

Phe Ala Cys Asp Ile Tyr Ile Trp Ala Pro Leu Ala Gly Thr Cys Gly
305             310             315             320

Val Leu Leu Leu Ser Leu Val Ile Thr Leu Tyr Cys Lys Arg Gly Arg
                325             330             335

Lys Lys Leu Leu Tyr Ile Phe Lys Gln Pro Phe Met Arg Pro Val Gln
                340             345             350

Thr Thr Gln Glu Glu Asp Gly Cys Ser Cys Arg Phe Pro Glu Glu Glu
                355             360             365

Glu Gly Gly Cys Glu Leu Arg Val Lys Phe Ser Arg Ser Ala Asp Ala
        370             375             380

Pro Ala Tyr Gln Gln Gly Gln Asn Gln Leu Tyr Asn Glu Leu Asn Leu
385             390             395             400

Gly Arg Arg Glu Glu Tyr Asp Val Leu Asp Lys Arg Arg Gly Arg Asp
                405             410             415

Pro Glu Met Gly Gly Lys Pro Gln Arg Arg Lys Asn Pro Gln Glu Gly
                420             425             430

Leu Tyr Asn Glu Leu Gln Lys Asp Lys Met Ala Glu Ala Tyr Ser Glu
        435             440             445
```

```
Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg Gly Ser Gly Ala Thr Asn Phe Ser Leu
                485                 490                 495

Leu Lys Gln Ala Gly Asp Val Glu Glu Asn Pro Gly Pro Met Ala Leu
                500                 505                 510

Pro Val Thr Ala Leu Leu Leu Pro Leu Ala Leu Leu Leu His Ala Ala
                515                 520                 525

Arg Pro Asn Trp Val Asn Val Ile Ser Asp Leu Lys Lys Ile Glu Asp
    530                 535                 540

Leu Ile Gln Ser Met His Ile Asp Ala Thr Leu Tyr Thr Glu Ser Asp
545                 550                 555                 560

Val His Pro Ser Cys Lys Val Thr Ala Met Lys Cys Phe Leu Leu Glu
                565                 570                 575

Leu Gln Val Ile Ser Leu Glu Ser Gly Asp Ala Ser Ile His Asp Thr
                580                 585                 590

Val Glu Asn Leu Ile Ile Leu Ala Asn Asn Ser Leu Ser Ser Asn Gly
                595                 600                 605

Asn Val Thr Glu Ser Gly Cys Lys Glu Cys Glu Glu Leu Glu Glu Lys
    610                 615                 620

Asn Ile Lys Glu Phe Leu Gln Ser Phe Val His Ile Val Gln Met Phe
625                 630                 635                 640

Ile Asn Thr Ser
```

<210> SEQ ID NO 47
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 48
<211> LENGTH: 671
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Met Ser Val Pro Thr Gln Val Leu Gly Leu Leu Leu Leu Trp Leu Thr
1               5                   10                  15

Asp Ala Arg Cys Glu Ile Val Met Thr Gln Ser Pro Ala Thr Leu Ser
                20                  25                  30

Val Ser Pro Gly Glu Arg Thr Thr Leu Ser Cys Arg Ala Ser Gln Ser
        35                  40                  45

Val Ser Ser Asn Leu Ala Trp Tyr Leu Gln Lys Pro Gly Gln Ala Pro
```

```
                50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Ile Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Ile Thr Phe Gly Gln Gly Thr Arg Leu Glu Ile Lys Gly
            115                 120                 125

Gly Gly Gly Ser Gly Gly Gly Ser Gly Gly Gly Glu Val Gln
        130                 135                 140

Leu Val Glu Ser Gly Gly Gly Leu Val Gln Pro Gly Arg Ser Leu Arg
145                 150                 155                 160

Leu Ser Cys Ala Ala Ser Gly Phe Thr Phe Tyr Asp Tyr Ala Met His
            165                 170                 175

Trp Val Arg Gln Ala Pro Gly Lys Gly Leu Glu Trp Val Ser Gly Ile
            180                 185                 190

Ser Trp Asn Ser Gly Tyr Ile Gly Tyr Ala Asp Ser Val Lys Gly Arg
            195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Leu Tyr Tyr Cys Ala Lys Asp
225                 230                 235                 240

Asn Ser Tyr Gly Lys Phe Tyr Tyr Gly Leu Asp Val Trp Gly Gln Gly
            245                 250                 255

Thr Thr Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Gln Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480
```

```
Met Gln Ala Leu Pro Pro Arg Gly Ser Gly Ala Thr Asn Phe Ser Leu
                485                 490                 495

Leu Lys Gln Ala Gly Asp Val Glu Glu Asn Pro Gly Pro Met Arg Ile
            500                 505                 510

Ser Lys Pro His Leu Arg Ser Ile Ser Ile Gln Cys Tyr Leu Cys Leu
        515                 520                 525

Leu Leu Asn Ser His Phe Leu Thr Glu Ala Gly Ile His Val Phe Ile
    530                 535                 540

Leu Gly Cys Phe Ser Ala Gly Leu Pro Lys Thr Glu Ala Asn Trp Val
545                 550                 555                 560

Asn Val Ile Ser Asp Leu Lys Lys Ile Glu Asp Leu Ile Gln Ser Met
                565                 570                 575

His Ile Asp Ala Thr Leu Tyr Thr Glu Ser Asp Val His Pro Ser Cys
                580                 585                 590

Lys Val Thr Ala Met Lys Cys Phe Leu Leu Glu Leu Gln Val Ile Ser
            595                 600                 605

Leu Glu Ser Gly Asp Ala Ser Ile His Asp Thr Val Glu Asn Leu Ile
        610                 615                 620

Ile Leu Ala Asn Asn Ser Leu Ser Ser Asn Gly Asn Val Thr Glu Ser
625                 630                 635                 640

Gly Cys Lys Glu Cys Glu Glu Leu Glu Glu Lys Asn Ile Lys Glu Phe
                645                 650                 655

Leu Gln Ser Phe Val His Ile Val Gln Met Phe Ile Asn Thr Ser
                660                 665                 670
```

<210> SEQ ID NO 49
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45
```

<210> SEQ ID NO 50
<211> LENGTH: 1935
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

```
atgtccgtgc ctacccaggt gctgggcctg ctgctgctgt ggctgaccga cgccagatgc      60
gaaatagtga tgacgcagtc tccagccacc ctgtctgtgt ctccagggga aagaaccacc     120
ctctcctgca gggccagtca gagtgttagc agcaacttag cctggtacct tcagaaacct     180
ggccaggctc ccaggctcct catctatggt gcatccacca gggccactgg tatcccagcc     240
aggttcagtg gcagtgggtc tgggacagag ttcattctca ccatcagcag cctgcagtct     300
```

-continued

```
gaagattttg cagtttatta ctgtcagcag tataataact ggccgatcac cttcggccaa      360
gggacacggc tggagattaa aggtggaggt ggatctggag gaggaggatc cggtggagga      420
ggtgaagtgc aactggtgga gtctggggga ggcttggtac agcctggcag gtccctgaga      480
ctctcctgtg cagcctctgg attcaccttt tatgattatg ccatgcactg ggtccggcaa      540
gctccaggga agggcctgga gtgggtctca ggtattagtt ggaatagtgg ttacataggc      600
tatgcggact ctgtgaaggg ccgattcacc atctccagag acaacgccaa gaactccctg      660
tatctgcaaa tgaacagtct gagagctgag gacacggcct tgtattactg tgcaaaagat      720
aacagctatg gaaagttcta ctacggtttg gacgtctggg gccaagggac cacggtcacc      780
gtctcctcaa ccacgacgcc agcgccgcga ccaccaacac cggcgcccac catcgcgtcg      840
cagcccctgt ccctgcgccc agaggcgtgc cggccagcgg cgggggggcgc agtgcacacg      900 aggggggctgg acttcgcctg tgatatctac atctgggcgc ccttggccgg gacttgtggg      960
gtccttctcc tgtcactggt tatcacccctt tactgcaaac ggggcagaaa gaaactcctg     1020
tatatattca aacaaccatt tatgagacca gtacaaacta ctcaagagga agatggctgt     1080
agctgccgat ttccagaaga agaagaagga ggatgtgaac tgagagtgaa gttcagcagg     1140
agcgcagacg cccccgcgta ccagcagggc cagaaccagc tctataacga gctcaatcta     1200
ggacgaagag aggagtacga tgttttggac aagagacgtg gccgggaccc tgagatgggg     1260
ggaaagccgc agagaaggaa gaaccctcag gaaggcctgt acaatgaact gcagaaagat     1320
aagatggcgg aggcctacag tgagattggg atgaaaggcg agcgccggag gggcaagggg     1380
cacgatggcc tttaccaggg tctcagtaca gccaccaagg acacctacga cgcccttcac     1440
atgcaggccc tgcccctcg cggtagcggg gctacgaact tctcccttct taaacaagcg     1500
ggagacgtgg aagaaaatcc cggacctatg gccttaccag tgaccgcctt gctcctgccg     1560
ctggccttgc tgctccacgc cgccaggccg aactgggtga atgtaataag tgatttgaaa     1620
aaaattgaag atcttattca atctatgcat attgatgcta ctttatatac ggaaagtgat     1680
gttcacccca gttgcaaagt aacagcaatg aagtgctttc tcttggagtt acaagttatt     1740
tcacttgagt ccggagatgc aagtattcat gatacagtag aaaatctgat catcctagca     1800
aacaacagtt tgtcttctaa tgggaatgta acagaatctg gatgcaaaga atgtgaggaa     1860
ctggaggaaa aaaatattaa agaatttttg cagagttttg tacatattgt ccaaatgttc     1920
atcaacactt cttga                                                       1935
```

```
<210> SEQ ID NO 51
<211> LENGTH: 2016
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
```

```
atgtccgtgc ctacccaggt gctgggcctg ctgctgctgt ggctgaccga cgccagatgc       60
gaaatagtga tgacgcagtc tccagccacc ctgtctgtgt ctccagggga aagaaccacc      120
ctctcctgca gggccagtca gagtgttagc agcaacttag cctggtacct tcagaaacct      180
ggccaggctc ccaggctcct catctatggt gcatccacca gggccactgg tatcccagcc      240
aggttcagtg gcagtgggtc tgggacagag ttcattctca ccatcagcag cctgcagtct      300
```

-continued

```
gaagattttg cagtttatta ctgtcagcag tataataact ggccgatcac cttcggccaa      360
gggacacggc tggagattaa aggtggaggt ggatctggag gaggaggatc cggtggagga      420
ggtgaagtgc aactggtgga gtctggggga ggcttggtac agcctggcag gtccctgaga      480
ctctcctgtg cagcctctgg attcaccttt tatgattatg ccatgcactg ggtccggcaa      540
gctccaggga aggggctgga gtgggtctca ggtattagtt ggaatagtgg ttacataggc      600
tatgcggact ctgtgaaggg ccgattcacc atctccagag acaacgccaa gaactccctg      660
tatctgcaaa tgaacagtct gagagctgag gacacggcct tgtattactg tgcaaaagat      720
aacagctatg aaagttcta ctacggtttg gacgtctggg gccaagggac cacggtcacc      780
gtctcctcaa ccacgacgcc agcgccgcga ccaccaacac cggcgcccac catcgcgtcg      840
cagcccctgt ccctgcgccc agaggcgtgc cggccagcgg cggggggcgc agtgcacacg      900 aggggggctgg acttcgcctg tgatatctac atctgggcgc ccttggccgg gacttgtggg      960
gtccttctcc tgtcactggt tatcaccctt tactgcaaac ggggcagaaa gaaactcctg     1020
tatatattca aacaaccatt tatgagacca gtacaaacta ctcaagagga agatggctgt     1080
agctgccgat ttccagaaga agaagaagga ggatgtgaac tgagagtgaa gttcagcagg     1140
agcgcagacg cccccgcgta ccagcagggc cagaaccagc tctataacga gctcaatcta     1200
ggacgaagag aggagtacga tgtttttggac aagagacgtg gccgggaccc tgagatgggg     1260
ggaaagccgc agagaaggaa gaaccctcag gaaggcctgt acaatgaact gcagaaagat     1320
aagatggcgg aggcctacag tgagattggg atgaaaggcg agcgccggag gggcaagggg     1380
cacgatggcc tttaccaggg tctcagtaca gccaccaagg acacctacga cgcccttcac     1440
atgcaggccc tgccccctcg cggtagcggg gctacgaact ctcccttct taaacaagcg     1500 ggagacgtgg aagaaaatcc cggacctatg agaattccga aaccacattt gagaagtatt     1560
tccatccagt gctacttgtg tttacttcta aacagtcatt ttctaactga agctggcatt     1620
catgtcttca tttttgggctg tttcagtgca gggcttccta aaacagaagc caactgggtg     1680
aatgtaataa gtgatttgaa aaaaattgaa gatcttattc aatctatgca tattgatgct     1740
actttatata cggaaagtga tgttcacccc agttgcaaag taacagcaat gaagtgcttt     1800
ctcttggagt tacaagttat ttcacttgag tccggagatg caagtattca tgatacagta     1860
gaaaatctga tcatcctagc aaacaacagt ttgtcttcta atgggaatgt aacagaatct     1920
ggatgcaaag aatgtgagga actggaggaa aaaaatatta agaattttt gcagagtttt     1980 gtacatattg tccaaatgtt catcaacact tcttga                             2016
```

```
<210> SEQ ID NO 52
<211> LENGTH: 19
<212> TYPE: PRT
<213> ORGANISM: Porcine teschovirus 1

<400> SEQUENCE: 52

Ala Thr Asn Phe Ser Leu Leu Lys Gln Ala Gly Asp Val Glu Glu Asn
1               5                   10                  15

Pro Gly Pro

<210> SEQ ID NO 53
<211> LENGTH: 23
<212> TYPE: PRT
<213> ORGANISM: Foot-and-mouth disease virus

<400> SEQUENCE: 53
```

```
Val Lys Gln Thr Leu Asn Asn Phe Asp Leu Leu Lys Leu Ala Gly Asp
1               5                   10                  15

Val Glu Ser Asn Pro Gly Pro
            20
```

```
<210> SEQ ID NO 54
<211> LENGTH: 20
<212> TYPE: PRT
<213> ORGANISM: Equine rhinitis A virus

<400> SEQUENCE: 54

Gln Cys Thr Asn Tyr Ala Leu Leu Lys Leu Ala Gly Asp Val Glu Ser
1               5                   10                  15

Asn Pro Gly Pro
            20
```

```
<210> SEQ ID NO 55
<211> LENGTH: 17
<212> TYPE: PRT
<213> ORGANISM: Thosea asigna virus

<400> SEQUENCE: 55

Glu Gly Arg Ser Leu Leu Thr Cys Gly Asp Val Glu Glu Asn Pro Gly
1               5                   10                  15

Pro
```

```
<210> SEQ ID NO 56
<211> LENGTH: 553
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
ctaacgttac tggccgaagc cgcttggaat aaggccggtg tgcgtttgtc tatatgttat        60
tttccaccat attgccgtct tttggcaatg tgagggcccg gaaacctggc cctgtcttct       120
tgacgagcat tcctaggggt cttttcccctc tcgccaaagg aatgcaaggt ctgttgaatg      180
tcgtgaagga agcagttcct ctggaagctt cttgaagaca aacaacgtct gtagcgaccc       240
tttgcaggca gcggaacccc ccacctggcg acaggtgcct ctgcggccaa aagccacgtg       300
tataagatac acctgcaaag gcggcacaac cccagtgcca cgttgtgagt tggatagttg       360
tggaaagagt caaatggctc tcctcaagcg tattcaacaa ggggctgaag gatgcccaga       420 aggtaccccca ttgtatggga tctgatctgg ggcctcggtg cacatgcttt acatgtgttt      480
agtcgaggtt aaaaaaacgt ctaggccccc cgaaccacgg ggacgtggtt ttcctttgaa       540
aaacacgatg ata                                                          553
```

```
<210> SEQ ID NO 57
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Met Ser Val Pro Thr Gln Val Leu Gly Leu Leu Leu Leu Trp Leu Thr
1               5                   10                  15
```

-continued

```
Asp Ala Arg Cys Glu Ile Val Met Thr Gln Ser Pro Ala Thr Leu Ser
            20                  25              30

Val Ser Pro Gly Glu Arg Thr Thr Leu Ser Cys Arg Ala Ser Gln Ser
        35                  40              45

Val Ser Ser Asn Leu Ala Trp Tyr Leu Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Ile Leu Thr Ile Ser
                85                  90                  95

Ser Leu Gln Ser Glu Asp Phe Ala Val Tyr Tyr Cys Gln Gln Tyr Asn
            100                 105             110

Asn Trp Pro Ile Thr Phe Gly Gln Gly Thr Arg Leu Glu Ile Lys Gly
            115                 120             125

Gly Gly Gly Ser Gly Gly Gly Ser Gly Gly Gly Gly Glu Val Gln
        130                 135             140

Leu Val Glu Ser Gly Gly Gly Leu Val Gln Pro Gly Arg Ser Leu Arg
145                 150             155                 160

Leu Ser Cys Ala Ala Ser Gly Phe Thr Phe Tyr Asp Tyr Ala Met His
            165                 170             175

Trp Val Arg Gln Ala Pro Gly Lys Gly Leu Glu Trp Val Ser Gly Ile
            180                 185             190

Ser Trp Asn Ser Gly Tyr Ile Gly Tyr Ala Asp Ser Val Lys Gly Arg
            195                 200             205

Phe Thr Ile Ser Arg Asp Asn Ala Lys Asn Ser Leu Tyr Leu Gln Met
    210                 215             220

Asn Ser Leu Arg Ala Glu Asp Thr Ala Leu Tyr Tyr Cys Ala Lys Asp
225                 230             235                 240

Asn Ser Tyr Gly Lys Phe Tyr Tyr Gly Leu Asp Val Trp Gly Gln Gly
            245                 250             255

Thr Thr Val Thr Val Ser Ser Thr Thr Thr Pro Ala Pro Arg Pro Pro
            260                 265             270

Thr Pro Ala Pro Thr Ile Ala Ser Gln Pro Leu Ser Leu Arg Pro Glu
            275                 280             285

Ala Cys Arg Pro Ala Ala Gly Gly Ala Val His Thr Arg Gly Leu Asp
    290                 295             300

Phe Ala Cys Asp Ile Tyr Ile Trp Ala Pro Leu Ala Gly Thr Cys Gly
305                 310             315                 320

Val Leu Leu Leu Ser Leu Val Ile Thr Leu Tyr Cys Lys Arg Gly Arg
            325                 330             335

Lys Lys Leu Leu Tyr Ile Phe Lys Gln Pro Phe Met Arg Pro Val Gln
            340                 345             350

Thr Thr Gln Glu Glu Asp Gly Cys Ser Cys Arg Phe Pro Glu Glu Glu
            355                 360             365

Glu Gly Gly Cys Glu Leu Arg Val Lys Phe Ser Arg Ser Ala Asp Ala
        370                 375             380

Pro Ala Tyr Gln Gln Gly Gln Asn Gln Leu Tyr Asn Glu Leu Asn Leu
385                 390             395                 400

Gly Arg Arg Glu Glu Tyr Asp Val Leu Asp Lys Arg Arg Gly Arg Asp
                405                 410             415

Pro Glu Met Gly Gly Lys Pro Gln Arg Arg Lys Asn Pro Gln Glu Gly
            420                 425             430
```

```
Leu Tyr Asn Glu Leu Gln Lys Asp Lys Met Ala Glu Ala Tyr Ser Glu
        435                 440                 445

Ile Gly Met Lys Gly Glu Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

```
<210> SEQ ID NO 58
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58
```

```
Met Ala Leu Pro Val Thr Ala Leu Leu Leu Pro Leu Ala Leu Leu Leu
1               5                   10                  15

His Ala Ala Arg Pro Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
            115                 120                 125

Gln Met Phe Ile Asn Thr Ser
    130                 135
```

```
<210> SEQ ID NO 59
<211> LENGTH: 2489
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
```

```
atgtccgtgc ctacccaggt gctgggcctg ctgctgctgt ggctgaccga cgccagatgc      60
gaaatagtga tgacgcagtc tccagccacc ctgtctgtgt ctccagggga aagaaccacc     120
ctctcctgca gggccagtca gagtgttagc agcaacttag cctggtacct tcagaaacct     180
ggccaggctc ccaggctcct catctatggt gcatccacca gggccactgg tatcccagcc     240
aggttcagtg gcagtgggtc tgggacagag ttcattctca ccatcagcag cctgcagtct     300
gaagattttg cagtttatta ctgtcagcag tataataact ggccgatcac cttcggccaa     360
gggacacggc tggagattaa aggtggaggt ggatctggag gaggaggatc cggtggagga     420
ggtgaagtgc aactggtgga gtctggggga ggcttggtac agcctggcag gtccctgaga     480
```

-continued

```
ctctcctgtg cagcctctgg attcaccttt tatgattatg ccatgcactg ggtccggcaa      540
gctccaggga agggcctgga gtgggtctca ggtattagtt ggaatagtgg ttacataggc      600
tatgcggact ctgtgaaggg ccgattcacc atctccagag acaacgccaa gaactccctg      660
tatctgcaaa tgaacagtct gagagctgag gacacggcct tgtattactg tgcaaaagat      720
aacagctatg gaaagttcta ctacggtttg gacgtctggg gccaagggac cacggtcacc      780
gtctcctcaa ccacgacgcc agcgccgcga ccaccaacac cggcgcccac catcgcgtcg      840
cagcccctgt ccctgcgccc agaggcgtgc cggccagcgg cggggggcgc agtgcacacg      900 aggggggctgg acttcgcctg tgatatctac atctgggcgc ccttggccgg gacttgtggg      960
gtccttctcc tgtcactggt tatcaccctt tactgcaaac ggggcagaaa gaaactcctg     1020
tatatattca aacaaccatt tatgagacca gtacaaacta ctcaagagga agatggctgt     1080
agctgccgat ttccagaaga agaagaagga ggatgtgaac tgagagtgaa gttcagcagg     1140
agcgcagacg cccccgcgta ccagcagggc cagaaccagc tctataacga gctcaatcta     1200
ggacgaagag aggagtacga tgttttggac aagagacgtg gccgggaccc tgagatgggg     1260
ggaaagccgc agagaaggaa gaaccctcag gaaggcctgt acaatgaact gcagaaagat     1320
aagatggcgc aggcctacag tgagattggg atgaaaggcg agcgccggag gggcaagggg     1380
cacgatggcc tttaccaggg tctcagtaca gccaccaagg acacctacga cgcccttcac     1440
atgcaggccc tgccccctcg ctagagtact gcggccgcta cgtaaattcc gcccctctcc     1500
ctcccccccc cctaacgtta ctggccgaag ccgcttggaa taaggccggt gtgcgtttgt     1560
ctatatgtta ttttccacca tattgccgtc ttttggcaat gtgagggccc ggaaacctgg     1620
ccctgtcttc ttgacgagca ttcctagggg tctttcccct ctcgccaaag gaatgcaagg     1680
tctgttgaat gtcgtgaagg aagcagttcc tctggaagct tcttgaagac aaacaacgtc     1740
tgtagcgacc ctttgcaggc agcggaaccc cccacctggc gacaggtgcc tctgcggcca     1800
aaagccacgt gtataagata cacctgcaaa ggcggcacaa ccccagtgcc acgttgtgag     1860
ttggatagtt gtggaaagag tcaaatggct ctcctcaagc gtattcaaca aggggctgaa     1920
ggatgcccag aagtacccc attgtatggg atctgatctg gggcctcggt gcacatgctt     1980
tacatgtgtt tagtcgaggt taaaaaaacg tctaggcccc ccgaaccacg gggacgtggt     2040
tttcctttga aaaacacgat gatattaatt aagccaccgc catggcctta ccagtgaccg     2100
ccttgctcct gccgctggcc ttgctgctcc acgccgccag gccgaactgg gtgaatgtaa     2160
taagtgattt gaaaaaaatt gaagatctta ttcaatctat gcatattgat gctactttat     2220
atacggaaag tgatgttcac cccagttgca aagtaacagc aatgaagtgc tttctcttgg     2280
agttacaagt tatttcactt gagtccggag atgcaagtat tcatgataca gtagaaaatc     2340
tgatcatcct agcaaacaac agtttgtctt ctaatgggaa tgtaacagaa tctggatgca     2400
aagaatgtga ggaactggag gaaaaaaata ttaaagaatt tttgcagagt tttgtacata     2460
ttgtccaaat gttcatcaac acttcttga                                       2489
```

<210> SEQ ID NO 60
<211> LENGTH: 461
<212> TYPE: DNA
<213> ORGANISM: Foot-and-mouth disease virus A

<400> SEQUENCE: 60

```
agcaggtttc cccaactgac acaaaacgtg caacttgaaa ctccgcctgg tctttccagg       60
tctagagggg taacactttg tactgcgttt ggctccacgc tcgatccact ggcgagtgtt      120
```

-continued

```
agtaacagca ctgttgcttc gtagcggagc atgacggccg tgggaactcc tccttggtaa    180
caaggaccca cggggccaaa agccacgccc acacgggccc gtcatgtgtg caaccccagc    240
acggcgactt tactgcgaaa cccactttaa agtgacattg aaactggtac ccacacactg    300
gtgacaggct aaggatgccc ttcaggtacc ccgaggtaac acgcgacact cgggatctga    360
gaaggggact ggggcttcta taaaagcgct cggtttaaaa agcttctatg cctgaatagg    420
tgaccggagg tcggcacctt tcctttgcaa ttactgacca c                       461
```

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

```
<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81
```

-continued

```
000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000
```

```
<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Tyr Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Tyr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Tyr Gly Lys Phe Tyr Tyr Gly Leu Asp Val Trp
            100                 105                 110

Gly Gln Gly Thr Thr Val Thr Val Ser Ser
        115                 120
```

```
<210> SEQ ID NO 100

<400> SEQUENCE: 100

000

<210> SEQ ID NO 101
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Phe Thr Phe Tyr Asp Tyr Ala
1               5

<210> SEQ ID NO 102

<400> SEQUENCE: 102

000

<210> SEQ ID NO 103
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ile Ser Trp Asn Ser Gly Tyr Ile
1               5

<210> SEQ ID NO 104

<400> SEQUENCE: 104

000

<210> SEQ ID NO 105
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ala Lys Asp Asn Ser Tyr Gly Lys Phe Tyr Tyr Gly Leu Asp Val
1               5                   10                  15

<210> SEQ ID NO 106

<400> SEQUENCE: 106

000

<210> SEQ ID NO 107
<211> LENGTH: 107
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 107

Glu Ile Val Met Thr Gln Ser Pro Ala Thr Leu Ser Val Ser Pro Gly
1               5                   10                  15

Glu Arg Thr Thr Leu Ser Cys Arg Ala Ser Gln Ser Val Ser Ser Asn
            20                  25                  30

Leu Ala Trp Tyr Leu Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Ile Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys
            100                 105

<210> SEQ ID NO 108

<400> SEQUENCE: 108

000

<210> SEQ ID NO 109
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gln Ser Val Ser Ser Asn
1               5

<210> SEQ ID NO 110

<400> SEQUENCE: 110

000

<210> SEQ ID NO 111
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gly Ala Ser
1

<210> SEQ ID NO 112

<400> SEQUENCE: 112

000

<210> SEQ ID NO 113

-continued

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gln Gln Tyr Asn Asn Trp Pro Ile Thr
1               5

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123
```

-continued

```
<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134
```

```
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000
```

-continued

```
<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157
```

-continued

```
<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168
```

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

```
<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000
```

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Glu Val Gln Leu Ala Glu Ser Gly Gly Asp Leu Val Gln Ser Gly Arg
1               5                   10                  15

Ser Leu Arg Leu Ser Cys Ala Ala Ser Gly Ile Thr Phe His Asp Tyr
            20                  25                  30

Ala Met His Trp Val Arg Gln Pro Pro Gly Lys Gly Leu Glu Trp Val
        35                  40                  45

Ser Gly Ile Ser Trp Asn Ser Asp Tyr Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Pro Asp Asp Thr Ala Leu Tyr Tyr Cys
                85                  90                  95

Val Lys Asp Phe His Tyr Gly Ser Gly Ser Asn Tyr Gly Met Asp Val
            100                 105                 110

Trp Gly Gln Gly Thr Thr Val Thr Val Ser Pro
        115                 120

<210> SEQ ID NO 196

<400> SEQUENCE: 196

000

<210> SEQ ID NO 197

<400> SEQUENCE: 197

000

<210> SEQ ID NO 198

```
<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Val Lys Asp Phe His Tyr Gly Ser Gly Ser Asn Tyr Gly Met Asp Val
1               5                   10                  15

<210> SEQ ID NO 202

<400> SEQUENCE: 202

000

<210> SEQ ID NO 203
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Glu Ile Val Met Thr Gln Ser Pro Ala Thr Leu Ser Met Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Val Gly Gln Ala Pro Arg Leu Leu Ile
        35                  40                  45

Ser Gly Ala Ser Thr Arg Ala Thr Gly Ile Pro Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Val Tyr Tyr Cys Gln Gln Ser Asn Asp Trp Pro Leu
                85                  90                  95

Thr Phe Gly Gln Gly Thr Arg Leu Glu Ile Lys
            100                 105

<210> SEQ ID NO 204

<400> SEQUENCE: 204
```

```
000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Gln Gln Ser Asn Asp Trp Pro Leu Thr
1               5

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000
```

-continued

```
<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000
```

```
<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237
```

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 243

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Tyr Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asp Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Gly Ser Tyr Gly His Phe Tyr Ser Gly Leu Asp Val Trp
            100                 105                 110

Gly Gln Gly Thr Thr Val Thr Val Ser Ser
        115                 120

<210> SEQ ID NO 244

<400> SEQUENCE: 244

-continued

```
000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Thr Lys Asp Gly Ser Tyr Gly His Phe Tyr Ser Gly Leu Asp Val
1               5                   10                  15

<210> SEQ ID NO 250

<400> SEQUENCE: 250

000

<210> SEQ ID NO 251
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Val Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Asp Asp Phe Ala Val Tyr Tyr Cys Gln Gln Arg Tyr Tyr Trp Pro Leu
                85                  90                  95

Thr Phe Gly Gly Gly Thr Lys Val Glu Ile Lys
            100                 105

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Gln Gln Arg Tyr Tyr Trp Pro Leu Thr
1               5

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000
```

-continued

```
<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272
```

-continued

```
<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283
```

-continued

```
000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000
```

-continued

```
<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306
```

-continued

```
<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317
```

-continued

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

181                                                                                        182

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 339

```
Glu Glu Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe His Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Leu Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Pro Ser Tyr Gly Ser Gly Ser Tyr His Ser Tyr Tyr Gly
            100                 105                 110

Met Asp Val Trp Gly Gln Gly Thr Thr Val Thr Val Ser Ser
        115                 120                 125
```

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

```
Ala Lys Asp Pro Ser Tyr Gly Ser Gly Ser Tyr His Ser Tyr Tyr Gly
1               5                   10                  15

Met Asp Val
```

-continued

<210> SEQ ID NO 346

<400> SEQUENCE: 346

000

<210> SEQ ID NO 347
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 347

Glu Ile Val Leu Thr Gln Ser Pro Ala Thr Leu Ser Leu Ser Pro Gly
1               5                   10                  15

Glu Arg Ala Thr Leu Ser Cys Trp Ala Ser Gln Ser Ile Ser Arg Tyr
            20                  25                  30

Leu Val Trp Tyr Gln Gln Lys Cys Gly Gln Ala Pro Arg Leu Leu Ile
        35                  40                  45

Tyr Glu Ala Ser Lys Arg Ala Thr Gly Ile Pro Val Arg Phe Ser Gly
    50                  55                  60

Ser Gly Ser Gly Thr Asp Phe Thr Leu Thr Ile Ser Ser Leu Glu Ser
65                  70                  75                  80

Glu Asp Phe Ala Val Tyr Tyr Cys Gln Gln Arg Phe Asn Trp Pro Leu
                85                  90                  95

Thr Phe Gly Gly Gly Thr Lys Val Glu Ile Lys
            100                 105

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353
<211> LENGTH: 9

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Gln Gln Arg Phe Asn Trp Pro Leu Thr
1               5

<210> SEQ ID NO 354
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 354

Trp Leu Thr Lys Lys Lys Tyr Ser Ser Ser Val His Asp Pro Asn Gly
1               5                   10                  15

Glu Tyr Met Phe Met Arg Ala Val Asn Thr Ala Lys Lys Ser Arg Leu
            20                  25                  30

Thr Asp Val Thr Leu
        35

<210> SEQ ID NO 355
<211> LENGTH: 382
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 355
gaagtacagc tggtggagtc tggggggaggc ttggtacagc ctggcaggtc cctgagactc      60
tcctgtgtag cctctggatt cacctttaat gattatgcca tgcactgggt ccggcaagct     120
ccagggaagg gcctggaatg ggtctcagtt attagttgga atagtgatag cataggctat     180
gcggactctg tgaagggccg attcaccatc tccagagaca cgccaagaa ctccctgtat      240 ctgcaaatgc acagtctgag agctgaggac acggccttgt attactgtgc aaaagataat     300
cactatggtt cggggagtta ttactactac caatacggta tggacgtctg gggccaaggg     360
accacggtca ccgtctcctc ag                                              382

<210> SEQ ID NO 356
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 356

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45
```

```
Ser Val Ile Ser Trp Asn Ser Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Gln Tyr
                100                 105                 110

Gly Met Asp Val Trp Gly Gln Gly Thr Thr Val Thr Val Ser Ser
            115                 120                 125
```

<210> SEQ ID NO 357
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 357

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc cccgactcct catctatggt acatccacca gggccactgg tatcccagcc     180
aggttcagtg gcagtgggtc tgggacagag ttcactctca ccatcagcag cctgcagtct     240
gaagattttg cagtttatta ctgtcaacaa tataataact ggccgctcac tttcggcgga     300
gggaccaagg tggagatcaa ac                                              322
```

<210> SEQ ID NO 358
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 358

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105
```

<210> SEQ ID NO 359
<211> LENGTH: 367
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 359
caggtgcagc tggtggagtc tggggagac tcggtcaagc ctggagggtc cctgagactc      60
tcctgtgcag cctctggatt caccttcagt gactcctaca tgacttggat ccgccaggct     120
ccagggaagg ggctggagtg ggtttcattc attagtagta gtggaagtac catatattat     180
gcagactctg tgaagggccg attcaccatt tccagggaca acgtcaagaa gtcattgtat     240
ctgcagatga acagactgag agccgaggac acggccgtgt attactgtgc gagagaagaa     300
ccaggaaact acgtctatta cggtatggac gtctggggcc aagggaccac ggtcaccgtc     360
tcctcag                                                                367

<210> SEQ ID NO 360
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 360

Gln Val Gln Leu Val Glu Ser Gly Gly Asp Ser Val Lys Pro Gly Gly
1               5                   10                  15

Ser Leu Arg Leu Ser Cys Ala Ala Ser Gly Phe Thr Phe Ser Asp Ser
            20                  25                  30

Tyr Met Thr Trp Ile Arg Gln Ala Pro Gly Lys Gly Leu Glu Trp Val
        35                  40                  45

Ser Phe Ile Ser Ser Ser Gly Ser Thr Ile Tyr Tyr Ala Asp Ser Val
    50                  55                  60

Lys Gly Arg Phe Thr Ile Ser Arg Asp Asn Val Lys Lys Ser Leu Tyr
65                  70                  75                  80

Leu Gln Met Asn Arg Leu Arg Ala Glu Asp Thr Ala Val Tyr Tyr Cys
                85                  90                  95

Ala Arg Glu Glu Pro Gly Asn Tyr Val Tyr Tyr Gly Met Asp Val Trp
            100                 105                 110

Gly Gln Gly Thr Thr Val Thr Val Ser Ser
        115                 120

<210> SEQ ID NO 361
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 361
gaaattgtgg tgacacagtc tccagccacc ctgtctttgt ctccagggga aagagccacc      60
ctctcctgca ggaccagtca gactactacc agctacttag cctggtaccg acagaaacct     120
ggccaggctc ccaggctcct catctatgat gcatccaaca gggccgctgg catcccagcc     180
aggttcagtg gcagtgggtc tgggacagac ttcactctca ccatcaacag cctagagcct     240
gaagattttg cagtttatta ctgtcagctg cgtaccaact ggatcacctt cggccaaggg     300
acacgactgg agattaaac                                                    319

```
<210> SEQ ID NO 362
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 362

Glu Ile Val Val Thr Gln Ser Pro Ala Thr Leu Ser Leu Ser Pro Gly
1               5                   10                  15

Glu Arg Ala Thr Leu Ser Cys Arg Thr Ser Gln Thr Thr Thr Ser Tyr
            20                  25                  30

Leu Ala Trp Tyr Arg Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
    50                  55                  60

Ser Gly Ser Gly Thr Asp Phe Thr Leu Thr Ile Asn Ser Leu Glu Pro
65                  70                  75                  80

Glu Asp Phe Ala Val Tyr Tyr Cys Gln Leu Arg Thr Asn Trp Ile Thr
                85                  90                  95

Phe Gly Gln Gly Thr Arg Leu Glu Ile Lys
            100                 105

<210> SEQ ID NO 363
<211> LENGTH: 367
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 363
gaagtgcaac tggtggagtc tggggggaggc ttggtacagc ctggcaggtc cctgagactc      60
tcctgtgcag cctctggatt caccttttat gattatgcca tgcactgggt ccggcaagct     120
ccagggaagg gcctggagtg ggtctcaggt attagttgga atagtggtta cataggctat     180
gcggactctg tgaagggccg attcaccatc tccagagaca cgccaagaa ctccctgtat      240 ctgcaaatga acagtctgag agctgaggac acggccttgt attactgtgc aaaagataac     300
agctatggaa agttctacta cggtttggac gtctggggcc aagggaccac ggtcaccgtc     360
tcctcag                                                              367

<210> SEQ ID NO 364
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 364
gaaatagtga tgacgcagtc tccagccacc ctgtctgtgt ctccagggga agaaccacc       60 ctctcctgca gggccagtca gagtgttagc agcaacttag cctggtacct tcagaaacct     120
ggccaggctc ccaggctcct catctatggt gcatccacca gggccactgg tatcccagcc     180
aggttcagtg gcagtgggtc tgggacagag ttcattctca ccatcagcag cctgcagtct     240
```

-continued

```
gaagattttg cagtttatta ctgtcagcag tataataact ggccgatcac cttcggccaa      300
gggacacggc tggagattaa ac                                              322

<210> SEQ ID NO 365
<211> LENGTH: 370
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 365
gaagtgcagc tggtggagtc tgggggaggc ttggtacagc ctggcaggtc cctgcgactc       60
tcctgtgcag cctctggatt cacctttcga gattatacca tgcactgggt ccggcaaggt      120
ccagggaagg gcctggaatg ggtctcaggt attagttgga atagtgatta cataggctat      180
gcggactctg tgaagggccg attcaccatc tccagagaca cgccaagaa ctccctgtat      240 ctgcaaatga acagtctgag agttgaggac acggccttgt attactgtgc aaagctcagt      300
gggacctaca gggactactt ctacggagtg gacgtctggg gccaagggac cacggtcacc      360
gtctcctcag                                                            370

<210> SEQ ID NO 366
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 366

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Arg Asp Tyr
            20                  25                  30

Thr Met His Trp Val Arg Gln Gly Pro Gly Lys Gly Leu Glu Trp Val
        35                  40                  45

Ser Gly Ile Ser Trp Asn Ser Asp Tyr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Ala Lys Leu Ser Gly Thr Tyr Arg Asp Tyr Phe Tyr Gly Val Asp Val
            100                 105                 110

Trp Gly Gln Gly Thr Thr Val Thr Val Ser Ser
        115                 120

<210> SEQ ID NO 367
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 367
```

-continued

```
gaaattgtgt tgacacagtc tccagccacc ctgtctttgt ctccagggga aagagccgcc          60
ctctcctgca gggccagtca gagtgttagc aactacttag cctggtacca acagaaacct         120
ggccaggctc ccaggctcct catctatgat gcatccaaca gggccactgg catcccagcc         180
aggttcagtg gcagtgggtc tgggacagac ttcactctca ccatcagcag cctagagcct         240
gaagattttg cagtttatta ctgtcagcag cgtagcaact ggccgctcac tttcggcgga         300
gggaccaagg tggagatcag ac                                                  322
```

```
<210> SEQ ID NO 368
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 368

Glu Ile Val Leu Thr Gln Ser Pro Ala Thr Leu Ser Leu Ser Pro Gly
1               5                   10                  15

Glu Arg Ala Ala Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Arg
            100                 105
```

```
<210> SEQ ID NO 369
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Val" or "Thr"
<220> FEATURE:
<221> NAME/KEY: VARIANT
<222> LOCATION: (4)..(4)
<223> OTHER INFORMATION: /replace="Phe" or "Gly"
<220> FEATURE:
<221> NAME/KEY: VARIANT
<222> LOCATION: (5)..(5)
<223> OTHER INFORMATION: /replace="His"
<220> FEATURE:
<221> NAME/KEY: VARIANT
<222> LOCATION: (8)..(8)
<223> OTHER INFORMATION: /replace="His"
<220> FEATURE:
<221> NAME/KEY: VARIANT
<222> LOCATION: (9)..(9)
<223> OTHER INFORMATION: /replace="Phe"
<220> FEATURE:
<221> NAME/KEY: VARIANT
<222> LOCATION: (10)..(10)
<223> OTHER INFORMATION: /replace="Tyr"
<220> FEATURE:
```

```
<221> NAME/KEY: VARIANT
<222> LOCATION: (11)..(11)
<223> OTHER INFORMATION: /replace="Asn" or "Ser"
<220> FEATURE:
<221> NAME/KEY: VARIANT
<222> LOCATION: (12)..(12)
<223> OTHER INFORMATION: /replace="Gly" or "His"
<220> FEATURE:
<221> NAME/KEY: VARIANT
<222> LOCATION: (13)..(13)
<223> OTHER INFORMATION: /replace="Leu" or "Ser"
<220> FEATURE:
<221> NAME/KEY: VARIANT
<222> LOCATION: (14)..(14)
<223> OTHER INFORMATION: /replace="Met" or "Asp"
<220> FEATURE:
<221> NAME/KEY: VARIANT
<222> LOCATION: (15)..(15)
<223> OTHER INFORMATION: /replace="Asp" or "Val"
<220> FEATURE:
<221> NAME/KEY: VARIANT
<222> LOCATION: (16)..(16)
<223> OTHER INFORMATION: /replace="Val" or " "
<220> FEATURE:
<221> NAME/KEY: VARIANT
<222> LOCATION: (17)..(17)
<223> OTHER INFORMATION: /replace=" "
<220> FEATURE:
<221> NAME/KEY: VARIANT
<222> LOCATION: (18)..(18)
<223> OTHER INFORMATION: /replace=" "
<220> FEATURE:
<221> NAME/KEY: VARIANT
<222> LOCATION: (19)..(19)
<223> OTHER INFORMATION: /replace=" "
<220> FEATURE:
<221> NAME/KEY: SITE
<222> LOCATION: (1)..(19)
<223> OTHER INFORMATION: /note="Variant residues given in the sequence
      have no preference with respect to those in the annotations
      for variant positions"

<400> SEQUENCE: 369

Ala Lys Asp Pro Ser Tyr Gly Ser Gly Ser Tyr Tyr Gly Tyr Tyr Gly
1               5                  10                  15

Met Asp Val

<210> SEQ ID NO 370
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Tyr" or "Phe"
<220> FEATURE:
<221> NAME/KEY: VARIANT
<222> LOCATION: (5)..(5)
<223> OTHER INFORMATION: /replace="Asp" or "Tyr"
```

<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 370

Gln Gln Arg Asn Asn Trp Pro Leu Thr
1               5